United States Patent
Aikawa et al.

(10) Patent No.: US 11,274,306 B2
(45) Date of Patent: *Mar. 15, 2022

(54) METHOD FOR INHIBITING CALCIFICATION OF A SMOOTH MUSCLE CELL (SMC)

(71) Applicant: THE BRIGHAM AND WOMEN'S HOSPITAL, INC., Boston, MA (US)

(72) Inventors: Elena Aikawa, Chestnut Hill, MA (US); Claudia Goettsch, Brookline, MA (US); Masanori Aikawa, Chestnut Hill, MA (US)

(73) Assignee: THE BRIGHAM AND WOMEN'S HOSPITAL, INC., Boston, MA (US)

(*) Notice: Subject to any disclaimer, the term of this patent is extended or adjusted under 35 U.S.C. 154(b) by 66 days.

This patent is subject to a terminal disclaimer.

(21) Appl. No.: 16/662,776

(22) Filed: Oct. 24, 2019

(65) Prior Publication Data

US 2020/0095588 A1 Mar. 26, 2020

Related U.S. Application Data

(60) Continuation of application No. 15/783,947, filed on Oct. 13, 2017, now Pat. No. 10,508,278, which is a division of application No. 14/439,951, filed as application No. PCT/US2013/067969 on Nov. 1, 2013, now Pat. No. 9,822,366.

(60) Provisional application No. 61/721,727, filed on Nov. 2, 2012.

(51) Int. Cl.
| | |
|---|---|
| *C07K 16/28* | (2006.01) |
| *C12N 15/113* | (2010.01) |
| *A61K 31/7105* | (2006.01) |
| *A61K 31/713* | (2006.01) |
| *G01N 33/68* | (2006.01) |
| *C12Q 1/6883* | (2018.01) |

(52) U.S. Cl.
CPC ........ *C12N 15/1138* (2013.01); *A61K 31/713* (2013.01); *A61K 31/7105* (2013.01); *C07K 16/28* (2013.01); *C12Q 1/6883* (2013.01); *G01N 33/6872* (2013.01); *G01N 33/6893* (2013.01); *C12N 2310/14* (2013.01); *C12Q 2600/158* (2013.01); *C12Q 2600/16* (2013.01); *C12Q 2600/166* (2013.01); *G01N 2333/705* (2013.01); *G01N 2800/32* (2013.01); *G01N 2800/50* (2013.01)

(58) Field of Classification Search
CPC .................................................... C07K 16/28
See application file for complete search history.

(56) References Cited

U.S. PATENT DOCUMENTS

| | | |
|---|---|---|
| 2001/0046956 A1 | 11/2001 | Hadcock |
| 2007/0098812 A1 | 5/2007 | Feinstein et al. |
| 2011/0166036 A1 | 7/2011 | Nykjaer et al. |
| 2012/0009174 A1 | 1/2012 | Van Eyk et al. |
| 2012/0196286 A1 | 8/2012 | Weber et al. |

FOREIGN PATENT DOCUMENTS

| | | |
|---|---|---|
| JP | 2008239488 A | 10/2008 |
| JP | 2012-145570 A | 8/2012 |
| WO | 00/33865 A1 | 6/2000 |
| WO | 2006/047820 A1 | 5/2006 |
| WO | 2011/159762 A1 | 12/2011 |

OTHER PUBLICATIONS

Nilsson et al., "Endocytosis of Apolipoprotein A-V by Members of the Low Density Lipoprotein Receptor and the Vps10p Domain Receptor Families", The Journal of Biological Chemistry 283(38):25920-25927 (2008).
O'Donnell et al., "Genome-wide Association Study for Coronary Artery Calcification with Follow-up in Myocardial Infarction", Circulation 124(25):2855-2864 (2011).
Okayasu et al., "Low-density Lipoprotein Receptor Deficiency Causes Impaired Osteoclastogenesis and Increased Bone Mass in Mice because of Defect in Osteoclastic Cell-Cell Fusion", The Journal of Biological Chemistry 287(23):19229-19241 (2012).
Samani et al., "Genomewide Association Analysis of Coronary Artery Disease", New England Journal of Medicine 357(5):443-453 (2007).
Schoppet et al., "Serum Level of the Phosphaturic Factor FGF23 Is Associated with Abdominal Aortic Calcification in Men: The STRAMBO Study", The Journal of Clinical Endocrinology & Metabolism 97(4):E575-E583 (2012).
Shanahan et al., "Arterial Calcification in Chronic Kidney Disease: Key Roles for Calcium and Phosphate", Circulation Research 109:697-711 (2011).
Sinha et al., "Vascular calcification: mechanisms and management", The British Journal of Cardiology 15(6):316-321 (2008).
Taylor et al., "The cardiac valve interslilial cell", The International Journal of Biochemistry & Cell Biology 35:113-118 (2003).
Vaegter et al., "Sortilin associates with Trk receptors to enhance anterograde transport and signaling by neurotrophins", Nature Neuroscience 14(1):1-23 (2011).
Wang et al., "Role of TGF-β1 in Bone Matrix Production in Vascular Smooth Muscle Cells Induced by a High-Phosphate Environment", Nephron Experimental Nephrology 115:e60-e68 (2010).
Willnow et al., "VPS10P-domain receptors—regulators of neuronal viability and function", Nature Reviews—Neuroscience 9:899-909 (2008).
Zimmermann et al., "RNAi-mediated gene silencing in non-human primates", Nature 441:111-114 (2006).
Ai et al., "Activation of ER stress and mTORCI suppresses hepatic sortilin-1 levels in obese mice", The Journal of Clinical Investigation 122(5):1677-1687 (2012).

(Continued)

*Primary Examiner* — Gyan Chandra
(74) *Attorney, Agent, or Firm* — Nixon Peabody LLP; David S. Resnick; Ravinderjit Braich

(57) ABSTRACT

The invention relates to methods for decreasing, inhibiting, preventing, or reducing calcification by inhibiting sortilin 1.

9 Claims, 13 Drawing Sheets
(7 of 13 Drawing Sheet(s) Filed in Color)

Specification includes a Sequence Listing.

(56) References Cited

OTHER PUBLICATIONS

Aikawa et al., "An HMG-CoA Reductase Inhibitor, Cerivastatin, Suppresses Growth of Macrophages Expressing Matrix Metalloproteinases and Tissue Factor In Vivo and In Vitro", Circulation 103:276-283 (2001).

Aikawa et al., "Arterial and Aortic Valve Calcification Abolished by Elastolytic Cathepsin S Deficiency in Chronic Renal Disease", Circulation 119(13): 1785-1794 (2009).

Aikawa et al., "Multimodality Molecular Imaging Identifies Proteolytic and Osteogenic Activities in Early Aortic Valve Disease", Circulation 115:377-386 (2007).

Aikawa et al., "Osteogenesis Associates With Inflammation in Early-Stage Atherosclerosis Evaluated by Molecular Imaging In Vivo", Circulation 116:2841-2850 (2007).

Anderson, "Matrix Vesicles and Calcification", Current Rheumatology Reports 5:222-226 (2003).

Bode et al., "Interaction between S100A8/A9 and Annexin A6 is Involved in the Calcium-induced Cell Surface Exposition of S100A8/A9", The Journal of Biological Chemistry 283(46):31776-31784 (2008).

Bostrom et al., "The Regulation of Valvular and Vascular Sclerosis by Osteogenic Morphogens", Circulation Research 109(5):564-577 (2011).

Bucay et al., "osteoprotegerin-deficient mice develop early onset osteoporosis and arterial calcification", Genes & Development 12:1260-1268 (1998).

Campagnolo et al., "Sortilin Expression Is Essential for Pro-Nerve Growth Factor-Induced Apoptosis of Rat Vascular Smooth Muscle Cells", Plos One 9(1):e84969 (2014). (9 pages).

Chen et al., "Annexin-Mediated Matrix Vesicle Calcification in Vascular Smooth Muscle Cells", Journal of Bone and Mineral Research 23(11): 1798-1805 (2008).

Chen et al., "Identification and Characterization of Aortic Valve Mesenchymal Progenitor Cells with Robust Osteogenic Calcification Potential", The American Journal of Pathology 174(3): 1109-1119 (2009).

Creemers et al., "Circulating MicroRNAs: Novel Biomarkers and Extracellular Communicators in Cardiovascular Disease?", Circulation Research 110:483-495 (2012).

Croce et al., "MRP-8/14 is Critical for the Biological Response to Vascular Injury", Circulation 120(5);427-436 (2009).

Desjardins et al., "FGF23 is independently associated with vascular calcification but not bone mineral density in patients at various CKD stages", Osteoporosis International 23:2017-2025 (2012).

Dinsmore et al., "Vascular Calcification in Types II and IV Hyperlipoproteinemia: Radiographic Appearance and Clinical Significance", American Journal of Roentgenology 144:895-899 (1985).

El-Abbadi et al., "Phosphate feeding induces arterial medial calcification in uremic mice: role of serum phosphorus, fibroblast growth factor-23, and osteopontin", Kidney International 75:1297-1307 (2009).

Goettsch et al., "miR-125b Regulates Calcification of Vascular Smooth Muscle Cells", The American Journal of Pathology 179(4):1594-1600 (2011).

Goettsch et al., "The Osteoclast-Associated Receptor (OSCAR) Is a Novel Receptor Regulated by Oxidized Low-Density Lipoprotein in Human Endothelial Cells", Endocrinology 152(12):4915-4926 (2011).

Goettsch et al., "Sortilin 1 is a novel inducer of vascular calcification", Brigham and Women's Hospital (2012). (2 pages).

Goodman et al., "Vascular Calcification in Chronic Kidney Disease", American Journal of Kidney Diseases 43(3):572-579 (2004).

Grskovic et al., "Depletion of Annexin A5, Annexin A6, and Collagen X Causes No Gross Changes in Matrix Vesicle-Mediated Mineralization, but Lack of Collagen X Affects Hematopoiesis and the Th1/Th2 Response", Journal of Bone and Mineral Research 27(11):2399-2412 (2012).

Ichikawa et al., "A Phex Mutation in a Murine Model of X-Linked Hypophosphatemia Alters Phosphate Responsiveness of Bone Cells", Journal of Bone and Mineral Research 27(2):453-460 (2012).

Ishimura et al., "Cross-Sectional Association of Serum Phosphate With Carotid Intima-Medial Thickness in Hemodialysis Patients", American Journal of Kidney Diseases 45(5):859-865 (2005).

Jansen et al., "Roles for the pro-neurotrophin receptor sortilin in neuronal development, aging and brain injury", Nature Neuroscience 10(11):1449-1457 (2007).

Kaddai et al., "Involvement of TNF-α in abnormal adipocyte and muscle sortilin expression in obese mice and humans", Diabetologia 52:932-940 (2009).

Kapustin et al., "Calcium Regulates Key Components of Vascular Smooth Muscle Cell-Derived Matrix Vesicles to Enhance Mineralization", Circulation Research 109:e1-e12 (2011).

Kathiresan et al., "Genome-wide association of early-onset myocardial infarction with single nucleotide polymorphisms and copy number variants", Nature Genetics 41(3):334-341 (2009).

Kim, "Calcification of matrix vesicles in human aortic valve and aortic media", Federation Proceedings 35(2):156-162 (1976).

Kirsch et al., "Functional Differences Between Growth Plate Apoptotic Bodies and Matrix Vesicles", Journal of Bone and Mineral Research 18(10):1872-1881 (2003).

Kjolby et al., "Sort1, Encoded by the Cardiovascular Risk Locus 1p13.3, Isa Regulator of Hepatic Lipoprotein Export", Cell Metabolism 12:213-223 (2010).

Kwon et al., "Sortilin Associates with Transforming Growth Factor-β Family Proteins to Enhance Lysosome-mediated Degradation", The Journal of Biological Chemistry 286(24):21876-21885 (2011).

Lefrancois et al., "Inactivation of sortilin (a novel lysosomal sorting receptor) by dominant negative competition and RNA interference", Biological Procedures Online 7(1):17-25 (2005).

Li et al., "A dynamic model of calcific nodule destabilization in response to monocyte- and oxidized lipid-induced matrix metalloproteinases", American Journal of Physiology—Cell Physiology 302:C658-665 (2012).

Libby et al., "Stabilization of atherosclerotic plaques: New mechanisms and clinical targets", Nature Medicine 8(11):1257-1262 (2002).

Liberman et al., "Oxidant Generation Predominates Around Calcifying Foci and Enhances Progression of Aortic Valve Calcification", Arteriosclerosis, Thrombosis, and Vascular Biology 28:463-470 (2008).

Liu et al., "Pathogenic role of Fgf23 in Hyp mice", American Journal of Physiology—Endocrinology and Metabolism 291:E38-E49 (2006).

Ma et al., "Secretory Leukocyte Protease Inhibitor Binds to Annexin II, a Cofactor for Macrophage HIV-1 Infection", The Journal of Experimental Medicine 200(10):1337-1346 (2004).

Maeda et al., "Sortilin Is Upregulated During Osteoblastic Differentiation of Mesenchymal Stem Cells and Promotes Extracellular Matrix Mineralization", Journal of Cellular Physiology 193:73-79 (2002).

Martin et al., "Bone proteins PHEX and DMP1 regulate fibroblastic growth factor Fgf23 expression in osteocytes through a common pathway involving FGF receptor (FGFR) signaling", The FASEB Journal 25:2551-2562 (2011).

Mazella et al., "The 100-kDa Neurotensin Receptor Is gp95/Sortilin, A Non-G-Protein-coupled Receptor", The Journal of Biological Chemistry 273(41):26273-26276 (1998).

McCormick et al., "S100A8 and S100A9 in Human Arterial Wall. Implications for Atherogenesis", The Journal of Biological Chemistry 280(50):41521-41529 (2005).

Munck Petersen et al., "Propeptide cleavage conditions sortilin/neurotensin receptor-3 for ligand binding", The EMBO Journal 18(3):595-604 (1999).

Musunuru et al., "From noncoding variant to phenotype via SORT1 at the 1p13 cholesterol locus", Nature 466(7307):714-719 (2010).

Nakamura et al., "Coronary Calcification in Patients with Chronic Kidney Disease and Coronary Artery Disease", Clinical Journal of the American Society of Nephrology 1-9 (2009).

(56) References Cited

OTHER PUBLICATIONS

Navarro et al., "Shedding of the luminal domain of the neurotensin receptor-3/sortilin in the HT29 cell line", Biochemical and Biophysical Research Communications 298:760-764 (2002).
New et al., "Abstract 10866: Novel Role of Macrophage-derived Matrix Vesicles in Arterial Microcalcification", Circulation 124:A10866 (2011). (3 pages).
New et al., "Cardiovascular Calcification: An Inflammatory Disease", Circulation Journal 75:1305-1313 (2011).
New et al., "Molecular Imaging Insights Into Early Inflammatory Stages of Arterial and Aortic Valve Calcification", Circulation Research 108:1381-1391 (2011).
Nielsen et al., "Sortilin/Neurotensin Receptor-3 Binds and Mediates Degradation of Lipoprotein Lipase", The Journal of Biological Chemistry 274(13):8832-8836 (1999).

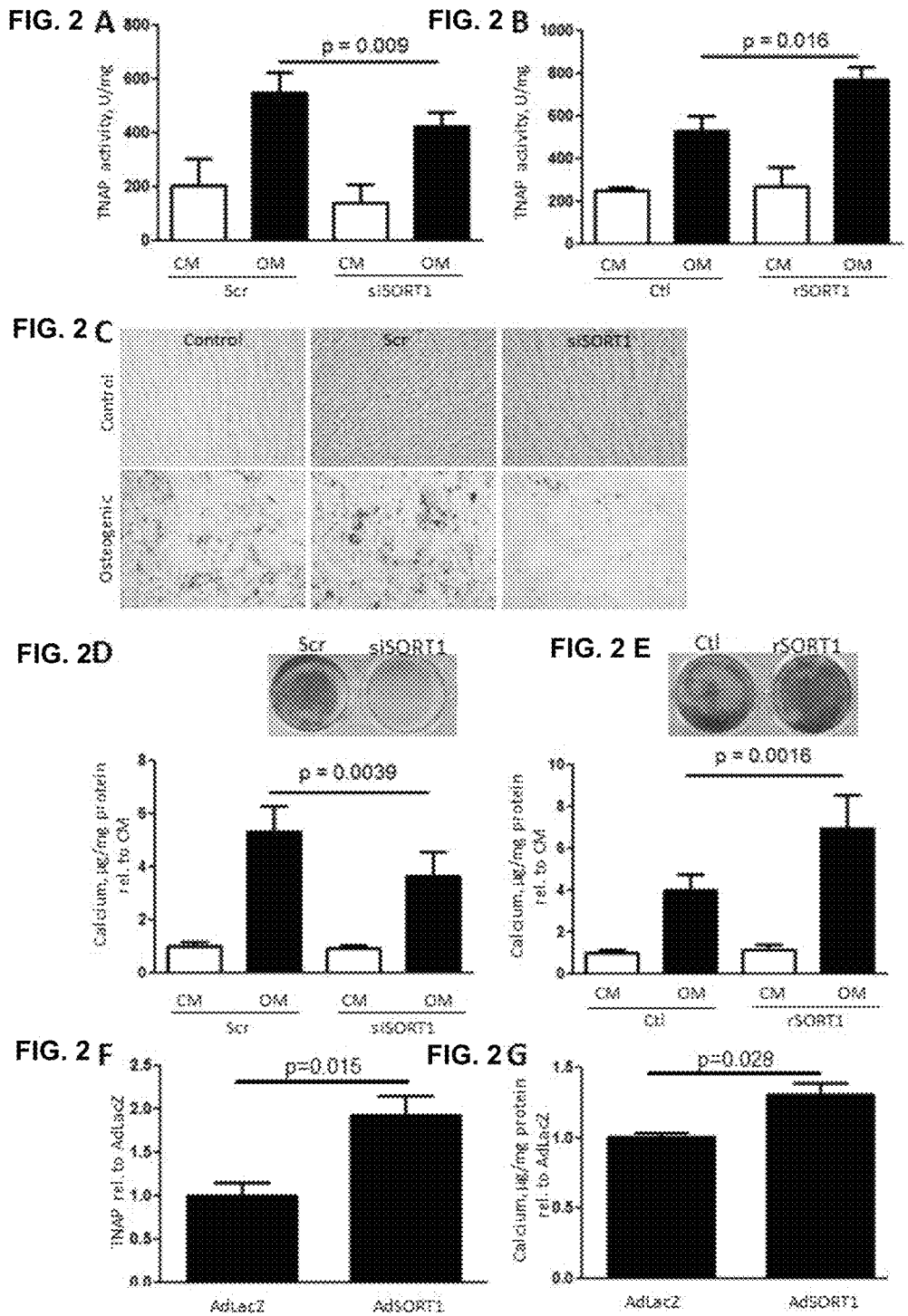

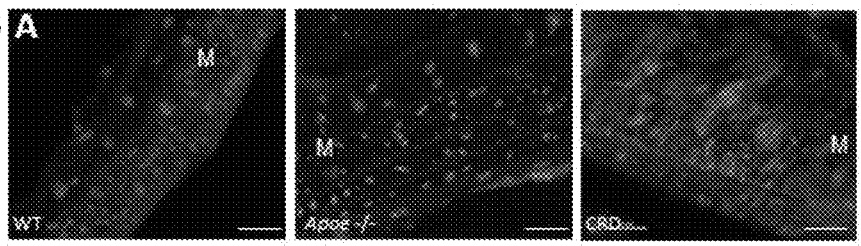
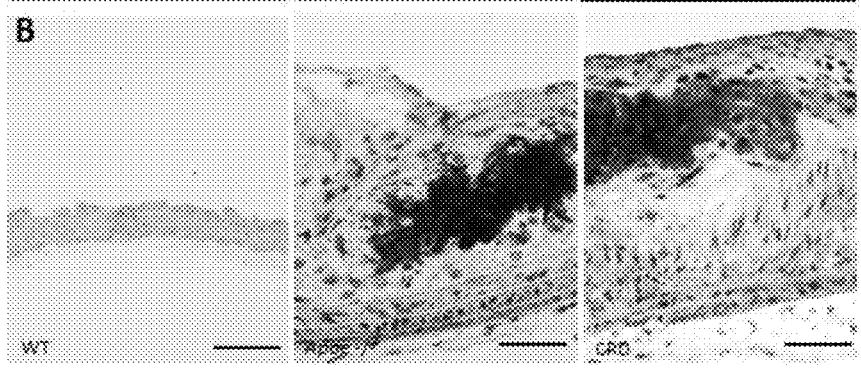
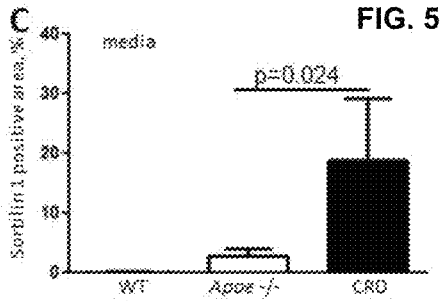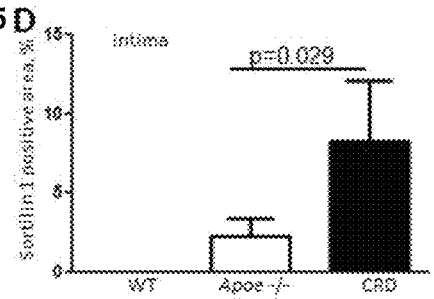
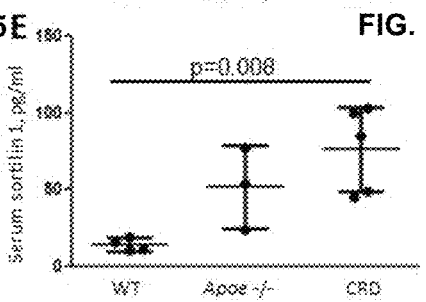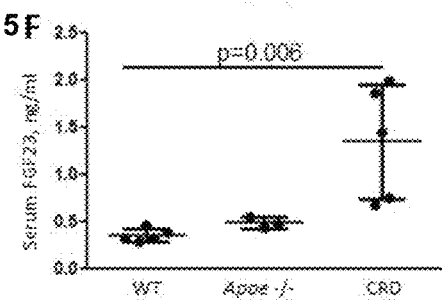
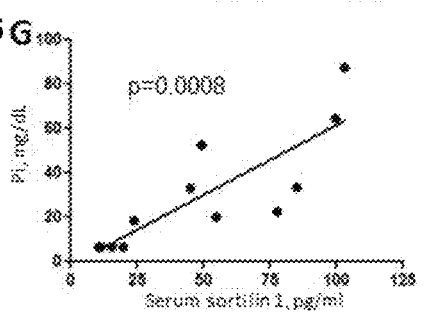

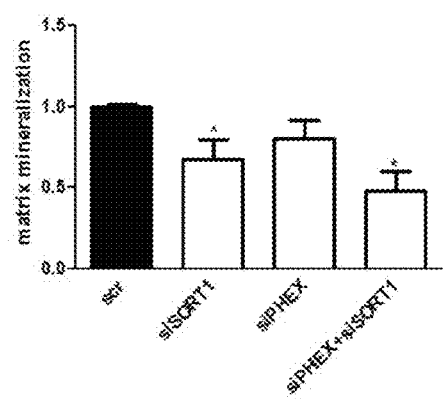
*FIG. 9*
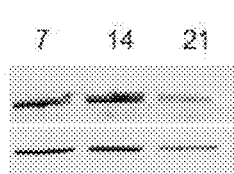
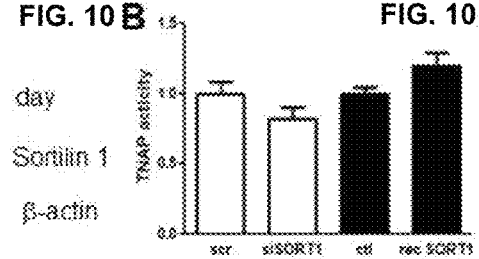
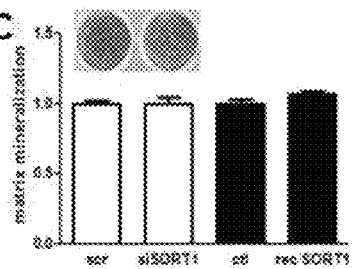
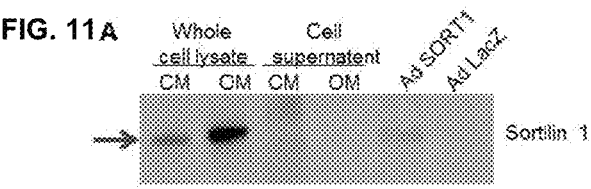
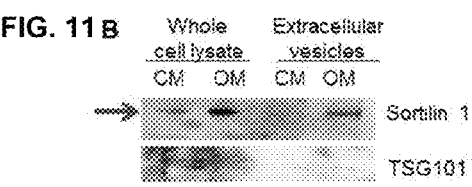

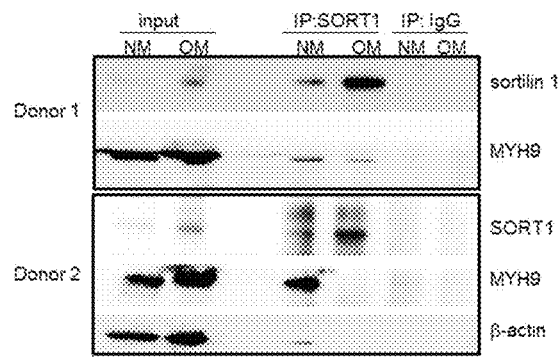
FIG. 12
FIG. 13 A
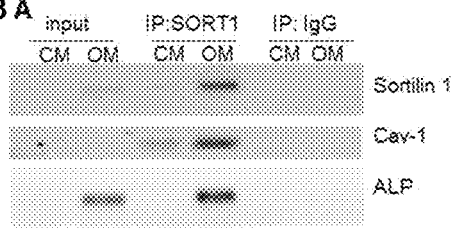
FIG. 13 B
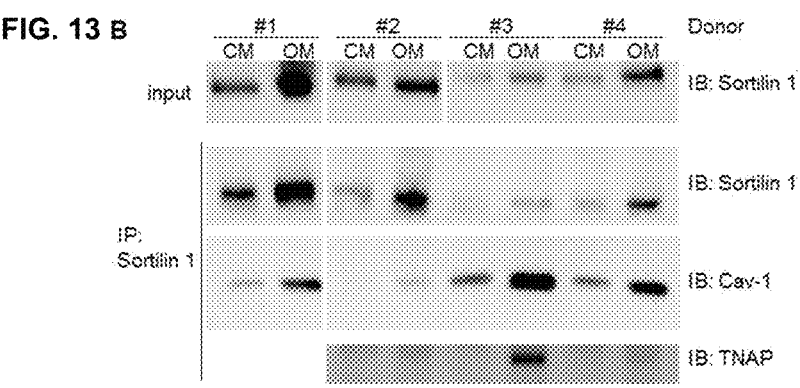

FIG. 17A
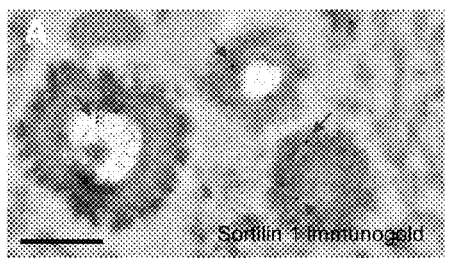
FIG. 17B
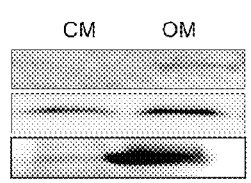
FIG. 17C
Sequenced peptides
Sortilin 1    AAAAGGAFPR
              TEFGMAIGPENSGK
Cav-1         SAPGEDEECG
TNAP          CTSNFLSPEK
FIG. 17D
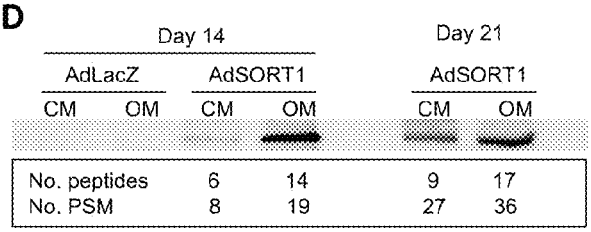
FIG. 17E
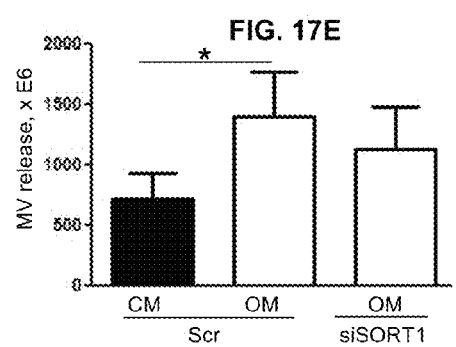

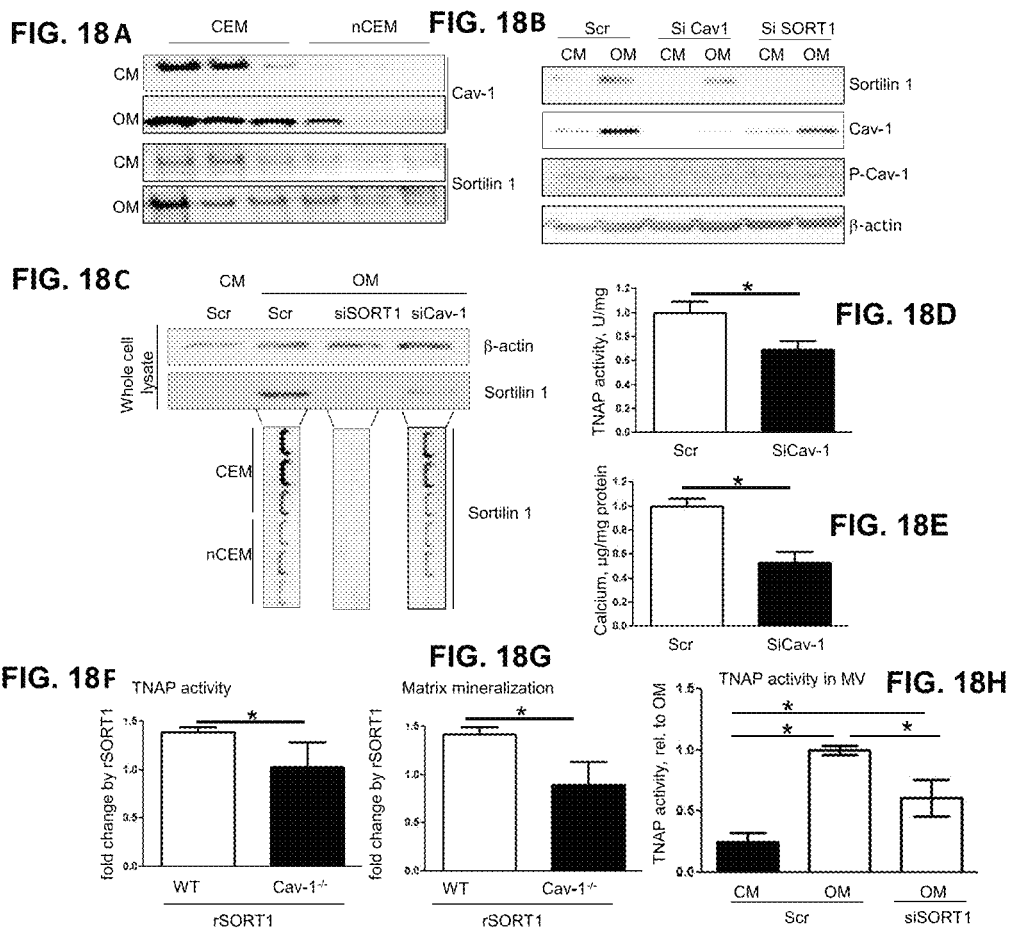

SEQUENCE LISTING

```
<160> NUMBER OF SEQ ID NOS: 10

<210> SEQ ID NO 1
<211> LENGTH: 17
<212> TYPE: RNA
<213> ORGANISM: Homo sapiens

<400> SEQUENCE: 1
aaaugcucag gguccccc                                                     17

<210> SEQ ID NO 2
<211> LENGTH: 10
<212> TYPE: PRT
<213> ORGANISM: Homo sapiens

<400> SEQUENCE: 2
```

Ala Ala Ala Ala Gly Gly Ala Phe Pro Arg
1               5                   10

<210> SEQ ID NO 3
<211> LENGTH: 14
<212> TYPE: PRT
<213> ORGANISM: Homo sapiens

<400> SEQUENCE: 3

Thr Glu Phe Gly Met Ala Ile Gly Pro Glu Asn Ser Gly Lys
1               5                   10

<210> SEQ ID NO 4
<211> LENGTH: 10
<212> TYPE: PRT
<213> ORGANISM: Homo sapiens

<400> SEQUENCE: 4

Ser Ala Pro Gly Glu Asp Glu Glu Cys Gly
1               5                   10

<210> SEQ ID NO 5
<211> LENGTH: 10
<212> TYPE: PRT
<213> ORGANISM: Homo sapiens

<400> SEQUENCE: 5

Cys Thr Ser Asn Phe Leu Ser Pro Glu Lys
1               5                   10

<210> SEQ ID NO 6
<211> LENGTH: 19
<212> TYPE: RNA
<213> ORGANISM: Artificial Sequence
<220> FEATURE:
<223> OTHER INFORMATION: Inhibitor sequence

<400> SEQUENCE: 6
gaauuuggca uggcuauug                                               19

<210> SEQ ID NO 7
<211> LENGTH: 19
<212> TYPE: RNA
<213> ORGANISM: Artificial Sequence
<220> FEATURE:
<223> OTHER INFORMATION: Inhibitor sequence

<400> SEQUENCE: 7
gaaggacuau accauaugg                                               19

<210> SEQ ID NO 8
<211> LENGTH: 19
<212> TYPE: RNA
<213> ORGANISM: Artificial Sequence
<220> FEATURE:
<223> OTHER INFORMATION: Inhibitor sequence

<400> SEQUENCE: 8
gagcuagguc caugaauau                                               19

<210> SEQ ID NO 9
<211> LENGTH: 19
<212> TYPE: RNA
<213> ORGANISM: Artificial Sequence
<220> FEATURE:
<223> OTHER INFORMATION: Inhibitor sequence

```
<400> SEQUENCE: 9
gagacuaugu ugugaccaa                                              19

<210> SEQ ID NO 10
<211> LENGTH: 13
<212> TYPE: PRT
<213> ORGANISM: Homo sapiens
<220> FEATURE:
<221> NAME/KEY: misc_feature
<222> LOCATION: (7)..(7)
<223> OTHER INFORMATION: phosphorylated Serine

<400> SEQUENCE: 10

Ser Gly Tyr His Asp Asp Xaa Asp Glu Asp Leu Leu Glu
1               5                   10
```

METHOD FOR INHIBITING CALCIFICATION OF A SMOOTH MUSCLE CELL (SMC)

CROSS REFERENCE TO RELATED APPLICATIONS

This application is a Continuation Application of U.S. application Ser. No. 15/783,947 filed on Oct. 13, 2017 which is a Divisional Application of U.S. application Ser. No. 14/439,951 filed on Apr. 30, 2015, which is a 371 National Phase Entry of International Patent Application No. PCT/US2013/067969 filed on Nov. 1, 2013 which claims the benefit under 35 U.S.C. § 119(e) of U.S. Provisional Application No. 61/721,727 filed Nov. 2, 2012, the contents of which are incorporated herein by reference in their entirety.

SEQUENCE LISTING

The sequence listing of the present application has been submitted electronically via EFS-Web as an ASCII formatted sequence listing with a file name 14439,951.txt, creation date of Aug. 13, 2017 and a size of 2,182 bytes. The sequence listing submitted via EFS-Web is part of the specification and is herein incorporated by reference in its entirety.

TECHNICAL FIELD

The present disclosure relates generally to methods and compositions for decreasing, inhibiting, treating, or preventing cardiovascular calcification, e.g., arterial and valvular microcalcification.

BACKGROUND

Vascular and valvular calcification, a prominent feature of chronic inflammatory disorders such as chronic renal disease, type II diabetes and dyslipidemia, associates with significant morbidity and mortality. Clinical, histological, and animal studies suggest that processes in vascular calcification are similar to those of bone remodeling (Hyder J A et al, American Journal of Epidemiology, 2009; Lieberman M et al, Arteriosclerosis, Thrombosis, and Vascular Biology, 2008; Bucay N et al, Genes & Development, 1998; Khosla S et al, Nature Medicine, 2011). Vascular calcification is an active, cell-regulated process in which vascular smooth muscle cells (SMCs) can lose the expression of their marker genes, acquire osteogenic markers, and deposit a mineralized bone-like matrix (Bostrom K I et al, Circulation Research, 2011). SMCs may play an important role in this process via transition toward an osteoblast-like state or releasing calcified matrix vesicles and microparticles.

Various therapeutic agents have been investigated to target cardiovascular calcification; these include statins (Aikawa E et al, Circulation, 2007; Monzack et al, ATVB, 2009; Osman L et al, Circulation, 2006; Rajamannan N M et al, Circulation, 2005; Wu Y W et al, Eur J Nucl Med Mol Imaging, 2012), bisphosphonate (Hartle J E et al, Am J Kidney Dis, 2012), phosphate binder (Di Iorio B et al, Clin J Am Soc Nephrol, 2012) and mineralocorticoid receptor antagonists (Gkizas S et al, Cardiovasc Pharma, 2010; Jaffe I Z et al, ATVB, 2007). However, beneficial effects of these drugs remain uncertain in the clinical setting (Gilmanov D, Inter. Cardiovasc Thor Surg, 2010). Thus, despite global clinical burden of cardiovascular calcification, no medical therapies are available.

Calcification in coronary arteries promotes heart attacks, which represent major health problems and economic burden in the United States. Calcification in carotid arteries associate with risk for stroke and dementia. Calcification in aortic valves causes aortic stenosis and heart failure. Especially, patients with mineral imbalance and calcium/phosphate disorders, including chronic renal disease, hemodyalysis and type II diabetes suffer from accelerated vascular and valvular calcification. For instance, arterio-venous shunts/grafts for hemodialysis in patients with chronic renal disease, vein grafts for peripheral arterial disease in diabetic patients, and saphenous vein bypass grafts for occluded coronary arteries in patients with metabolic disorders are often occluded within a year (vein graft failure). In the future, tissue engineered vascular and valvular implants in patients at metabolic risk may often fail. If the vein graft for peripheral arterial disease fails, the only options is an expensive redo surgery or stent implantation, or devastating amputation of the lower extremity. However, despite its high clinical and economic impact, no medical therapies are available to prevent or treat calcification.

SUMMARY

In part, this invention is based on inventors' discovery that sortilin 1 unexpectedly is an inducer of vascular calcification via a phosphate-dependent mechanism. The inventors have discovered inter alia that sortilin 1 is a novel regulator of hyperphosphatemia-triggered vascular calcification. As demonstrated herein, sortilin 1 promotes an osteogenic phenotype of SMC and may induce the release and calcification potential of matrix vesicles in a calciying environment. Without wishing to be bound by a theory, blocking sortilin 1 function by preventing its association with binding partners, inhibits calcification. The data presented herein shows that exogenous sortilin 1 increases calcification and serum sortilin 1 levels are elevated in atherosclerotic mice. Without limitations, neutralizing antibodies can be used to interfere the sortilin 1-mediated pro-calcific pathway. Small molecules and RNAi can also be used.

Accordingly, in one aspect provided herein is method of decreasing, inhibiting, preventing, or reducing calcification of SMCs. Generally, the method comprises contacting SMCs with a compound that can inhibit the activity or amount of sortilin 1 in SMCs. Alternatively, the method contacting SMCs with a compound that can inhibit the expression of a nucleic acid encoding sortilin 1 in the SMC.

The method described herein can be used for inhibiting, decreasing, preventing, or treating vascular calcification in a subject by administering a compound to the subject in need thereof, wherein the compound decreases, inhibits, prevents or reduces: (i) activity or amount of sortilin 1 in SMC; or (ii) expression of a nucleic acid encoding sortilin 1 in SMC; or (iii) phosphorylation of sortilin 1. In some embodiments, the compounds inhibits or reduces phosphorylation of serine 819 or/and 825 of sortilin 1. In some embodiments, said administering can be orally, intravenously, subcutaneously or locally.

In some embodiments, cardiovascular calcification is valvular or arterial microcalcification/gross calcification.

In some embodiments, the subject has chronic renal disease, severe renal failure treated with hemodialysis, hemodialysis AV grafts/shunts, vein grafts, vascular anastomsis, Paget's disease, diabetes, dyslipidemia, osteoarthritis, rheumatoid athritis or osteoporosis.

In some embodiments, the subject has a transcatheter valve implant.

In some embodiments, the subject has chronic coronary atherosclerosis or aortic stenosis.

In some embodiments, the nucleic acid encoding sortilin 1 is SORT 1 gene or SORT 1 mRNA.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A, Sortilin 1 (left) is expressed in calcified regions of human atherosclerotic carotid arteries. Purple staining by hematoxylin indicated calcified area. SMCs are stained with alpha smooth muscle cell actin (αSMA, middle) and macrophages with CD68 (right). One out of 20 patient samples is shown. Bar; 100 μm. FIG. 1B, Immunofluorescence microscopy shows the co-expression of sortilin 1 (left) and RUNX2 (middle) in human calcified lesion. Nuclei stained with DAPI (right). Bar; 50 μm. FIGS. 1C-1E, SMCs were cultured up to 21 days in control medium (CM) or osteogenic medium (OM). FIG. 1C, Sortilin 1 mRNA expression, relative to day 1, n=4 independent cell donor. $*p<0.05$. FIG. 1D, Sortilin 1 protein expression. Top: representative Western blot, bottom: statistical analysis, relative to day 1, n=4 independent cell donor. $*p<0.05$. FIG. 1E, Immunofluorescence microscopy shows the expression of sortilin 1 and osteopontin (OPN) in calcified SMCs (day 21). Bar; 100 μm. Error bars indicate SD.

FIGS. 2A-2G show that modification of sortilin 1 alters alkaline phosphatase activity and matrix mineralization in calcifying SMCs. SMCs were cultured for 14 (alkaline phosphatase activity) or 21 (matrix mineralization) days in control medium (CM), or osteogenic medium (OM). Sortilin 1 was either silenced by siRNA (A, B, D; siSORT or scramble control, Scr) or cells were stimulated with recombinant sortilin 1 (B, E; rSORT1, 200 ng/ml) twice per week during the entire cell culture period. FIGS. 2A and 2B, Tissue non-specific alkaline phosphatase activity (TNAP). FIG. 2C, Representative image of bright field SMCs showing the nodule formation. FIGS. 2D and 2E, Matrix mineralization. Top: Representative images of alizarin Red S-stained mineralized matrix. n=4 independent cell donor. FIGS. 2F and 2G, SMCs were cultured in osteogenic medium. Sortilin 1 was overexpressed by adenovirus (AdSORT1). LacZ served as control (AdLacZ). FIG. 2F, TNAP and FIG. 2G, Matrix mineralization. n=3 independent cell donor. Error bars indicate SD.

FIG. 3A, Cell viability at day 3 in osteogenic medium. n=3 independent cell donor. FIG. 3B, PHEX mRNA expression in calcified SMCs determined using PCR array. n=4 independent cell donor. FIGS. 3C and 3D, PHEX expression. Top: representative Western blot, b-actin served as loading control. Bottom: Quantification of mRNA expression. n=4 independent cell donor; $*p<0.05$. FIG. 3E, Correlation of PHEX and sortilin 1 mRNA expression. $r=-0.865$; $R^2=0.748$; $p=0.0001$. Error bars indicate SD.

FIG. 4A, the binding site for miR-125b within the SORT1 3'UTR is highly conserved between different species. Analysis was done using the website targetscan.com at 4-30-2012. Sequence shown is AAAUG-CUCAGGGUCCCC (SEQ ID NO: 1). FIGS. 4B-4D, SMCs were cultured in control medium (CM), or osteogenic medium (OM) and transfected with miR-125b inhibitor (Anti-125b), and the corresponding control (Scr) for 72 hours. FIG. 4B, miR-125b expression. FIG. 4C, Sortilin 1 expression. Top: representative Western blot, b-actin served as loading control. Bottom: mRNA expression. n=4 independent cell donor; $*p<0.05$. FIG. 4D, Correlation of miR-125b expression and sortilin 1 mRNA expression. $r=-0.825$; $R^2=0.681$; $p=0.043$. FIG. 4E, SORT1 3'UTR reporter activity is repressed by miR125b mimic (Pre-miR-125b) and induced by miR125b inhibitor (Anti-miR125b). Data are given as fold increase from the corresponding control. n=3 independent cell donor. $*p<0.05$. Error bars indicate SD FIGS. 5A-5G show that Sortilin 1 is increased in chronic renal disease, induced by 5/6 nephrectomy in Apoe-/- mice. FIG. 5A, Immunofluorescence staining of sortilin lin wild type (WT) and Apoe-/- mice without and with (CDR) 5/6 nephrectomy. Sortilin 1; red. DAPI; blue, autofluorescence; green. One of four animals per group is shown. Bar; 50 μm. FIG. 5B, Immunohistochemical staining of sortilin 1 in aorta of WT, Apoe-/- mice without and with chronic renal disease (CRD) 5/6 nephrectomy. One of four animals per group is shown. Magnification: 40x. FIGS. 5C and 5D, Quantification of sortilin 1 positive cells in atherosclerotic lesion. Separate analysis of vessel media (C) and intima (D). n=4. $*p<0.05$. FIG. 5E Sortilin 1 serum levels. n=3-5. FIG. 5F, FGF23 serum levels. n=3-5. FIG. 5G, Correlation of serum sortilin 1 and serum phosphate in WT, Apoe-- and CRD mice. n=12; $r=0.831$; $R^2=0.691$; $p=0.0008$. Dots indicate individual concentration. Error bars indicate SD.

FIG. 6A, Sortilin 1 was immunoprecipitated (IP) under low salt/stringency conditions from control (CM) or calcified (OM) SMCs cultured for 21 days after an IgG-pre-clearance. IgG-IP served as control. One out of two cell donors is shown. Coomassie Blue staining (top) of the gel and Western blot (bottom) of sortilin 1 is shown. Dotted boxes indicate the excised regions of each gel lane, across all four IP lanes. M; size marker in kDa. Green arrow heads indicate bands (myosin) that disappear in the OM conditions, the red arrow head indicates the molecular weight region corresponding to sortilin 1, and the black arrow head indicates vimentin. FIG. 6B, The log ratio plot of the relative peptide-spectrum matches (PSMs) between OM versus CM conditions.

FIG. 7A, Sortilin 1 mRNA at day 4, 14, and 21. n=2-4. Error bars indicate SD. FIG. 7B, Sortilin 1 protein. b-actin served as loading control. One out of four Western blots is shown.

FIGS. 8A and 8B, Collagen content of the extracellular matrix. FIG. 8C, RUNX2 mRNA expression. n=4 independent cell donor; *p<0.05. FIGS. 8D and 8E, SMCs were stimulated with phosphate (2 mM, 3 mM). 48 h later sortilin 1 mRNA (D) and protein (E) expression was determined. One out of three independent Western blot images is shown. n=3. *p<0.05. Error bars indicate SD.

FIG. 9 shows that phosphate regulating endopeptidase (PHEX) is not directly involved in sortilin-1 dependent SMC calcification. SMCs were cultured in osteogenic medium. Sortilin 1 (siSORT1) and PHEX (siPi-LEX) were silenced by siRNA (50 nM) or scramble control (scr) twice per week during the entire cell culture period. Matrix mineralization was measured at day 21. n=3 independent cell donor. Error bars indicate SD. *p<0.05 vs. scr.

FIGS. 10A-10C show that Sortilin 1 does not increase during osteoblastogenesis. FIG. 10A, Human mesenchymal stromal cells (hMSC) were cultured for up to 21 days in osteogenic medium. Protein expression was assessed by Western blot at the indicated time points. FIG. 10B, hMSC were cultured in osteogenic medium to obtain osteoblasts. Sortilin 1 (siSORT1) was silenced by siRNA (50 nM) or scramble control (scr) twice per week during the entire cell culture period. FIG. 10C, alkaline phosphatase, tissue non-specific (TNAP) activity measured at day 14. (C) Matrix mineralization measured at day 21. Representative images are shown above. n=3.

FIGS. 11A and 11B show that Sortilin 1 is released within extracellular vesicles from calcified SMC. FIG. 11A, Protein was precipitated from cell culture supernatant from control SMC (CM, day21); calcified SMC (OM, day 21) or SMC transduced for 7 days with adenovirus sortilin 1 (AdSORT1) or AdLacZ as control. Whole cell lysate from control SMC (CM, day21), calcified SMC (OM, day 21) served as control. FIG. 11B Extracellular vesicles were isolated from cell culture supernatant from control SMC (CM, day21) or calcified SMC (OM, day 21) using ultracentrifugation. 20 µg of protein were loaded on a gale. Whole cell lysate from control SMC (CM, day21), calcified SMC (OM, day 21) served as control.

FIG. 12 shows the association of sortilin 1 to myosin-9 and b-actin disappears in calcified SMC. SMCs were cultured for 21 days in control medium (NM) or osteogenic medium (OM). Sortilin 1 was immunoprecipitated after an IgG-pre-clearance. IgG-IP served as control. Western blot against sortilin 1, myosin-9 (MYH9) and b-actin. Two independent cell donors are shown.

FIGS. 13A and 13B show that association of sortilin 1 to caveolin-1 and tissue non-specific alkaline phosphatase increases in calcified SMC. SMCs were cultured for 21 days in control medium (CM) or osteogenic medium (OM). Sortilin 1 was immunoprecipitated after an IgG-pre-clearance. IgG-IP served as control. Western blot against sortilin 1, caveolin-1 (Cav-1) and tissue non-specific alkaline phosphatase (TNAP). FIG. 13A, Western blot of input, sortilin 1 IP and IgG IP. FIG. 13B, four independent cell donors are shown.

FIGS. 17A-17E show that sortilin 1 is loaded into matrix vesicles (MV).

FIG. 17A shows transmission electron microscopy-based immunogold staining of sortilin 1 on aorta sections of Apoe--/- mice with chronic renal disease. One out of three animals is shown. Bar=200 nm. FIG. 17B shows Sortilin 1, Caveolin-1 (Cav-1), and Tissue non-specific alkaline phosphatase (TNAP) expression in MVs isolated from SMCs cultured for 21 day in control (CM) or osteogenic (OM) medium. One out of three experiments is shown. FIG. 17C shows identification of sortilin 1 peptides in MVs using mass spectrometry. Peptide sequences are, from top to bottom: AAAAGGAFPR (SEQ ID NO: 2); TEFGMAIG-PENSGK (SEQ ID NO: 3); SAPGEDEECG (SEQ ID NO: 4); and CTSNFLSPEK (SEQ ID NO: 5). FIG. 17D, SMCs were cultured for 14, and 21 days in control (CM) or osteogenic medium (OM) under the adenoviral overexpression of sortilin 1 (Ad-SORT1) or the control vector (Ad-LacZ). MVs were isolated from the SMCs supernatant. Top: Western blot. Numbers represents the number of sequensed peptides and the corresponding peptide spectral matches (PSM). FIG. 17D shows MV release. n=4 independent cell donor. *p<0.05. Error bars indicate SD FIGS. 18A-18H show that sortilin 1 re-distributes to lipid raft/caveolae-enriched membrane in calcified SMCs. FIG. 18A, SMCs were cultured for 21 days in control (CM) or osteogenic (OM) medium. Lipid raft/caveolae-enriched membrane (CEM) were resolved from other cellular constituents (nCEM) by a hydrodynamic method. Caveolin-1 (Cav-1) and sortilin 1 protein expression were assessed by Western blot. One out of 3 independent cell donors is shown. FIGS. 18B and 18C, SMCs were cultured for 21 days in control medium (CM), or osteogenic medium (OM). Sortilin 1 and Caveolin-1 were silenced by siRNA (siSORT, siCav-1 or scramble control, Scr) twice per week during the entire cell culture period. Western blot of whole cell lysate (FIGS. 18B and 18C) and CEM/nCEM (FIG. 18C). One out of 3 independent cell donors is shown. FIGS. 18D and 18E, SMCs were cultured for 14 (FIG. 18D, Tissue non-specific alkaline phosphatase (TNAP) activity) or 21 (FIG. 18E, matrix mineralization) days in control medium (CM), or osteogenic medium (OM). Caveolin-1 was silenced by siRNA (siCav-1 or scramble control, Scr) twice per week during the entire cell culture period. n=4 independent cell donors. *p<0.05. FIGS. 18F and 18G, SMCs were isolated from caveolin-1-deficient mice (Cav-1$^{-/-}$) or wild type mice (WT) and cultured for 14 (FIG. 18F, Tissue non-specific alkaline phosphatase (TNAP) activity) or 21 (FIG. 18G, matrix mineralization) days in osteogenic medium with and without mouse recombinant sortilin 1 (rSORT1, 200 ng/ml). n=4. *p<0.05. FIG. 18H shows TNAP activity in MVs isolated from SMCs cultured for 14 days in control (CM) or osteogenic (OM) medium. Sortilin 1 was silenced by siRNA (siSORT, or scramble control, Scr) twice per week during the entire cell culture period. n=4 independent cell donor. *p<0.05. Error bars indicate SD.

DETAILED DESCRIPTION

Figure 1A:
FIGS. 1A-1E show that Sortilin 1 is induced in human calcified tissue and during osteogenic transition of human vascular SMCs.

In one aspect provided herein is a method of decreasing, inhibiting or preventing calcification of SMCs. Generally, the method comprises inhibiting sortilin 1. In some embodiments, the method comprising contacting a compound with SMCs, wherein the compound decreases, inhibits, prevents or reduces: (i) activity or amount of sortilin 1 in SMCs; (ii) expression of a nucleic acid encoding sortilin 1 in SMCs; or (iii) phosphorylation of serine 819 or/and 825.

The compounds which can decrease, inhibit, prevent or reduce the activity of sortilin or expression thereof are also referred to as sortilin inhibitors herein.

The terms "decrease," "inhibit," "reduced," or "reduction," in reference to activity, amount or expression of a nucleic acid encoding sortilin 1 generally mean a decrease by a statistically significant amount. However, for avoidance of doubt, "reduced", "reduction" or "decrease" or "inhibit" means a decrease by at least 10% as compared to a reference level, for example a decrease by at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95% but not 100% (e.g. absent level as compared to a reference sample) decrease. In some embodiments, decrease can be 100% (e.g., a level below limit of detection). Reference level can be the level in absence of the inhibitor.

Methods disclosed herein can be used to prevent or treat atherosclerotic calcification, medial calcification, aortic valve calcification, and other conditions characterized by cardiovascular calcification. For example, the methods disclosed herein can be used to prevent or treat calcification in patients with any mineral imbalance disorders, including severe renal failure on hemodialysis, hemodialysis AV grafts/shunts, vein grafts, various vascular anastomosis, diabetes, Paget's disease, rheumatoid arthritis, osteoporosis or some forms of osteoarthritis. Without wishing to be bound by a theory, in these indications, progression of vascular or valvular calcification can develop within weeks-months. In some embodiments, vascular/valvular (e.g., aortic valve, mitral annulus) calcification can be associated with chronic renal insufficiency or end-stage renal disease. In some embodiments, vascular/valvular calcification can be associated with pre- or post-dialysis or uremia. In some embodiments, vascular/valvular calcification can be associated with diabetes type I or II. In some embodiments, vascular/valvular calcification can be associated with a cardiovascular disorder. In some embodiments, vascular calcification can be associated with bone disease (Paget's disease, rheumatoid arthritis, osteoporosis, osteoarthritis).

Accordingly, presented herein are also methods for decreasing, inhibiting, preventing, or treating calcification, e.g., cardiovascular calcification, in a subject. The method comprising inhibiting the activity, amount or expression level of sortilin 1 in the subject. In some embodiments, the method comprising administering to a subject in need thereof a compound, wherein the compound decreases, inhibits, or reduces:

activity or amount of sortilin 1 in SMCs;
(ii) expression of a nucleic acid encoding sortilin 1 in SMCs; or
(iii) phosphorylation of serine 819 or/and 825.

In some embodiments, the inhibitor retards or reverses the formation, nucleation, aggregation, growth or deposition of extracellular matrix hydroxyapatite crystal deposits. In some embodiments, the inhibitor prevents the formation, nucleation, growth or deposition of extracellular matrix hydroxyapatite crystal deposits. In some embodiments, the inhibitor prevents the release, nucleation and calcification of matrix vesicles.

Without wishing to be bound by a theory, the inhibitor can act directly on sortilin 1 itself or a molecule or enzyme or on a pathway that acts on sortilin 1. For example, as the work reported herein demonstrates, sortilin 1 is a target for microRNA 125b (mir-125b). Thus, compounds or compositions that can increase miR-125b levels can repress expression of SORT 1 since miR-125b binds to 3'UTR of SORT1 and repress its expression.

The inventors have discovered that silencing of sortilin 1 significantly reduced alkaline phosphatase activity, matrix mineralization, matrix vesicle release, and increased calcific potential of such vesicles. Accordingly, in some embodiments, the sortilin inhibitor inhibits or reduces tissue non-specific alkaline phosphatase activity (TNAP) by at least 10%, for example a decrease by at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95% but not 100% (e.g. absent level as compared to a reference sample) decrease. In some embodiments, decrease can be 100% (e.g., a level below limit of detection). Reference level can be the level in absence of the inhibitor.

The inventors have shown that sortilin 1 associates with TNAP and Caveolin-1. Accordingly, in some embodiments, the sortilin inhibitor can inhibit the association of sortilin 1 to TNAP and/or Caveolin-1. In some embodiments, the sortilin inhibitor decreases, inhibits, prevents or reduces association of sortilin 1 to TNAP and/or Caveolin-1 by at least 10%, for example a decrease by at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95% but not 100% (e.g. absent level as compared to a reference sample) decrease. In some embodiments, decrease can be 100% (e.g., a level below limit of detection). Reference level can be the level in absence of the inhibitor.

In some embodiments, the sortilin inhibitor can decrease matrix mineralization by at least 10%, for example a decrease by at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or at least about 95% but not 100% (e.g. absent level as compared to a reference sample) decrease. In some embodiments, decrease can be 100% (e.g., a level below limit of detection). Reference level can be the level in absence of the inhibitor.

Inventors have also discovered that there is a significant inverse correlation between sortilin 1 and phosphate regulating endopeptidase (PHEX). Inhibition of sortilin 1 increased PHEX expression levels. Thus, in some embodiments, the sortilin inhibitor can increase PHEX expression by at least 10%, for example an increase by at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, at least about 95%, at least 1-fold, at least 1.25-folds, at least 2-fold, at least 2.5-folds, at least 5-folds, at least 10-folds, at least 50-folds or more. Reference level can be the level in absence of the inhibitor Reference level can be the level in absence of the inhibitor.

Based on their work, the inventors have further discovered that sortilin 1 is a target for microRNA 125b (mir125b). Mir125b binds to 3'UTR of SORT1 and represses its expression. Thus, without wishing to be bound by a theory, compounds or compositions that increase expression of mir125b can be used to inhibit sortilin 1 by repressing the expression of SORT 1. Accordingly, in some embodiments, the sortilin inhibitor can increase expression level of microRNA 125b by at least 10%, for example an increase by at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, at least about 95%, at least 1-fold, at least 1.25-folds, at least 2-fold, at least 2.5-folds, at least 5-folds, at least 10-folds, at least 50-folds or more. Reference level can be the level in absence of the inhibitor.

Without limitations, the inhibitor, can be selected from the group consisting of small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.

In some embodiments, the inhibitor is a small molecule. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

In some embodiments, the inhibitor is a nucleic acid molecule or an analog or derivate thereof. As used herein, the term "nucleic acid" or "oligonucleotide" or grammatical equivalents herein means at least two nucleotides, including analogs or derivatives thereof that are covalently linked together. Exemplary oligonucleotides include, but are not limited to, single-stranded and double-stranded siRNAs and other RNA interference reagents (RNAi agents or iRNA agents), shRNA (short hairpin RNAs), antisense oligonucleotides, aptamers, ribozymes, and microRNAs (miRNAs). The nucleic acids can be single stranded or double stranded. The nucleic acid can be DNA, RNA or a hybrid, where the nucleic acid contains any combination of deoxyribo- and ribonucleotides, and any combination of uracil, adenine, thymine, cytosine and guanine. The nucleic acids can comprise one or more backbone modifications, e.g., phosphoramidate (Beaucage et al., Tetrahedron 49(10):1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); and Nielsen, Nature, 365:566 (1993), content of all of which is herein incorporated by reference. The nucleic acids can also include modifications to nucleobase and/or sugar moieties of nucleotides. Exemplary sugar modifications at the sugar moiety include replacement of 2'-OH with halogens (e.g., fluoro), O-methyl, O-methoxyethyl, $NH_2$, SH and S-methyl. In some embodiments, the nucleic acid is a peptide nucleic acid (PNA). Without wishing to be bound by a theory, nucleic acid inhibitors can decrease, inhibit, or reduce the expression or amount of the nucleic acid encoding a component of the complex. Computational and experimental methods, including high throughput screening assays, for producing nucleic acid inhibitors, e.g., antisense oligonucleotides, siRNAs, ribozymes, aptamers, and the like, targeted to any target sequence are known in the art and available to one of skill in the art.

In some embodiments, the inhibitor is short interfering RNA (siRNA). The term "short interfering RNA" (siRNA), also referred to herein as "small interfering RNA" is defined as an agent which functions to inhibit expression of a target gene, e.g., by RNAi. A siRNA can be chemically synthesized, it can be produced by in vitro transcription, or it can be produced within a host cell. siRNA molecules can also be generated by cleavage of double stranded RNA, where one strand is identical to the message to be inactivated. The term "siRNA" refers to small inhibitory RNA duplexes that induce the RNA interference (RNAi) pathway. These molecules can vary in length (generally 18-30 base pairs) and contain varying degrees of complementarity to their target mRNA in the antisense strand. Some, but not all, siRNA have unpaired overhanging bases on the 5' or 3' end of the sense strand and/or the antisense strand. The term "siRNA" includes duplexes of two separate strands, as well as single strands that can form hairpin structures comprising a duplex region.

In some embodiments, the inhibitor is an antisense oligonucleotide or siRNA molecule comprising a part of (e.g., 10-50, 12-40, 15-30, 16-25, or 18-22 consecutive nucleotides) of the antisense sequence of a nucleic acid encoding sortilin 1, e.g. SORT 1. Nucleic acid sequence of human SORT 1 can be accessed by NCBI Reference Sequence: NM_002959.4. In some embodiments, the nucleic acid encoding sortilin 1 is SORT 1 mRNA.

In some embodiments, the inhibitor comprises the nucleic acid sequence

```
                                      (SEQ ID NO: 6)
     5'-GAAUUUGGCAUGGCUAUUG-3';

(SEQ ID NO: 7)
     5'-GAAGGACUAUACCAUAUGG-3';

(SEQ ID NO: 8)
     5'-GAGCUAGGUCCAUGAAUAU-3';
     or (SEQ ID NO: 9)
     5'-GAGACUAUGUUGUGACCAA-3'.
```

In some embodiments, the inhibitor is an antibody or a fragment thereof. The terms "antibody" and "antibodies" include polyclonal antibodies, monoclonal antibodies, humanized or chimeric antibodies, single chain Fv antibody fragments, Fab fragments, and F(ab)$_2$ fragments. Antibodies having specific binding affinity for sortilin 1 can be produced through standard methods. Alternatively, antibodies may be commercially available, for example, from R&D Systems, Inc., Minneapolis, Minn.

As used herein, the terms "antibody" and "antibodies" refer to intact antibody, or a binding fragment thereof that competes with the intact antibody for specific binding and includes chimeric, humanized, fully human, and bispecific antibodies. In some embodiments, binding fragments are produced by recombinant DNA techniques. In additional embodiments, binding fragments are produced by enzymatic or chemical cleavage of intact antibodies. Binding fragments include, but are not limited to, Fab, Fab', F(ab')$_2$, Fv, and single-chain antibodies.

Unless it is specifically noted, as used herein a "fragment thereof" in reference to an antibody refers to an immune-specific fragment, i.e., an antigen-specific or binding fragment.

Monoclonal antibodies, which are homogeneous populations of antibodies to a particular epitope contained within an antigen, can be prepared using standard hybridoma technology. In particular, monoclonal antibodies can be obtained by any technique that provides for the production of antibody molecules by continuous cell lines in culture such as described by Kohler, G. et al., *Nature,* 1975, 256:495, the human B-cell hybridoma technique (Kosbor et al., *Immunology Today,* 1983, 4:72; Cole et al., *Proc. Natl. Acad. Sci. USA,* 1983, 80:2026), and the EBV-hybridoma technique (Cole et al., *Monoclonal Antibodies and Cancer Therapy,* Alan R. Liss, Inc., 1983, pp. 77-96). Such antibodies can be of any immunoglobulin class including IgG, IgM, IgE, IgA, IgD, and any subclass thereof. The hybridoma producing the monoclonal antibodies of the invention can be cultivated in vitro or in vivo.

Polyclonal antibodies are heterogeneous populations of antibody molecules that are specific for a particular antigen, which are contained in the sera of the immunized animals. Polyclonal antibodies are produced using well-known methods. A chimeric antibody is a molecule in which different portions are derived from different animal species, such as those having a variable region derived from a murine monoclonal antibody and a human immunoglobulin constant region. Chimeric antibodies can be produced through standard techniques. Antibody fragments that have specific binding affinity for a component of the complex can be generated by known techniques. For example, such fragments include, but are not limited to, F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed. See, for example, Huse et al., 1989, *Science,* 246: 1275. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

In some embodiments, the antibody or antigen-binding fragment thereof is murine. In some embodiments, the antibody or antigen-binding fragment thereof is from rabbit. In some embodiments, the antibody or antigen-binding fragment thereof is from rat. In other embodiments, the antibody or antigen binding fragment thereof is human. In some embodiments the antibody or antigen-binding fragment thereof is recombinant, engineered, humanized and/or chimeric.

In some embodiments, an antibody, or antigen binding fragment, variant, or derivative thereof for use in the methods of the invention binds specifically to at least one epitope of target molecule (e.g., sortilin 1), i.e., binds to such an epitope more readily than it would bind to an unrelated, or random epitope; binds preferentially to at least one epitope of sortilin, i.e., binds to such an epitope more readily than it would bind to a related, similar, homologous, or analogous epitope; competitively inhibits binding of a reference antibody which itself binds specifically or preferentially to an epitope of the target molecule (e.g., sortilin 1); or binds to at least one epitope of the target molecule (e.g., sortilin 1) with an affinity characterized by a dissociation constant Kd of about $5\times10^{-2}$ M, about $10^{-2}$ M, about $5\times10^{-3}$ M, about $10^{-3}$ M, about $5\times10^{-4}$ M, about $10^{-4}$ M, about $5\times10^{-5}$ M, about $10^{-5}$ M, about $5\times10^{-6}$ M, about $10^{-6}$ M, about $5\times10^{-7}$ M, about $10^{-7}$ M, about $5\times10^{-8}$ M, about $10^{-8}$ M, about $5\times10^{-9}$ M, about $10^{-9}$ M, about $5\times10^{-10}$ M, about $10^{-10}$ M, about $5\times10^{-11}$ M, about $10^{-11}$ M, about $5\times10^{-12}$ M, about $10^{-12}$ M, about $5\times10^{-13}$ M, about $10^{-13}$ M, about $5\times10^{-14}$ M, about $10^{-14}$ M, about $5\times10^{-15}$ M, or about $10^{-15}$ M.

In some embodiments, the antibody or fragment thereof preferentially binds to a human sortilin polypeptide or fragment thereof, relative to a murine sortilin polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$ M" can include, for example, from 0.05 M to 0.005 M.

In some embodiments, an antibody, or antigen binding fragment, variant, or derivative thereof for use in the methods described herein binds sortilin polypeptides or fragments or variants thereof with an off rate (k(off)) of less than or equal to about $5\times10^{-2}$ sec$^{-1}$, about $10^{-2}$ sec$^{-1}$, about $5\times10^{-3}$ sec$^{-1}$, about $10^{-1}$ sec$^{-1}$, about $5\times10^{-4}$ sec$^{-1}$, about $10^{-4}$ sec$^{-1}$, about $5\times10^{-4}$ sec$^{-1}$, about $10^{-4}$ sec$^{-1}$, about $5\times10^{-5}$ sec$^{-1}$, about $10^{-5}$ sec$^{-1}$, about $5\times10^{-6}$ sec$^{-1}$, about $10^{-6}$ sec$^{-1}$, about $5\times10^{-7}$ sec$^{-1}$, or about $10^{-7}$ sec$^{-1}$.

In other embodiments, an antibody, or antigen-binding fragment, variant, or derivative thereof for use in the methods described herein binds sortilin polypeptides or fragments or variants thereof with an on rate (k(on)) of greater than or equal to about $10^3$ M$^{-1}$ sec$^{-1}$, about $5\times10^3$ M$^{-1}$ sec$^{-1}$, $10^4$ M$^{-1}$ sec$^{-1}$, about $5\times10^4$ M$^{-1}$ sec$^{-1}$, $10^5$ M$^{-1}$ sec$^{-1}$, about $5\times10^5$ M$^{-1}$ sec$^{-1}$, $10^6$ M$^{-1}$ sec$^{-1}$, about $5\times10^7$ M$^{-1}$ sec$^{-1}$.

The binding affinity and dissociation rate of an antibody for use in the methods described herein can be determined by any method known in the art. For example, the binding affinity can be measured by competitive ELISAs, RIAs, BIACORE™, or KINEXA™ technology. The dissociation rate also can be measured by BIACORE™ or KINEXA™ technology. The binding affinity and dissociation rate are measured by surface plasmon resonance using, e.g., a BIACORE™.

In some embodiments, an antibody or an antigen-binding fragment for use in the methods described herein modulates the binding of a second molecule to sortilin. In some embodiments, the modulation is enhancement of the binding of the second molecule to sortilin. In some embodiments, the modulation is inhibition of the binding of the second molecule to sortilin. The IC50 of such inhibition can be measured by any method known in the art, e.g., by ELISA, RIA, or Functional Antagonism. In some embodiments, the IC50 is between 0.1 and 500 nM. In some embodiments, the IC50 is between 10 and 400 nM. In yet other embodiments, the antibody or portion thereof has an IC50 of between 60 nM and 400 nM.

Antibodies for use in the methods of the invention can be generated by immunization of a suitable host (e.g., vertebrates, including humans, mice, rats, sheep, goats, pigs, cattle, horses, reptiles, fishes, amphibians, and in eggs of birds, reptiles and fish). Such antibodies may be polyclonal or monoclonal. In some embodiments, the host is immunized with an immunogenic sortilin. In other embodiments, the host is immunized with sortilin associated with a cell membrane of an intact or disrupted cell and antibodies for use in the methods of the invention are identified by binding to sortilin.

In some embodiments, the sortilin antigen is administered with an adjuvant to stimulate the immune response. Adjuvants often need to be administered in addition to antigen in order to elicit an immune response to the antigen. These adjuvants are usually insoluble or nondegradable substances that promote nonspecific inflammation, with recruitment of mononuclear phagocytes at the site of immunization. Examples of adjuvants include, but are not limited to, Freund's adjuvant, RIBI (muramyl dipeptides), ISCOM (immunostimulating complexes) or fragments thereof.

For a review of methods for making antibodies, see, e.g., Harlow and Lane, Antibodies, A Laboratory Manual (1988); Yelton, D. E. et al., Ann. Rev. of Biochem. 50:657-80. (1981); and Ausubel et al., Current Protocols in Molecular Biology (New York: John Wiley & Sons) (1989). Determination of immunoreactivity with an immunogenic sortilin polypeptide may be made by any of several methods well known in the art, including, e.g., immunoblot assay and ELISA.

Anti-sortilin antibodies for use in the methods described herein can be of any isotype. An antibody of any desired isotype can be produced by class switching. For class switching, nucleic acids encoding VL or VH, that do not include any nucleotide sequences encoding CL or CH, are isolated using methods well known in the art. The nucleic acids encoding VL or VH are then operatively linked to a nucleotide sequence encoding a CL or CH from a desired class of immunoglobulin molecule. This can be achieved using a vector or nucleic acid that comprises a CL or CH chain, as described above. For example, an anti-sortilin antibody for use in the methods described herein that was originally IgM can be class switched to an IgG. Further, the class switching can be used to convert one IgG subclass to another, e.g., from IgG1 to IgG2.

The class and subclass of anti-sortilin antibodies can be determined by any method known in the art. In general, the class and subclass of an antibody can be determined using antibodies that are specific for a particular class and subclass of antibody. Such antibodies are available commercially. The class and subclass can be determined by ELISA, Western Blot, as well as other techniques. Alternatively, the class and subclass can be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

In certain embodiments both the variable and constant regions of sortilin antibodies or immunospecific fragments thereof for use in the treatment methods disclosed herein are fully human. Fully human antibodies can be made using techniques that are known in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems, as described in more detail elsewhere herein.

Antibodies or fragments thereof for use in the treatment methods disclosed herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, or derivatization by known protecting/blocking groups, proteolytic cleavage, linkage to a cellular ligand or other protein. Any of numerous chemical modifications may be carried out by known techniques, including, but not limited to, specific chemical cleavage, acetylation, formylation, etc . . . . Additionally, the derivative can contain one or more non-classical amino acids.

In some embodiments, antibody or fragment thereof for use in the methods disclosed herein will not elicit a deleterious immune response in the mammal to be treated, e.g., in a human. In one embodiment, the antibodies or fragments thereof for use in the methods disclosed herein can be modified to reduce their immunogenicity using art-recognized techniques. For example, antibodies can be humanized, primatized, deimmunized, or chimeric antibodies can be made. These types of antibodies are derived from a nonhuman antibody, typically a murine or primate antibody, that retains or substantially retains the antigen-binding properties of the parent antibody, but which is less immunogenic in humans. This can be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., Proc. Natl. Acad. Sci. USA 81:6851-6855 (1984); Morrison et al., Adv. Immunol. 44:65-92 (1988); Verhoeyen et al., Science 239:15341536 (1988); Padlan, Molec. Immun. 28:489-498 (1991); Padlan, Molec. Immun. 31:169-217 (1994), and U.S. Pat. Nos. 5,585,089; 5,693,761; 5,693, 762; and 6,190,370, all of which are hereby incorporated by reference in their entirety.

De-immunization can also be used to decrease the immunogenicity of an antibody. As used herein, the term "de-immunization" includes alteration of an antibody to modify T cell epitopes (see, e.g., WO9852976A1, WO0034317A2). For example, VH and VL sequences from the starting antibody are analyzed and a human T cell epitope "map" from each V region showing the location of epitopes in relation to complementarity-determining regions (CDRs) and other key residues within the sequence. Individual T cell epitopes from the T cell epitope map are analyzed in order to identify alternative amino acid substitutions with a low risk of altering activity of the final antibody. A range of alternative VH and VL sequences are designed comprising combinations of amino acid substitutions and these sequences are subsequently incorporated into a range of binding polypeptides, e.g., anti-sortilin antibodies or immunospecific fragments thereof for use in the methods disclosed herein, which are then tested for function. Typically, between 12 and 24 variant antibodies are generated and tested. Complete heavy and light chain genes comprising modified V and human C regions are then cloned into expression vectors and the subsequent plasmids introduced into cell lines for the production of whole antibody. The antibodies are then compared in appropriate biochemical and biological assays, and the optimal variant is identified.

Completely human antibodies are particularly desirable for therapeutic treatment of human patients. Human antibodies can be made by a variety of methods known in the art including phage display methods using antibody libraries derived from human immunoglobulin sequences. See, for example, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety.

Completely human antibodies which recognize a selected epitope can be generated using a technique referred to as "guided selection." In this approach a selected nonhuman monoclonal antibody, e.g., a mouse antibody, is used to guide the selection of a completely human antibody recognizing the same epitope. (Jespers et al., Bio/Technology 12:899-903 (1988)). See also, U.S. Pat. No. 5,565,332. [0162] In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and subcloned hybridoma cells serve as a preferred source of such DNA. Once isolated, the DNA may be placed into expression vectors, which are then transfected into prokaryotic or eukaryotic host cells such as E. coli cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al., U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Anti-sortilin antibodies can be purchased from Abcam (Cambridge, Mass., USA) or R&D Systems (Minneapolis, Minn., USA). Further, methods for identification and design of ligands capable of binding specifically to Sortilin 1 are described, for example, in US Patent Application Publication No. 2011/1060439, content of which is incorporated herein by reference.

The cell, e.g. SMC, can be contacted with the inhibitor in a cell culture e.g., in vitro or ex vivo, or the inhibitor can be administrated to a subject, e.g., in vivo. In some embodiments, the inhibitor can be administrated to a subject to decrease, inhibit, prevent, reduce, and/or treat calcification. In some embodiments, the cell is an interstitial valvular cell. In some embodiments, the cell is an osteoblast. In some embodiments, the cell is an osteoclast. In some embodiments, the cell is a mesenchymal stem cell. In some embodiments, the cell is an endothelial cell. In some embodiments, the cell is a macrophage. In some embodiments, the cell is a monocyte. In some embodiments, the cell is a dendritic cell. In some embodiments, the cell is a lymphocyte.

The term "contacting" or "contact" as used herein in connection with contacting a cell includes subjecting the cells to an appropriate culture media, which comprises the indicated inhibitor. Where the cell is in vivo, "contacting" or "contact" includes administering the inhibitor in a pharmaceutical composition to a subject via an appropriate administration route such that the inhibitor contacts the cell in vivo.

As described herein, the inhibitors can be administered in a pharmaceutically acceptable carrier and can be delivered to the subject's cells in vivo and/or ex vivo by a variety of mechanisms well known in the art.

The term "ex vivo" refers to cells which are removed from a living organism and cultured outside the organism (e.g., in a test tube). If ex vivo methods are employed, cells or tissues can be removed and maintained outside the body according to standard protocols well known in the art. The compositions can be introduced into the cells via methods known or available to one of skill in the art. For example, the cells can be kept in a culture and inhibitor can be added to the culture media. The treated cells can then be infused (e.g., in a pharmaceutically acceptable carrier) or homotopically transplanted back into the subject per standard methods for the cell or tissue type. Standard methods are known for transplantation or infusion of various cells into a subject.

Generally, any amount of the compound can be contacted with the SMC. In some embodiments, compound is contacted at a concentration in the range of from about 0.1 nM to about 1000 mM. Preferably the compound is contacted in the range of from about 0.1 μM to about 10 μM.

Additionally, the compound can be contacted with the SMC for a sufficient time to allow the compound to be taken up by the SMC and interact with its target. For a non-limiting example, the compound can be contacted with the SMC at least 15 minutes before assaying for activity or amount of sortilin 1 or assaying for the amount or expression of the nucleic acid encoding sortilin 1.

For administration to a subject, the inhibitor can be formulated in pharmaceutically acceptable compositions which comprise the inhibitor formulated together with one or more pharmaceutically acceptable carriers (additives) and/or diluents. The inhibitors can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; (9) nasally; or (10) local administration (e.g., drug eluting stent, pluronic gel). Additionally, the inhibitors can be implanted into a patient or injected using a drug delivery composition. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) $C_2$-$C_{12}$ alcohols, such as ethanol; (26) lipid nanoparticles; and (27) other non-toxic compatible substances employed in pharmaceutical formulations. The carrier or excipient can include time delay material, such as glyceryl monostearate or glyceryl distearate alone or with a wax, or other materials well known in the art. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

The preparation of pharmaceutical compositions is well known in the art and has been described in many articles and textbooks, see e.g., Remington's Pharmaceutical Sciences, Gennaro A. R. ed., Mack Publishing Co., Easton, Pa., 1990, content of which of which is incorporated herein by reference in its entirety.

The pharmaceutical compositions can be made up in a solid form (including granules, powders or suppositories) or in a liquid form (e.g., solutions, suspensions, or emulsions). The pharmaceutical compositions can be subjected to conventional pharmaceutical operations such as sterilization and/or can contain conventional adjuvants, such as preservatives, stabilizers, wetting agents, emulsifiers, buffers etc.

Solid dosage forms for oral administration can include capsules, tablets, pills, powders, and granules. In such solid dosage forms, the active compound can be admixed with at least one inert diluent such as sucrose, lactose, or starch. Such dosage forms can also comprise, as in normal practice, additional substances other than inert diluents, e.g., lubricating agents such as magnesium stearate. In the case of capsules, tablets, and pills, the dosage forms can also comprise buffering agents. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting, sweetening, flavoring, and perfuming agents.

For purposes of parenteral administration, solutions in sesame or peanut oil or in aqueous propylene glycol can be employed, as well as sterile aqueous solutions of the corresponding water-soluble salts. Such aqueous solutions can be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art methods of preparing various pharmaceutical compositions with a certain amount of active ingredient are known, or will be apparent in light of this disclosure, to those skilled in this art.

The inhibitors can also be administered in controlled release formulations such as a slow release or a fast release formulation. Such controlled release formulations of the combination of this invention may be prepared using methods well known to those skilled in the art. The method of administration will be determined by the attendant physician or other person skilled in the art after an evaluation of the subject's conditions and requirements.

The amount of inhibitor that can be combined with a carrier material to produce a single dosage form will generally be that amount of the inhibitor that produces a therapeutic effect. Generally out of one hundred percent, this amount will range from about 0.01% to 99% of inhibitor. In some embodiment, amount of the inhibitor in the composition can be selected from the range from about 0.1% to about 99% (w/w), from about 1% to about 90% (w/w), from about 2% to about 80% (w/w), from about 5% to about 75% (w/w), from about 5% to about 50% (w/w), from about 10% (w/w) to about 60% (w/w), from about 0.01% to about 95% (w/v), from about 0.1% to about 90% (w/w), from about 1% to about 85% (w/w), from about 10% to about 50% (w/w), from about 1% to about 99% (w/w), from about 0.05% to about 99% (w/w), from about 0.1% to about 90% (w/w), from about 0.5% to about 85% (w/w), or from about 5% to about 80% (w/w) of the total composition.

In some embodiments, the composition comprises a therapeutically effective amount of the complex inhibitor for the treatment or prevention of cardiovascular calcification.

As used herein, the term "therapeutically effective amount" means an amount of the therapeutic agent which is effective to provide a desired outcome. Determination of a therapeutically effective amount is well within the capability of those skilled in the art. Generally, a therapeutically effective amount can vary with the subject's history, age, condition, sex, as well as the severity and type of the medical condition in the subject, and administration of other agents that inhibit pathological processes in neurodegenerative disorders.

Furthermore, therapeutically effective amounts will vary, as recognized by those skilled in the art, depending on the specific disease treated, the route of administration, the excipient selected, and the possibility of combination therapy. In some embodiments, the therapeutically effective amount can be in a range between the $ED_{50}$ and $LD_{50}$ (a dose of a therapeutic agent at which about 50% of subjects taking it are killed). In some embodiments, the therapeutically effective amount can be in a range between the $ED_{50}$ (a dose of a therapeutic agent at which a therapeutic effect is detected in at least about 50% of subjects taking it) and the $TD_{50}$ (a dose at which toxicity occurs at about 50% of the cases). Guidance regarding the efficacy and dosage which will deliver a therapeutically effective amount of a compound can be obtained from animal models of condition to be treated.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay. Examples of suitable bioassays include DNA replication assays, transcription based assays, and immunological assays.

The dosage can be determined by a physician and adjusted, as necessary, to suit observed effects of the treatment. Generally, the complex inhibitors are administered so that the inhibitor is given at a dose from 1 mg/kg to 150 mg/kg, 1 mg/kg to 100 mg/kg, 1 mg/kg to 50 mg/kg, 1 mg/kg to 20 mg/kg, 1 mg/kg to 10 mg/kg, 1 µg/kg to 1 mg/kg, 100 mg/kg to 100 mg/kg, 100 mg/kg to 50 mg/kg, 100 mg/kg to 20 mg/kg, 100 mg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like. For protein based inhibitors (such as antibodies) one preferred dosage is 0.1 mg/kg to 100 mg/kg of body weight (generally 10 mg/kg to 20 mg/kg).

As used herein, the term "administer" refers to the placement of a composition into a subject by a method or route which results in at least partial localization of the pharmaceutically active agent at a desired site. The inhibitors can be administered in any suitable manner. The manner of administration can be chosen based on, for example, whether local or systemic treatment is desired, and on the area to be treated. Accordingly, a composition can be administered by any appropriate route which results in effective treatment in the subject, i.e., administration results in delivery to a desired location in the subject where at least a portion of the pharmaceutically active agent is delivered. Exemplary modes of administration include, but are not limited to, implant, injection, infusion, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

In some embodiments, a composition described herein can be implanted in a subject. As used herein, the term "implanted," and grammatically related terms, refers to the positioning of the composition in a particular locus in the subject, either temporarily, semi-permanently, or permanently. The term does not require a permanent fixation of the composition in a particular position or location.

With respect to duration and frequency of administration or treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration once a month, once every two week, once a week, once every other day, daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, the inhibitor can be co-administered to the subject with in combination with a pharmaceutically active agent or therapeutic agent. Without limitations, the inhibitor can be administered before, concurrently, or after administration of the therapeutic agent. Thus, as used herein, the term "co-administer" refers to administration of two or more agents (e.g., the inhibitor and the pharmaceutically active agent) within a 24 hour period of each other, for example, as part of a clinical treatment regimen. In other embodiments, "co-administer" refers to administration within 12 hours, within 6 hours, within 5 hours, within 4 hours, within 3 hours, within 2 hours, within 1 hour, within 45, within 30 minutes, within 20, within 15 minutes, within 10 minutes, or within 5 minutes of each other. In other embodiments, "co-administer" refers to administration at the same time, either as part of a single formulation or as multiple formulations that are administered by the same or different routes. When the inhibitor and the pharmaceutically active agent are administered in different pharmaceutical compositions or at different times, routes of administration can be same or different.

Exemplary pharmaceutically active compound include, but are not limited to, those found in Harrison's Principles of Internal Medicine, 13$^{th}$ Edition, Eds. T. R. Harrison et al. McGraw-Hill N.Y., N.Y.; Physicians' Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's The Pharmacological Basis of Therapeutics; and current edition of The Merck Index, the complete contents of all of which are incorporated herein by reference.

In some embodiments, pharmaceutically active agent can include those agents known in the art for treating cardiovascular calcification, such as vitamin D sterols and/or RENAGEL®. Vitamin D sterols can include calcitriol, alfacalcidol, doxercalciferol, maxacalcitol or paricalcitol.

In some embodiments, pharmaceutically active agent can include calcimimetics, vitamins and their analogs, antibiotics, lanthanum carbonate, lipid-lowering agents, such as a statin (e.g. LIPITOR®), other modulators of lipid profile (e.g., HDL-raising drugs), anti-hypertensives, anti-inflammatory agents (steroidal and non-steroidal), inhibitors of pro-inflammatory cytokine (ENBRELOR®, KINERET®), and cardiovascular agents.

In some embodiments, pharmaceutically active agent includes those agents known in the art for treatment of inflammation or inflammation-associated disorders.

In some embodiments, pharmaceutically active agent can by a bisphosphonate (Alendronate, Risendronate, Ibandronate, Zoledronic acid).

In some embodiments, pharmaceutically active agent can by a hormone-related agent.

In some embodiments, the pharmaceutically active agent is an anti-inflammatory agent. Exemplary anti-inflammatory agents include, but are not limited to, non-steroidal anti-inflammatory drugs (NSAIDs—such as aspirin, ibuprofen, or naproxen, coricosteroids (such as presnisone), anti-malarial medication (such as hydrochloroquine), methotrexrate, sulfasalazine, leflunomide, anti-TNF medications, cyclophosphamise, mycophenolate, and inhibitors of pro-inflammatory signaling pathways.

In some embodiments, the pharmaceutically active agent is an immune response modulator. As used herein, the term "immune response modulator" refers to compound (e.g., a small-molecule, antibody, peptide, nucleic acid, or gene therapy reagent) that inhibits autoimmune response in a subject. Without wishing to be bound by theory, an immune response modulator inhibits the autoimmune response by inhibiting the activity, activation, or expression of inflammatory cytokines (e.g., IL-12, IL-23 or IL-27), or STAT-4. Exemplary immune response modulators include, but are not limited to, members of the group consisting of Lisofylline (LSF) and the LSF analogs and derivatives described in U.S. Pat. No. 6,774,130, contents of which are herein incorporated by reference in their entirety.

In some embodiments, the pharmaceutically active agent is an antibiotic agent. The term "antibiotic" is used herein to describe a compound or composition which decreases the viability of a microorganism, or which inhibits the growth or reproduction of a microorganism. As used in this disclosure, an antibiotic is further intended to include an antimicrobial, bacteriostatic, or bactericidal agent. Exemplary antibiotics include, but are not limited to, penicillin, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, and the like.

The dosage regimen for treating a disease condition with the combination therapy disclosed herein can be selected in accordance with a variety of factors, including the type, age, weight, sex and medical condition of the patient, the severity of the disease, the route of administration, and the particular compound employed, and thus can vary widely.

In some embodiments, the inhibitor can be administered in conjunction with surgical and non-surgical treatments. In some embodiments, the methods disclosed herein can be practiced in injunction with dialysis.

Vascular calcification, a well-recognized and common complication of CRD (also known as chronic kidney disease (CKD)), increases the risk of cardiovascular morbidity and mortality (Giachelli, C. J. Am. Soc. Nephrol. 15: 2959-64, 2004; Raggi, P. et al. J. Am. Coll. Cardiol. 39: 695-701, 2002). While the causes of vascular calcification in CKD remain to be elucidated, associated risk factors include age, gender, calcium and phosphate imbalance, increased serum phosphate levels, hypertension, time on dialysis, diabetes and glucose intolerance, obesity, dyslipidemia, and cigarette smoking (Zoccali C. Nephrol. Dial. Transplant 15: 454-7, 2000). These conventional risk factors, however, do not adequately explain the high mortality rates from cardiovascular causes in the patient population. Recent observations suggest that certain abnormalities in calcium and phosphorus metabolism, resulting in a raised serum calcium-phosphorus product contribute to the development of arterial/valvular calcification, and possibly to cardiovascular disease, in patients with end-stage renal disease (Goodman, W. et al. N. Engl. J. Med. 342: 1478-83, 2000; Guerin, A. et al. Nephrol. Dial. Transplant 15: 1014-21, 2000; Vattikuti, R. & Towler, D. Am. J. Physiol. Endocrinol. Metab. 286: E686-96, 2004). Clinical reports further suggest that elevated serum phosphate concentrations are associated with a substantially greater risk of end-stage CKD, and that risk increases up to 5-fold for each 1.0-mg/dL increment in the mean serum phosphate concentration (Mazhar, A R et al. Kidney Int 60: 324-332, 2001).

Another hallmark of advanced CKD is secondary hyperparathyroidism (HPT), characterized by elevated parathyroid hormone (PTH) levels and disordered mineral metabolism. The elevations in calcium, phosphorus, and Ca.times.P observed in patients with secondary HPT have been associated with an increased risk of vascular calcification (Chertow, G. et al. Kidney Int. 62: 245-52, 2002; Goodman, W. et al. N. Engl. J. Med. 342: 1478-83, 2000; Raggi, P. et al. J. Am. Coll. Cardiol. 39: 695-701, 2002). Commonly used therapeutic interventions for secondary HPT, such as calcium-based phosphate binders and doses of active vitamin D sterols can result in hypercalcemia and hyperphosphatemia (Chertow, G. et al. Kidney Int. 62: 245-52, 2002; Tan, A. et al. Kidney Int 51: 317-23, 1997; Gallieni, M. et al. Kidney Int 42: 1191-8, 1992), which are associated with the development or exacerbation of cardiovascular calcification.

Vascular calcification is an important and potentially serious complication of chronic renal failure. Two distinct patterns of vascular calcification have been identified (Proudfoot, D & Shanahan, C. Herz 26: 245-51, 2001), and it is common for both types to be present in uremic patients (Chen, N. & Moe, S. Semin Nephrol 24: 61-8, 2004). The medial calcification, occurs in the media of the vessel in conjunction with a phenotypic transition of SMCs into osteoblast-like cells, while atherogenesis, is associated with lipid-laden macrophages and intimal hyperplasia.

Medial wall calcification can develop in relatively young persons with chronic renal failure, and it is common in patients with diabetes mellitus even in the absence of renal disease. The presence of calcium in the medial wall of arteries distinguishes this type of vascular calcification from that associated with atherosclerosis (Schinke T. & Karsenty G. Nephrol Dial Transplant 15: 1272-4, 2000). Atherosclerotic vascular calcification occurs in atheromatous plaques along the intimal layer of arteries (Farzaneh-Far A. JAMA 284:1515-6, 2000). Calcification is usually greatest in large, well developed lesions, and it increases with age (Wexler L. et al. Circulation 94: 1175-92, 1996; Rumberger J. et al. Mayo Clin Proc 1999; 74: 243-52.). The extent of arterial calcification in patients with atherosclerosis generally corresponds to severity of disease. Unlike medial wall calcification, atherosclerotic vascular lesions, whether or not they contain calcium, impinge upon the arterial lumen and compromise blood flow. The localized deposition of calcium within atherosclerotic plaques may happen because of inflammation due to matrix vesicles release, apoptosis or oxidized lipids and other oxidative stresses and infiltration by monocytes and macrophages (Berliner J. et al. Circulation 91: 2488-96, 1995).

Some patients with end-stage renal disease develop a severe form of occlusive arterial disease called calciphylaxis or calcific uremic arteriolopathy. This syndrome is characterized by extensive calcium deposition in small arteries (Gipstein R. et al. Arch Intern Med 136: 1273-80, 1976; Richens G. et al. J Am Acad. Dermatol. 6: 537-9, 1982). In patients with this disease, arterial calcification and vascular occlusion lead to tissue ischemia and necrosis. Involvement of peripheral vessels can cause ulceration of the skin of the lower legs or gangrene of the digits of the feet or hands. Ischemia and necrosis of the skin and subcutaneous adipose tissue of the abdominal wall, thighs and/or buttocks are features of a proximal form of calcific uremic arteriolopathy (Budisavljevic M. et al. J Am Soc Nephrol. 7: 978-82, 1996; Ruggian J. et al. Am. J. Kidney Dis. 28: 409-14, 1996). This syndrome occurs more frequently in obese individuals, and women are affected more often than men for reasons that remain unclear (Goodman W. J. Nephrol. 15(6): S82-S85, 2002).

As used herein, the term "cardiovascular calcification" means formation, growth or deposition of extracellular matrix hydroxyapatite (calcium phosphate) crystal deposits in blood vessels. Cardiovascular calcification encompasses coronary, aortic, arterial, vein graft, tissue-engineered vessel, and other blood vessel calcification as well as aortic valve and mitral annulus calcification. The term includes atherosclerotic and medial wall calcification in vessels.

As used herein, the term "atherosclerotic calcification" means vascular calcification occurring in atheromatous plaques along the intimal layer of arteries.

Intimal calcification occurs within the perimeter of the internal elastic lamina as part of the atherosclerotic plaque and is often seen as discrete, punctate lesions on radiographs. It is associated with inflammatory cells, lipid, and vascular smooth muscle cells.

As used herein, the terms "medial calcification," "medial wall calcification," and "Monckeberg's sclerosis," mean calcification characterized by the presence of calcium in the medial wall of arteries.

Methods of detecting and measuring cardiovascular calcification are well known in the art. In one aspect, methods of measuring calcification include direct methods of detecting and measuring extent of calcium-phosphorus depositions in blood vessels.

In one aspect, direct methods of measuring cardiovascular calcification comprise in vivo imaging methods such as plain film roentgenography, coronary arteriography; fluoroscopy, including digital subtraction fluoroscopy; cinefluorography; conventional, helical, and electron beam computed tomography; intravascular ultrasound (IVUS); magnetic resonance imaging; and transthoracic and transesophageal echocardiography. Fluoroscopy and EBCT are most commonly used to detect calcification noninvasively, while cinefluorography and IVUS are used by coronary interventionalists to evaluate calcification in specific lesions before angioplasty. Transthoracic echocardiography is commonly used to detect aortic valve calcification.

In one aspect, cardiovascular calcification can be detected by plain film roentgenography. The advantage of this method is availability of the film and the low cost of the method, however, the disadvantage is its low sensitivity. Kelley M. & Newell J. Cardiol Clin. 1: 575-595, 1983.

In another aspect, fluoroscopy can be used to detect calcification in coronary arteries. Although fluoroscopy can detect moderate to large calcifications, its ability to identify small calcific deposits is low (Loecker et al. J Am Coll Cardiol. 19: 1167-1172, 1992). Fluoroscopy is widely available in both inpatient and outpatient settings and is relatively inexpensive, but it has several disadvantages. In addition to only a low to moderate sensitivity, fluoroscopic detection of calcium is dependent on the skill and experience of the operator as well as the number of views studied. Other important factors include variability of fluoroscopic equipment, the patient's body habitus, overlying anatomic structures, and overlying calcifications in structures such as vertebrae and valve annuli. With fluoroscopy, quantification of calcium is not possible, and film documentation is not commonly obtained.

In yet another aspect, cardiovascular calcification can be detected by conventional computed tomography (CT). Because calcium attenuates the x-ray beam, computed tomography (CT) is extremely sensitive in detecting cardiovascular calcification. While conventional CT appears to have better capability than fluoroscopy to detect coronary artery calcification, its limitations are slow scan times resulting in motion artifacts, volume averaging, breathing misregistration, and inability to quantify amount of plaque (Wexler et al. Circulation 94: 1175-1192, 1996). Aortic valve calcification is often detected by conventional CT, particularly in the elderly (Liu et al., American Journal of Roentgenology 186:342-349, 2006).

In a further aspect, calcification can be detected by helical or spiral computer tomography, which has considerably faster scan times than conventional CT. Overlapping sections also improve calcium detection. Shemesh et al. reported coronary calcium imaging by helical CT as having a sensitivity of 91% and a specificity of 52% when compared with angiographically significant coronary obstructive disease (Shemesh et al. Radiology 197: 779-783, 1995). However, other preliminary data have shown that even at these accelerated scan times, and especially with single helical CT, calcific deposits are blurred due to cardiac motion, and small calcifications may not be seen (Baskin et al. Circulation 92(suppl I): 1-651, 1995). Thus, helical CT remains superior to fluoroscopy and conventional CT in detecting calcification. Double-helix CT scanners appear to be more sensitive than single-helix scanners in detection of coronary calcification because of their higher resolution and thinner slice capabilities (Wexler et al. Circulation 94: 1175-1192, 1996)

In another aspect, Electron Beam Computed Tomography (EBCT) can be used for detection of cardiovascular calcification. EBCT uses an electron gun and a stationary tungsten "target" rather than a standard x-ray tube to generate x-rays, permitting very rapid scanning times. Originally referred to as cine or ultrafast CT, the term EBCT is now used to distinguish it from standard CT scans because modern spiral scanners are also achieving subsecond scanning times. For purposes of detecting coronary calcium, EBCT images are obtained in 100 ms with a scan slice thickness of 3 mm. Thirty to 40 adjacent axial scans are obtained by table incrementation. The scans, which are usually acquired during one or two separate breath-holding sequences, are triggered by the electrocardiographic signal at 80% of the RR interval, near the end of diastole and before atrial contraction, to minimize the effect of cardiac motion. The rapid image acquisition time virtually eliminates motion artifact related to cardiac contraction. The unopacified coronary arteries are easily identified by EBCT because the lower CT density of periarterial fat produces marked contrast to blood in the coronary arteries, while the mural calcium is evident because of its high CT density relative to blood. Additionally, the scanner software allows quantification of calcium area and density. An arbitrary scoring system has been devised based on the x-ray attenuation coefficient, or CT number measured in Hounsfield units, and the area of calcified deposits (Agatston et al. J Am Coll Cardiol. 15:827832, 1990). A screening study for coronary calcium can be completed within 10 or 15 minutes, requiring only a few seconds of scanning time. Electron beam CT scanners are more expensive than conventional or spiral CT scanners and are available in relatively fewer sites.

In one aspect, intravascular ultrasound (IVUS) can be used for detecting vascular calcification, in particular, coronary atherosclerosis (Waller et al. Circulation 85: 23052310, 1992). By using transducers with rotating reflectors mounted on the tips of catheters, it is possible to obtain cross-sectional images of the coronary arteries during cardiac catheterization. The sonograms provide information not only about the lumen of the artery but also about the thickness and tissue characteristics of the arterial wall. Calcification is seen as a hyperechoic area with shadowing: fibrotic noncalcified plaques are seen as hyperechoic areas without shadowing. (Honye et al. Trends Cardiovasc Med. 1: 305-311, 1991). The disadvantages in use of IVUS, as opposed to other imaging modalities, are that it is invasive and currently performed only in conjunction with selective coronary angiography, and it visualizes only a limited portion of the coronary tree. Although invasive, the technique is clinically important because it can show atherosclerotic involvement in patients with normal findings on coronary arteriograms and helps define the morphological characteristics of stenotic lesions before balloon angioplasty and selection of atherectomy devices (Tuzcu et al. J Am Coll Cardiol. 27: 832-838, 1996).

In another aspect, cardiovascular calcification can be measured by magnetic resonance imaging (MRI). However, the ability of MRI to detect coronary calcification is somewhat limited. Because microcalcifications do not substantially alter the signal intensity of voxels that contain a large amount of soft tissue, the net contrast in such calcium collections is low. Therefore, MRI detection of small quantities of calcification is difficult, and there are no reports or expected roles for MRI in detection of early coronary artery calcification or microcalcification (Wexler et al. Circulation 94: 1175-1192, 1996).

In another aspect, cardiovascular calcification can be measured by transthoracic (surface) echocardiography, which is particularly sensitive to detection of mitral and aortic valvular calcification; however, visualization of the coronary arteries has been documented only on rare occasions because of the limited available external acoustic windows. Transesophageal echocardiography is a widely available methodology that often can visualize the proximal coronary arteries (Koh et al. Int J Cardiol. 43: 202-206, 1994. Fernandes et al. Circulation 88: 2532-2540, 1993).

In another aspect, cardiovascular calcification can be assessed using near-infrared molecular imaging with a sensitive calcium binding molecular imaging agent using intravital fluorescence microscope or fluorescence reflectance imaging system (Aikawa E et al 116: 2841-2850, Circulation, 2007; Aikawa E et al, 119: 1785-1794; Circulation, 2009; New E P et al. 108; 1381-1391, Circ Res, 2011). However, while molecular imaging provides high-resolution images of microcalcification in arteries and valves, the system has been used only in animal studies.

In another aspect, cardiovascular calcification can be assessed in humans using 18F-Sodium Fluoride (18F-NaF) Positron Emission Tomography (PET) (George et al., J Am Coll Cardiol. 59:1549-50, 2012; Dweck et al., J Am Coll Cardiol. 59:1539-1548, 2012; Aikawa E, et al., Circulation 125:9-11, 2012; Dweck et al., Circulation 125:76-86, 2012).

In another aspect, vascular calcification can be assessed ex vivo by Von Kossa method. This method relies upon the principle that silver ions can be displaced from solution by carbonate or phosphate ions due to their respective positions in the electrochemical series. The argentaffin reaction is photochemical in nature and the activation energy is supplied from strong visible or ultra-violet light. Since the demonstrable forms of tissue carbonate or phosphate ions are invariably associated with calcium ions the method may be considered as demonstrating sites of tissue calcium deposition.

Other methods of direct measuring calcification may include, but are not limited to, immunofluorescent staining and densitometry. In another aspect, methods of assessing vascular calcification include methods of measuring determinants and/or risk factors of vascular calcification. Such factors include, but are not limited to, serum levels of phosphorus, calcium, and Ca×P product, parathyroid hormone (PTH), low-density lipoprotein cholesterol (LDL), high-density lipoprotein cholesterol (HDL), triglycerides, and creatinine. Methods of measuring these factors are well known in the art. Other methods of assessing vascular calcification include assessing factors of bone formation. Such factors include bone formation markers such as bone-specific alkaline phosphatase (BSAP), osteocalcin (OC), osteopontin (OPN), osteonectin (ON), sclerostin (SOST), dickkopf-1 (DKK1) carboxyterminal propeptide of type I collagen (PICP), and amino terminal propeptide of type I collagen (PINP); serum bone resorption markers such as cross-linked C-telopeptide of type I collagen (ICTP), tartrate-resistant acid phosphatase, TRACP and TRAP5B, N-telopeptide of collagen cross-links (NTx), and C-telopeptide of collagen cross-links (CTx); osteogenic transcription markers such as RUNX2/Cbfa1, Osterix, Msx-2, and urine bone resorption markers, such as hydroxyproline, free and total pyridinolines (Pyd), free and total deoxypyridinolines (Dpd), N-telopeptide of collagen cross-links (NTx), and C-telopeptide of collagen cross-links (CTx).

The work reported herein shows that exogenous sortilin 1 increases matrix mineralization and serum sortilin 1 levels are elevated in atherosclerotic mice. Accordingly, blood levels of sortilin 1 can be used a biomarker for severity of calcification or CRD. Thus, in one aspect provided herein is an assay for determining level or severity of calcification or CRD in a subject. The assay comprises: (a) subjecting a test sample of a subject to at least one analysis to determine the level of sortilin 1, wherein an increased level of sortilin 1 relative to a reference or control sample indicates that the subject has elevated calcification levels, at risk of developing calcification, has CRD, or is at risk of developing CRD. The level of sortilin 1 can be determined from the amount of sortilinl itself or a nucleic acid encoding sortilin 1.

The elevated or increased level of sortilin 1 can be at least 10% higher than a reference or control level. The Reference or control level can be sortilin 1 level in a healthy subject or a level determined previously from the same subject. For the avoidance of any doubt, the terms "increased" and "elevated" with reference to sortilin 1 level means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level or control level.

Collections of test samples for at least one analysis performed in the assays and/or methods described herein are well known to those skilled in the art. In some embodiments, a test sample subjected to analysis performed in the assays and/or methods described herein are derived from a biological sample of a subject. The term "biological sample" as used herein denotes a sample taken or isolated from a biological organism, e.g., cell lysate, a homogenate of a tissue sample from a subject or a fluid sample from a subject. The term "biological sample" also includes untreated or pre-treated (or pre-processed) biological samples. In some embodiments, the biological sample can be a biological fluid, including, but not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof. In other embodiments, the biological sample can include cell lysate and fractions thereof. For example, cells (such as red blood cells, platelets, white blood cells and any cells circulating in the biological fluid described herein) can be harvested and lysed to obtain a cell lysate. In some embodiments, the biological sample is blood, plasma, or serum.

A "biological sample" can contain cells from subject, but the term can also refer to non-cellular biological material, such as non-cellular fractions of blood, saliva, or urine, that can be used to measure sortilin 1 levels. In some embodiments, the sample is from a resection, biopsy, or core needle biopsy. In addition, fine needle aspirate samples can be used. Samples can be either paraffin-embedded or frozen tissue.

The biological sample can be a clinical sample. A "clinical sample" is a sample derived from a human subject. A biological sample can also be referred to as a "subject sample." A test biological sample is the biological sample that has been the object of analysis, monitoring, or observation. A control biological sample can be either a positive or a negative control for the test biological sample. Often, the control biological sample contains the same types of tissues, cells and biological fluids as that of the test biological sample. The sample can be obtained by removing a sample of cells from a subject, but can also be accomplished by using previously isolated cells (e.g. isolated by another person). In addition, the biological sample can be freshly collected or a previously collected sample.

In some embodiments, the test sample or the biological sample can be a frozen biological sample, e.g., a frozen tissue or fluid sample such as urine, blood, serum or plasma. The frozen sample can be thawed before employing methods, assays and systems of the invention. After thawing, a frozen sample can be centrifuged before being subjected to methods, assays and systems of the invention.

In some embodiments, a test sample or a biological sample can be a nucleic acid product amplified after polymerase chain reaction (PCR). The nucleic acid product of the instant invention include DNA, RNA and mRNA and can be isolated from a particular biological sample using any of a number of procedures, which are well-known in the art, the particular isolation procedure chosen being appropriate for the particular biological sample. Methods of isolating and analyzing nucleic acid variants as described above are well known to one skilled in the art and can be found, for example in the Molecular Cloning: A Laboratory Manual, 3rd Ed., Sambrook and Russel, Cold Spring Harbor Laboratory Press, 2001.

In some embodiments, the test sample or the biological sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. In addition, or alternatively, chemical and/or biological reagents can be employed to release nucleic acid or protein from the sample.

The skilled artisan is well aware of methods and processes appropriate for pre-processing of test or biological samples, e.g., blood, required for determination of sortilin 1 levels as described herein.

In some embodiments, the test sample or biological sample is a blood sample, e.g., whole blood, plasma, and serum. In some embodiments, the test sample or biological sample is a whole blood sample. In some embodiments, the test sample or biological sample is a serum sample. In some embodiments, the test sample or biological sample is a plasma sample. In some embodiments, the blood sample can be allowed to dry at room temperature from about 1 hour to overnight, or in the refrigerator (low humidity) for up to several months before subjected to analysis To collect a blood sample, by way of example only, the patient's blood can be drawn by trained medical personnel directly into anti-coagulants such as citrate, EDTA PGE, and theophylline. The whole blood can be separated into the plasma portion, the cells, and platelets portion by refrigerated centrifugation at 3500 g for 2 minutes. After centrifugation, the supernatant is the plasma and the pellet is RBC. Since platelets have a tendency to adhere to glass, it is preferred that the collection tube be siliconized. Another method of isolating red blood cells (RBCs) is described in Best, C A et al., 2003, J. Lipid Research, 44:612-620.

Alternatively, serum can be collected from the whole blood. By way of example, about 15 mL of whole blood can be drawn for about 6 mL of serum. The blood can be collected in a hard plastic or glass tube; blood will not clot in soft plastic. The whole blood is allowed to stand at room temperature for 30 minutes to 2 hours until a clot has formed. Then, clot can be carefully separated from the sides of the container using a glass rod or wooden applicator stick and the rest of the sample can be left overnight at 4° C. After which, the sample can be centrifuged, and the serum can be transferred into a clean tube. The serum can be clarified by centrifugation at 1000 g for 10 minutes at 4° C. The serum can be stored at −80° C. before analysis. In such embodiments, carotenoids may not be stable for long periods of time. Detailed described of obtaining serum using collection tubes can be found in U.S. Pat. No. 3,837,376 and is incorporated by reference. Blood collection tubes can also be purchased from BD Diagnostic Systems, Greiner Bio-One, and Kendall Company.

The whole blood can be first separated into platelet-rich plasma and cells (white and red blood cells). Platelet rich plasma (PRP) can be isolated from the blood centrifugation of citrated whole blood at 200 g for 20 minutes. The platelet rich plasma is then transferred to a fresh polyethylene tube. This PRP is then centrifuged at 800 g to pellet the platelets and the supernatant (platelet poor plasma [PPP]) can be saved for analysis, e.g., by ELISA, at a later stage. Platelets can be then gently re-suspended in a buffer such as Tyrodes buffer containing 1U/ml PGE2 and pelleted by centrifugation again. The wash can be repeated twice in this manner before removing the membrane fraction of platelets by centrifugation with Triton X, and lysing the pellet of platelet for platelet-derived PF4 analyses. Platelets can be lysed using 50 mM Tris HCL, 100-120 mM NaCl, 5 mM EDTA, 1% Igepal and Protease Inhibitor Tablet (complete TM mixture, Boehringer Manheim, Indianapolis, Ind.).

Methods of measuring the amount or presence of specific proteins and nucleic acids levels in biological samples are well known to one of skill in the art. For example, if the analyte is a protein, i.e., sortilin 1, the test sample can be subjected to at least one analysis selected from the group consisting of western blot, enzyme linked absorbance assay, mass spectrometry, immunoassay, flow cytometry, immunohistochemical analysis, and any combinations thereof. For example, a western blot, ELISA, immunoassay, flow cytometry, or immunohistochemical analysis can be performed using an anti-Sortilin 1 antibody. Exemplary anti-Sortilin 1 antibodies for using in the assay disclosed herein include, but are not limited to, NTR3 (E-9), NTR3 (G-11), NTR3 (C-19), NTR3 (F-15), NTR (H-300), and NTR3 (C-20), NTR3 (N-17) available from Santa Cruz Biotechnology; SORT1 purified MAxPab mouse polyclonal antibody, SORT 1 polyclonal antibody, SORT lmonoclonal antibody (M01, clone 1B3), and SORT 1 polyclonal antibody (A01) available from Abnova; Neurotensin Receptor 3 (NTR3, Sortilin, 100 kD NT Receptor, Glycoprotein 95, Gp95, NT3, OTTHUMP00000013784, Sortilin 1, Sortilin-1, SORT1) available from US Biological; Anti-Sortilin available from EMD Millipore; Human/Mouse Soritlin Mab (Clone 334708); Human Sortilin Affinity Purified Polyclonal Ab; and Human Sortilin Affinity Purified Polyclonal Ab available from R and Systems; Sortilin antibody available from Biorbyst; Sortilin 1 antibody [C1C3] available from GeneTex; Anti-SORT1/Sortilin available from LifeSpan BioSciences; SORT 1 available from Proteintech; Sortilin 1, Sortilin, Neurotensin Receptor 3 available from Thermo Scientific Pierce Products; monoclonal anti-SORT1 antibody produced in mouse and anti-SORT1 antibody produced in rabbit available from Sigma-Aldrich.

If the analyte is a nucleic acid, e.g., a nucleic acid encoding sortilin 1, the test sample can be subjected to at least one analysis selected from the group consisting of probe hybridization, primer extension, amplification, sequencing, 5' nuclease digestion, molecular beacon assay, DNA chip analysis, oligonucleotide ligation assay, size analysis, single-stranded conformation polymorphism, polymerase chain reaction (PCR), real-time quantitative PCR, and any combinations thereof. In one embodiment, PCD analysis can be performed using Hs00361747_ml TaqMan probes from Life Technologies. In some embodiments, the PCR analysis can be performed with a PCR primer pair having a first primer with a nucleotide sequence comprising at least 18 consecutive nucleotides of human SORT 1 (NCBI Reference Sequence: NM_002959.4 or NM_002959.5) and a second primer with a nucleotide sequence comprising a sequence complementary to at least at least 18 consecutive nucleotides of human SORT 1 (NCBI Reference Sequence: NM_002959.4 or NM_002959.5).

In some embodiments, the assay further comprises administering a therapy or an agent (e.g., a therapeutic agent) for reducing or inhibiting vascular calcification or treating a vascular calcification-related condition to the subject having an increased level of Sortilin 1 in the assay described herein. Agents and therapies useful for reducing or inhibiting calcification or treating vascular calcification-related conditions include, but are not limited to, statins, bisphosphonates, phosphate binders, mineralocorticoid receptor antagonists, and any combinations thereof. Some exemplary compositions and methods for reducing or inhibiting vascular calcification or treating vascular calcification-related conditions are described in PCT App. Publ. No. WO2000003677, No. WO2000033865, No. WO2001003774, No. WO2001070320, No. WO2002009683, No. WO2003013420, No. WO2004019923, No. WO2005044189, No. WO2006102061, No. WO2006122046, No. WO2007047969, No. WO2007112280, No. WO2008060139, No. WO2008115469, No. WO2008116215, No. WO2009017863, No. WO2009072132, No. WO2009102966, No. WO2010083613, No. WO2011005841, No. WO2011123518, No. WO2011133855, No. WO2012065059, No. WO2012100229 and No. WO2013006372; and U.S. Pat. No. 7,422,607, contents of all of which are incorporated herein by reference in their entireties. Anti-RANKL antibody, Anti-sclerostin antibody and anti-Wnt antibody are used for the treatment of the bone in preclinical studies. These antibodies could also be used in combination with sortilin 1 therapy.

Also provided herein is a composition or combination comprising an isolated sample obtained from a subject and a first reagent to react with sortilin 1. The sample can be a sample suspected of comprising an elevated level of sortilin 1. In some embodiments, the combination further comprises a second reagent that produces a signal in the presence of sortilin1 and the first reagent.

The first and second reagent can be selected independently from the group consisting of small organic or inorganic molecules; saccharines; oligosaccharides; polysaccharides; peptides; proteins; peptide analogs and derivatives; peptidomimetics; glycoproteins, glycopeptides; antibodies and antigen binding fragments thereof; nucleic acids; nucleic acid analogs and derivatives; lipids, an extract made from biological materials such as bacteria, plants, fungi, or animal cells; animal tissues; naturally occurring or synthetic compositions; and any combinations thereof. In some embodiments, the first reagent is a substrate that sortilin 1 acts on, a molecule that binds with sortilin 1, a molecule that inhibits binding of sortilin to a second molecule; and any combinations thereof.

In some embodiments, the first or the second reagent can comprise a label to produce a signal if sortilin 1 is present in the sample. Amount or level of the signal produced in the presence of sortilin can be correlated to amount or level of sortilin in the sample. Exemplary labels include, but are not limited to, radiolabels, chromophores, fluorophores, chemiluminescent precursors, chemiluminescent reactants, and the like.

The disclosure also provides a system comprising the composition/combination discussed above.

Computer systems for use in any aspects of the assay for determining sortilin 1 levels described herein are also provided. For example, one embodiment provided herein is a computer system for obtaining data from at least one test sample obtained from at least one subject. The system comprises: (a) a determination module configured to receive at least one test sample from the subject and perform at least one analysis on at least one test sample to determine the level or amount of sortilin 1 or a nucleic acid encoding sortiline 1; (b) a storage device configured to store data output from the determination module; and (c) a display module for displaying a content based in part on the data output from the determination module, wherein the content comprises a signal indicative of the amount or level of sortilin 1, and optionally the presence or absence of calcification or CRD.

In some embodiments, the determination module can further comprise a comparison module adapted to compare the data output from the determination module with reference data stored on the storage device.

In some embodiments, the storage device can be further configured to store information of at least one subject, for example, previously determined sortilin 1 level(s) of at least one subject.

In some embodiments, the content displayed on the display module can further comprises a signal indicative of whether the sortilin 1 level is at least 10% higher than a reference of control level.

In some embodiments, the content displayed on the display module can further comprise a signal indicative of the subject recommended to receive a treatment regimen for inhibiting calcification.

A computer readable medium having computer readable instructions recorded thereon to define software modules for implementing a method on a computer is also provided herein. In one embodiment, the computer readable storage medium comprises: (a) instructions for comparing the data stored on a storage device with reference data to provide a comparison result, wherein the comparison identifies elevated levels of sortilin 1; and (b) instructions for displaying a content based in part on the data output from the determination module, wherein the content comprises a signal indicative of elevated level of sortilin 1, and optionally the presence or absence of calcification or CRD.

In some embodiments, the computer readable medium can further comprise instructions to determine or calculate if the subject has a sortilin 1 level that is at least 10% higher than a reference or control level.

Exemplary embodiments of the invention can be described by any one of the following numbered paragraphs:
1. A method for inhibiting calcification of a smooth muscle cell (SMC), the method comprising contacting a compound with a SMC, wherein the compound inhibits: (i) activity or amount of sortilin 1 in a vascular smooth muscle cell or valvular interstitial cells; (ii) expression of a nucleic acid encoding sortilin 1 in a smooth muscle cell; or (iii) phosphorylation of sortilin 1.
2. The method of paragraph 1, the compound is selected from the group consisting of small organic or inorganic molecules; saccharines; oligosaccharides; polysaccharides; peptides; proteins; peptide analogs and derivatives; peptidomimetics; glycoproteins, glycopeptides; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.
3. The method of any of paragraphs 1-2, wherein the compound is a siRNA or an antibody.
4. The method of any of paragraphs 1-3, wherein the compound inhibits the expression of the nucleic acid encoding sortilin 1 by at least 10% relative to a control or reference level.
5. The method of any of paragraphs 1-4, wherein the compound inhibits the activity of sortilin 1 by at least 10% relative to a control or reference level.
6. The method of any of paragraphs 1-5, wherein the compound decreases the amount of sortilin 1 in the SMC by at least 10% relative to a control or reference level.
7. The method of any of paragraphs 1-6, wherein the compounds reduces tissue non-specific alkaline phosphatase activity (TNAP) by at least 10% relative to a control or reference level.
8. The method of any of paragraphs 1-7, wherein the compound increases phosphate regulating endopeptidase (PHEX) expression by at least 10% relative to a control or reference level.
9. The method of any of paragraphs 1-8, wherein the compound decreases matrix mineralization by at least 10% relative to a control or reference level.
10. The method of any of paragraphs 1-9, wherein the compound increases expression level of microRNA 125b by at least 10% relative to a control or reference level.
11. The method of any of paragraphs 1-10, wherein the compound decreases the association of sortilin 1 to non-specific alkaline phosphatase activity (TNAP), Caveolin-1.
12. The method of any of paragraphs 1-11, wherein the nucleic acid encoding sortilin 1 is mRNA.
13. The method of any of paragraphs 1-12, wherein said contacting is in vitro.
14. The method of any of paragraphs 1-13, wherein said contacting is in vivo.
15. The method of paragraph 14, wherein said contacting is in a mammal.
16. The method of paragraph 14 or 15, wherein said contacting is in a human.
17. The method of any of paragraphs 14-16, wherein said contacting is in a subject in need of inhibition of calcification.
18. The method of paragraph 17, wherein said calcification is cardiovascular calcification.
19. The method of paragraph 17 or 18, wherein said calcification is valvular or arterial calcification.
20. The method of any of paragraphs 17-19, wherein the severe renal failure, or has a transcatheter aortic valve implantation, or has chronic coronary atherosclerosis, or has aortic stenosis.
21. The method of any of paragraphs 17-20, wherein the subject has mineral imbalance or a calcium/phosphate disorder, including chronic renal disease, hemodialysis and type II diabetes; arterio-venous grafts/shunts; arterial and vein grafts; tissue engineered vascular and valvular implants; Paget's disease, rheumatoid arthritis, osteoporosis or osteoarthritis.
22. A method for inhibiting calcification or a clinical complication arising therefrom in a subject, the method comprising administering a therapeutically effective amount of a compound to a subject in need thereof, wherein the compound inhibits: (i) activity, phosphorylation, or amount of sortilin 1 in a SMC; (ii) expression of a nucleic acid encoding sortilin 1 in a SMC; or (iii) phosphorylation of sortilin 1.
23. The method of paragraph 22, wherein the compound is selected from the group consisting of small organic or inorganic molecules; saccharines; oligosaccharides; polysaccharides; peptides; proteins; peptide analogs and derivatives; peptidomimetics; glycoproteins, glycopeptides; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof.
24. The method of any of paragraphs 22-23, wherein the compound is a siRNA or an antibody.
25. The method of any of paragraphs 22-24, wherein the compound inhibits the expression of the nucleic acid encoding sortilin 1 by at least 10% relative to a control or reference level.
26. The method of any of paragraphs 22-25, wherein the compound inhibits the activity of sortilin 1 by at least 10% relative to a control or reference level.
27. The method of any of paragraphs 22-26, wherein the compound decreases the amount of sortilin 1 in the SMC by at least 10% relative to a control or reference level.
28. The method of any of paragraphs 22-27, wherein the compounds reduces tissue non-specific alkaline phosphatase activity by at least 10% relative to a control or reference level.
29. The method of any of paragraphs 22-28, wherein the compound increases phosphate regulating endopeptidase expression by at least 10% relative to a control or reference level.
30. The method of any of paragraphs 22-29, wherein the compound decreases matrix mineralization by at least 10% relative to a control or reference level.
31. The method of any of paragraphs 22-30, wherein the compound increases expression level of microRNA 125b by at least 10% relative to a control or reference level.
32. The method of any of paragraphs 22-31, wherein the compound decreases the association of sortilin 1 to non-specific alkaline phosphatase activity (TNAP), Caveolin-1.
33. The method of any of paragraphs 22-32 wherein the nucleic acid encoding sortilin 1 a mRNA.
34. The method of any of paragraphs 22-33, wherein said administering is implant, injection, infusion, instillation, implantation, or ingestion
35. The method of any of paragraphs 22-34, wherein the therapeutically effective amount is from about 1 ng/kg to about 150 mg/kg of body weight.
36. The method of any of paragraphs 22-35, wherein said administering is once a day.
37. The method of any of paragraphs 22-36, wherein the subject is a mammal.
38. The method of any of paragraphs 22-37, wherein said calcification is cardiovascular calcification.
39. The method of any of paragraphs 22-38, wherein said calcification is valvular or arterial calcification.
40. The method of any of paragraphs 22-39, wherein the subject has severe renal failure, or has a transcatheter aortic valve implantation, or has chronic coronary atherosclerosis, or has aortic stenosis.
41. The method of any of paragraphs 22-41, wherein the subject has mineral imbalance or a calcium/phosphate disorder, including chronic renal disease, hemodialysis and type II diabetes; arterio-venous grafts/shunts; arterial and vein grafts; tissue engineered vascular and valvular implants; Paget's disease, rheumatoid arthritis, osteoporosis or osteoarthritis.

42. The method of any of paragraphs 22-41, wherein the clinical complication is acute myocardial infraction, stroke, and the like.

43. The method of any of paragraphs 22-42, wherein the subject has an increased level of sortilin relative to a reference level.

44. A method comprising:
subjecting a biological sample from a subject to at least one analysis to detect level of sortilin 1 in the biological sample;
comparing the level of sortilin 1 in the sample to a reference level;
identifying the subject as having calcification or at risk of developing calcification if the level in the sample is higher than the reference level; and
administering a therapy for inhibiting or reducing calcification or for treating a vascular calcification-related condition such as CRD, diabetes, aortic valve stenosis, and some genetic disorders (e.g., Gaucher's disease).

45. The method of paragraph 44, wherein said therapy inhibits: (i) activity or amount of sortilin 1 in a SMC; (ii) expression of a nucleic acid encoding sortilin 1 in a SMC; or (iii) phosphorylation of sortilin 1.

46. An assay for determining calcification in a subject, the assay comprising subjecting a biological sample from a subject to at least one analysis to detect level of sortilin 1 in the biological sample, wherein an increased level of sortilin 1 relative to a reference level indicates the subject has calcification, is at risk of developing calcification, has chronic renal disease (CRD), or is at risk of developing CRD.

47. The assay of paragraph 46, wherein said at least one analysis is selected from the group consisting of western blot, enzyme linked absorbance assay, mass spectrometry, immunoassay, flow cytometry, immunohistochemical analysis, probe hybridization, primer extension, amplification, sequencing, 5' nuclease digestion, molecular beacon assay, DNA chip analysis, oligonucleotide ligation assay, size analysis, single-stranded conformation polymorphism, polymerase chain reaction (PCR), real-time quantitative PCR, and any combinations thereof.

48. The assay of paragraph 46 or 47, wherein the level of sortilin 1 is at least 10% higher than the reference or control level.

49. The assay of any of paragraphs 46-48, wherein the biological sample is a blood sample.

50. In combination, an isolated sample obtained from a subject, wherein the sample is suspected of comprising an elevated level of sortilin 1 and a reagent to react with sortilin 1.

51. The combination of paragraph 50, wherein the isolated sample is a blood sample.

52. The combination of paragraph 50 or 51, wherein the reagent is selected from the group consisting of small organic or inorganic molecules; saccharines; oligosaccharides; polysaccharides; peptides; proteins; peptide analogs and derivatives; peptidomimetics; glycoproteins, glycopeptides; antibodies and antigen binding fragments thereof; nucleic acids; nucleic acid analogs and derivatives; lipids, an extract made from biological materials such as bacteria, plants, fungi, or animal cells; animal tissues; naturally occurring or synthetic compositions; and any combinations thereof.

53. The combination of any of paragraphs 50-52, wherein the reagent is a substrate that sortilin 1 acts on, a molecule that binds with sortilin 1, a molecule that inhibits binding of sortilin to a second molecule; and any combinations thereof 54. The combination of any of paragraphs 50-53, wherein the reagent further comprises a label to produce a signal so as to detect the elevated level of the sortilin 1 in the isolated sample.

55. The combination of paragraph 54, wherein the label is any one or more of a radiolabel, a chromophore, a fluorophore, a chemiluminescent precursor, a chemiluminescent reactants, or a combination thereof.

56. The combination of any of paragraphs 50-55, wherein the elevated level is at least 10% higher than a control or reference level.

57. A system comprising:
(a) an isolated sample obtained from a subject, wherein the sample is suspected of comprising an elevated level of sortilin 1; and
(b) a reagent to react with sortilin 1.

58. The system of paragraph 57, wherein the isolated sample is a blood sample.

59. The system of paragraph 57 or 58, wherein the reagent is selected from the group consisting of small organic or inorganic molecules; saccharines; oligosaccharides; polysaccharides; peptides; proteins; peptide analogs and derivatives; peptidomimetics; glycoproteins, glycopeptides; antibodies and antigen binding fragments thereof; nucleic acids; nucleic acid analogs and derivatives; lipids, an extract made from biological materials such as bacteria, plants, fungi, or animal cells; animal tissues; naturally occurring or synthetic compositions; and any combinations thereof.

60. The system of any of paragraphs 57-59, wherein the reagent is a substrate that sortilin 1 acts on, a molecule that binds with sortilin 1, a molecule that inhibits binding of sortilin to a second molecule; and any combinations thereof.

61. The system of any of paragraphs 57-60, wherein the reagent further comprises a label to produce a signal so as to detect the elevated level of the sortilin 1 in the isolated sample.

62. The system of any of paragraphs 57-61, wherein the label is any one or more of a radiolabel, a chromophore, a fluorophore, a chemiluminescent precursor, a chemiluminescent reactants, or a combination thereof.

63. The system of any of paragraphs 57-62, wherein the elevated level is at least 10% higher than a control or reference level.

64. A computer system for obtaining data from at least one test sample obtained from at least one subject, the system comprising:
(a) a determination module configured to receive at least one test sample from the subject and perform at least one analysis on at least one test sample to determine the level or amount of sortilin 1 or a nucleic acid encoding sortiline 1;
(b) a storage device configured to store data output from the determination module; and
(c) a display module for displaying a content based in part on the data output from the determination module, wherein the content comprises a signal indicative of the amount or level of sortilin 1, and optionally the presence or absence of calcification or CRD.

65. A computer readable medium having computer readable instructions recorded thereon to define software modules for implementing a method on a computer, said computer readable storage medium comprising:

(a) instructions for comparing the data stored on a storage device with reference data to provide a comparison result, wherein the comparison identifies elevated levels of sortilin 1; and (b) instructions for displaying a content based in part on the data output from the determination module, wherein the content comprises a signal indicative of elevated level of sortilin 1, and optionally the presence or absence of calcification or CRD.

66. The method of any of paragraphs 1-21, wherein the compound decreases phosphorylation of sortilin 1.

67. The method of any of paragraphs 1-21 or 67, wherein said phosphorylation of sortilin 1 is at serine 819 or/and 825.

68. The method of any of paragraphs 22-43, wherein the compound decreases phosphorylation of sortilin 1.

69. The method of any of paragraphs 22-43 or 68, wherein said phosphorylation of sortilin 1 is at serine 819 or/and 825

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

As used interchangeably herein, the terms "essentially" and "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "essentially" means a proportion of at least about 90%, at least about 95%, at least about 98%, at least about 99% or more, or any integer between 90% and 100%. In some embodiments, the term "essentially" can include 100%.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviations (2SD) away from a reference level. The term refers to statistical evidence that there is a difference. It is defined as the probability of making a decision to reject the null hypothesis when the null hypothesis is actually true.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

As used herein, the term "subject" is intended to mean a human or other mammal, exhibiting, or at risk of developing, calcification. Such an individual can have, or be at risk of developing, for example, vascular calcification associated with conditions such as atherosclerosis, stenosis, restenosis, renal failure, diabetes, prosthesis implantation, tissue injury or age-related vascular disease. The prognostic and clinical indications of these conditions are known in the art. An individual treated by a method of the invention can have a systemic mineral imbalance associated with, for example, diabetes, chronic kidney disease, renal failure, kidney transplantation or kidney dialysis.

In some embodiments, a subject with mineral imbalance and calcium/phosphate disorders, including chronic renal disease, chronic renal failure, hemodyalysis, or diabetes suffers from accelerated vascular and valvular calcification. In these subjects, vascular grafts, including but not limited to arterio-venous grafts/shunts for hemodyalysis access, vein grafts for occlusive peripheral arterial disease, and saphenous vein bypass grafts for occlusive coronary arteries, are often occluded within a year. In addition, subjects with Paget's disease, rheumatoid arthritis, osteoporosis or osteoarthritis are also at risk for calcification. Without wishing to be bound by a theory, tissue engineered vascular and valvular implants in these patients at risk are expected to fail in a short period of time.

In some embodiments, the subject has severe renal failure or the subject has a transcatheter aortic valve. The renal failure can be on hemodialysis, hemodialysis AV shunts, vein grafts, vascular anastomsis, Paget's disease, or osteoarthritis. Without limitations, these disorders have hihg rates or acute calcific chages, which can make measuring the effect of the methods described herien easier.

The subject can be initially diagnosed by a licensed physician and/or authorized medical practitioner, and a regimen for prophylactic and/or therapeutic treatment via a method described herein can be suggested, recommended or prescribed. Thus, in some embodiments, the method comprises selecting a subject for treatment for cardiovascular calcification.

Animal models that are reliable indicators of human atherosclerosis, renal failure, hyperphosphatemia, diabetes, age-related vascular calcification and other conditions associated with cardiovascular calcification are known in the art. For example, an experimental model of calcification of the vessel wall is described by Yamaguchi et al., Exp. Path. 25: 185-190, 1984, content of which is incorporated herein by reference in its entirety.

By "treatment, prevention or amelioration" is meant delaying or preventing the onset of a disorder or reversing, alleviating, ameliorating, inhibiting, slowing down or stopping the progression, aggravation or deterioration the progression or severity of a condition. In some embodiments, at least one symptom is alleviated by at least 20%, at least 30%, at least 40%, at least 50%, at least 60%, at least 70%, at least 80%, at least 90%, or at least 95% but not 100%, i.e. not a complete alleviation. In some embodiments, at least one symptom is completely alleviated.

As used herein, the terms "inhibiting," "decreasing," "preventing," and "treating" in connection with cardiovascular calcification, are intended to mean preventing, retarding, or reversing formation, growth or deposition of extracellular matrix hydroxyapatite crystal deposits. Without limitations, the improvement in disorder severity includes the reversal of cardiovascular calcification, as well as slowing down the progression of vascular calcification.

As used herein, the terms "proteins" and "peptides" are used interchangeably herein to designate a series of amino acid residues connected to the other by peptide bonds between the alpha-amino and carboxy groups of adjacent residues. The terms "protein", and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

As used herein, the term "peptidomimetic" refers to a molecule that folds into or has a defined three-dimensional structure similar to a natural peptide.

The term "heavy chain" includes a full-length heavy chain and fragments thereof having sufficient variable region sequence to confer specificity to sortilin 1. A full-length heavy chain includes a variable region domain, VH, and three constant region domains, CH1, CH2, and CH3. The VH domain is at the amino-terminus of the polypeptide, and the CH3 domain is at the carboxyl-terminus.

The term "light chain" includes a full-length light chain and fragments thereof having sufficient variable region sequence to confer specificity to sortilin 1. A full-length light chain includes a variable region domain, VL, and a constant region domain, CL. Like the heavy chain, the variable region domain of the light chain is at the amino-terminus of the polypeptide.

A "Fab fragment" is comprised of one light chain and the CH1 and variable regions of one heavy chain. The heavy chain of a Fab molecule cannot form a disulfide bond with another heavy chain molecule.

A "Fab' fragment" contains one light chain and one heavy chain that contains more of the constant region, between the CH1 and CH2 domains, such that an interchain disulfide bond can be formed between two heavy chains to form a F(ab')2 molecule.

A "F(ab')$_2$ fragment" contains two light chains and two heavy chains containing a portion of the constant region between the CH1 and CH2 domains, such that an interchain disulfide bond is formed between two heavy chains.

The "Fv region" comprises the variable regions from both the heavy and light chains, but lacks the constant regions.

As used herein, the term "Complementarity Determining Regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. Nos. 4,946,778 and 5,260,203 (hereby incorporated by reference).

The expression "linear antibodies" refers to the antibodies described in Zapata et al., Protein Eng., 8(10):1057-1062 (1995). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The expression "single-chain Fv" or "scFv" antibody fragments, as used herein, is intended to mean antibody fragments that comprise the VH and VL domains of antibody, wherein these domains are present in a single polypeptide chain. Preferably, the Fv polypeptide further comprises a polypeptide linker between the VH and VL domains which enables the scFv to form the desired structure for antigen binding. (The Pharmacology of Monoclonal Antibodies, vol. 113, Rosenburg and Moore eds., Springer-Verlag, New York, pp. 269-315 (1994)).

The term "diabodies," as used herein, refers to small antibody fragments with two antigen-binding sites, which fragments comprise a heavy-chain variable domain (VH) Connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. (EP 404,097; WO 93/11161; Hollinger et ah, Proc. Natl. Acad. Sd. USA, P0:6444-6448 (1993)).

A "bivalent antibody" other than a "multispecific" or "multifunctional" antibody, in certain embodiments, is understood to comprise binding sites having identical antigenic specificity.

A "bispecific" or "bifunctional" antibody is a hybrid antibody having two different heavy/light chain pairs and two different binding sites. Bispecific antibodies may be produced by a variety of methods including, but not limited to, fusion of hybridomas or linking of Fab' fragments. See, e.g., Songsivilai & Lachmann (1990), Clin. Exp. Immunol. 79:315-321; Kostelny et al. (1992), J. Immunol. 148: 15471553.

As used herein, the term "humanized antibody" means an antibody in which at least a portion of non-human sequences are replaced with human sequences. Examples of how to make humanized antibodies can be found, for example, in U.S. Pat. Nos. 6,054,297; 5,886,152; and 5,877,293, content of all of which is incorporated herein by reference in its entirety.

As used herein, the term "chimeric antibody" means an antibody that contains one or more regions from a first antibody and one or more regions from at least one other antibody. The first antibody and the additional antibodies can be from the same or different species.

As used herein, the term "antigens" refers to a molecule or a portion of a molecule capable of being bound by a selective binding agent, such as an antibody, and additionally capable of being used in an animal to elicit the production of antibodies capable of binding to an epitope of that antigen. An antigen may have one or more epitopes. The term "antigen" can also refer to a molecule capable of being bound by an antibody.

As used herein, the term "polysaccharide" refers to macromolecular carbohydrates whose molecule consists of a large number of monosaccharide molecules which are joined to one another by glycosidic linkage. The term polysaccharide is also intended to embrace an oligosaccharide. The polysaccharide can be homopolysaccharides or heteropolysaccharides. Whereas the homopolysaccharides contain only one kind of unit, the heteropolysaccharides consist of monomer units of different kinds.

The term "antisense oligonucleotide" refers to single stranded DNA or RNA that is complementary to a chosen sequence. In the case of antisense RNA, they prevent protein translation of messenger RNA strands by binding to them. Antisense DNA can be used to target a specific, complementary (coding or non-coding) RNA. If binding takes places this DNA/RNA hybrid can be degraded by the enzyme RNase H. Antisense oligonucleotides are generally from to 30, from 15 to 35, or from 18 to 25 nucleotides in length.

The term "shRNA" as used herein refers to short hairpin RNA which functions as RNAi and/or siRNA species but differs in that shRNA species are double stranded hairpin-like structure for increased stability. The term "RNAi" as used herein refers to interfering RNA, or RNA interference molecules are nucleic acid molecules or analogues thereof for example RNA-based molecules that inhibit gene expression. RNAi refers to a means of selective post-transcriptional gene silencing. RNAi can result in the destruction of specific mRNA, or prevents the processing or translation of RNA, such as mRNA.

As used herein, the term "aptamer" means a single-stranded, partially single-stranded, partially double-stranded or double-stranded nucleotide sequence capable of specifically recognizing a selected non-oligonucleotide molecule or group of molecules. Accordingly, aptamers are nucleic acid or peptide molecules that bind to a particular molecule of interest with high affinity and specificity (Tuerk and Gold, Science 249:505 (1990); Ellington and Szostak, Nature 346:818 (1990)). DNA or RNA aptamers have been successfully produced which bind many different entities from large proteins to small organic molecules. See Eaton, Curr. Opin. Chem. Biol. 1:10-16 (1997), Famulok, Curr. Opin. Struct. Biol. 9:324-9(1999), and Hermann and Patel, Science 287:820-5 (2000). Aptamers can be RNA or DNA based. Methods for selecting aptamers for binding to a molecule are widely known in the art and easily accessible to one of ordinary skill in the art. Generally, aptamers are engineered through repeated rounds of in vitro selection or equivalently, SELEX (systematic evolution of ligands by exponential enrichment) to bind to various molecular targets such as small molecules, proteins, nucleic acids, and even cells, tissues and organisms. The aptamer can be prepared by any known method, including synthetic, recombinant, and purification methods, and can be used alone or in combination with other aptamers specific for the same target. Further, as described more fully herein, the term "aptamer" specifically includes "secondary aptamers" containing a consensus sequence derived from comparing two or more known aptamers to a given target. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and non-nucleotide residues, groups or bridges. In some embodiments, the aptamer recognizes the non-oligonucleotide molecule or group of molecules by a mechanism other than Watson-Crick base pairing or triplex formation.

As used herein, the term "ribozyme" means a single-stranded, partially single-stranded, partially double-stranded or double-stranded nucleotide sequence having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to up-regulate genes that are suppressed by the binding of a transcription factor. Examples of the utilization of decoy oligonucleotides can be found in Mann et al., J. Clin. Invest., 2000, 106: 1071-1075, content of which is incorporated herein by reference in its entirety.

As used herein, the term "calcimimetic compound" refers to a compound that binds to calcium sensing receptors and induces a conformational change that reduces the threshold for calcium sensing receptors activation by the endogenous ligand $Ca^{2+}$, thereby reducing parathyroid hormone (PTH) secretion. These calcimimetic compounds can also be considered allosteric modulators of the calcium receptors.

Exemplary calcimimetic compounds include, but are not limited to, those disclosed in, for example, European Patent No. 933 354 and 1 235 797; International Publication Nos. WO 01/34562, WO 93/04373, WO 94/18959, WO 95/11221, WO 96/12697, WO 97/41090; U.S. Pat. Nos. 5,688,938, 5,763,569, 5,962,314, 5,981,599, 6,001,884, 6,011,068, 6,031,003, 6,172,091, 6,211,244, 6,313,146, 6,342,532, 6,362,231, 6,432,656, 6,710,088, 6,908,935 and U.S. Patent Application Publication No. 2002/0107406, content of all of which is incorporated herein by reference in its entirety.

The term "fluorophore" used herein means a functional group and/or a molecule containing said functional group which will absorb energy of a specific wavelength and re-emit energy at a different wavelength. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Exemplary fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein (pH 10); 5-Carboxytetramethylrhodamine (5-TAMRA); 5-FAM (5-Carboxyfluorescein); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Anilin Blue; Anthrocyl stearate; APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAGTm FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); BG-647; Bimane; Bisbenzamide; Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Green-1 Ca2+ Dye; Calcium Green-2 Ca2+; Calcium Green-5N Ca2+; Calcium Green-C18 Ca2+; Calcium Orange; Calcofluor White; Carboxy-X-rhodamine (5-ROX); Cascade Blue™; Cascade Yellow; Catecholamine; CFDA; CFP—Cyan Fluorescent Protein; Chlorophyll; Chromomycin A; Chromomycin A; CMFDA; Coelenterazine; Coelenterazine cp; Coelenterazine f; Coelenterazine fcp; Coelenterazine h; Coelenterazine hcp; Coelenterazine ip; Coelenterazine O; Coumarin Phalloidin; CPM Methylcoumarin; CTC; Cy2™; Cy3.1 8; Cy3.5™; Cy3™; Cy5.1 8; Cy5.5™; Cy5™; Cy7™; Cyan GFP; cyclic AMP Fluorosensor (FiCRhR); d2; Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di-16-ASP); DIDS; Dihydorhodamine 123 (DHR); DiO (DiOC18(3)); DiR; DiR (DiIC18(7)); Dopamine; DsRed; DTAF; DY-630-NHS; DY-635-NHS; EBFP; ECFP; EGFP; ELF 97; Eosin; Erythrosin; Erythrosin ITC; Ethidium homodimer-1 (EthD-1); Euchrysin; Europium (III) chloride; Europium; EYFP; Fast Blue; FDA; Feulgen (Pararosaniline); FITC; FL-645; Flazo Orange; Fluo-3; Fluo-4; Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura-2, high calcium; Fura-2, low calcium; Genacryl Brilliant Red B; Genacryl Brilliant Yellow 10GF; Genacryl Pink 3G; Genacryl Yellow 5GF; GFP (S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indodicarbocyanine (DiD); Indotricarbocyanine (DiR); Intrawhite Cf; JC-1; JO-JO-1; JO-PRO-1; LaserPro; Laurodan; LDS 751; Leucophor PAF; Leucophor SF; Leucophor WS; Lissamine Rhodamine; Lissamine Rhodamine B; LOLO-1; LO-PRO-1; Lucifer Yellow; Mag Green; Magdala Red (Phloxin B); Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant Iavin EBG; Oregon Green™; Oregon Green 488-X; Oregon Green™ 488; Oregon Green™ 500; Oregon Green™ 514; Pacific Blue; Pararosaniline (Feulgen); PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26; PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B 540; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycoerythrin (PE); red shifted GFP (rsGFP, S65T); S65A; S65C; S65L; S65T; Sapphire GFP; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SPQ (6-methoxy-N-(3-sulfopropyl)-quinolinium); Stilbene; Sulphorhodamine B can C; Sulphorhodamine G Extra; Tetracycline; Tetramethylrhodamine; Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC (TetramethylRodamineIsoThioCyanate); True Blue; TruRed; Ultralite; Uranine B; Uvitex SFC; wt GFP; WW 781; XL665; X-Rhodamine; XRITC; Xylene Orange; Y66F; Y66H; Y66W; Yellow GFP; YFP; YO-PRO-1; YO-PRO-3; YOYO-1; and YOYO-3. Many suitable forms of these fluorescent compounds are available and can be used.

Other exemplary labels include radiolabels (e.g., $^3$H, $^{125}$I, $^{35}$S, $^{14}$C, or $^{32}$P), enzymes (e.g., galactosidases, glucorinidases, phosphatases (e.g., alkaline phosphatase), peroxidases (e.g., horseradish peroxidase), and cholinesterases), and calorimetric labels such as colloidal gold or colored glass or plastic (e.g., polystyrene, polypropylene, and latex) beads. Patents teaching the use of such labels include U.S. Pat. Nos. 3,817,837, 3,850,752, 3,939,350, 3,996,345, 4,277,437, 4,275,149, and 4,366,241, each of which is incorporated herein by reference in its entirety.

Means of detecting such labels are well known to those of skill in the art. Thus, for example, radiolabels can be detected using photographic film or scintillation counters, fluorescent markers can be detected using a photo-detector to detect emitted light. Enzymatic labels are typically detected by providing the enzyme with an enzyme substrate and detecting the reaction product produced by the action of the enzyme on the enzyme substrate, and calorimetric labels can be detected by visualizing the colored label.

The term "chromophore," as used herein, refers to a molecule which absorbs light of visible wavelengths, UV wavelengths or IR wavelengths.

A "radiolabel" is a product that has a radioactive substance, or radionuclide incorporated in it.

The term chemiluminescence, chemiluminescent and the like refers to the production of light by way of a chemical reaction. It can further be defined as the light emitted during the time that electronically excited products of chemical reactions return to the ground state.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1: Sortilin 1 is a Novel Inducer of Vascular Calcification

Vascular calcification is a prominent feature of chronic inflammatory disorders such as chronic renal disease (CRD), diabetes mellitus and atherosclerosis, which are associated with significant morbidity and mortality. Numerous clinical (Hyder et al., *American journal of epidemiology.* 2009; 169:186-194), histological (Liberman et al., *Arteriosclerosis, thrombosis, and vascular biology.* 2008; 28:463-470), and animal (Bucay et al., *Genes & development.* 1998; 12:1260-1268 and Okayasu et al., Okayasu et al. *The Journal of biological chemistry.* 2012; 287:19229-19241) studies suggest that processes in vascular calcification are similar to those of bone remodeling (Khosla S. *Nature medicine.* 2011; 17:430-431). Vascular calcification is an active, cell-regulated process in which vascular smooth muscle cells (SMCs) can lose the expression of their marker genes, acquire osteogenic markers, and deposit a mineralized bone-like matrix (Bostrom K I, Rajamannan N M, and Towler D A, *Circulation research.* 2011; 109:564-577). SMCs may play an important role in this process via transition toward an osteoblast-like state or release of calcifying matrix vesicles or apoptotic bodies. However the mechanisms of calcification remain largely unknown. Hence, a better understanding of molecular mechanisms of vascular calcification may lead to development of more efficient therapeutic strategies.

Genome wide association studies (GWAS) are powerful tools to identify novel genetic loci associated with cardiovascular disease. GWAS have strongly associated the 1p13 locus harbouring the SORT1 gene that encodes sortilin 1 with plasma low-density lipoprotein (LDL) cholesterol levels (Musunuru et al., *Nature.* 2010; 466:714-719), the onset of myocardial infarction (Kathiresan et al., *Nature genetics.* 2009; 41:334-341), and coronary artery calcification (O'Donnell et al., *Circulation.* 2011; 124:2855-2864). Sortilin 1 is a multi-ligand sorting receptor with functional characteristics of the vacular protein sorting 10 protein (Vps10p) domain family (Mazella et al., *The Journal of biological chemistry.* 1998; 273:26273-26276). The receptor is found in the trans-Golgi network or early endosomes and involved in Golgi-lysosome and plasma membrane-lysosome protein trafficking (Willnow T E, Petersen C M, and Nykjaer A. *Nature reviews. Neuroscience.* 2008; 9:899-909). Sortilin 1 is synthesized as a propeptide. The convertase-mediated cleavage in the late trans-Golgi activates its specialized tissue-specific ligand sorting roles (Munck et al., *The EMBO journal.* 1999; 18:595-604). Evidence suggests the binding of Sortilin 1 to lipoprotein lipases (Nielsen et al., *The Journal of biological chemistry.* 1999; 274:8832-8836), apolipoprotein (Apo) AV (Nilsson et al., *The Journal of biological chemistry.* 2008; 283:25920-2592), and ApoB100 (Musunuru et al., *Nature.* 2010; 466:714-719 and Kjolby et al., *Cell metabolism.* 2010; 12:213-223). Two recent studies reported the function of SORT1 in lipid metabolism. Musunuru et al. provided the evidence that high sortilin 1 levels are associated with reduced hepatic very low density lipoprotein (VLDL) secretion and lower LDL cholesterol level using a humanized mouse model with liver specific sortilin 1 deletion or overexpression (Musunuru et al., *Nature.* 2010; 466:714-719). In contrast, Kjolby et al. showed that the global absence of Sort1 reduces secretion of lipoproteins from the liver and ameliorates hypercholesterolemia and atherosclerosis in LDL receptor-deficient mice (Kjolby et al., *Cell metabolism.* 2010; 12:213-223). These contradictory findings releated to lipid metabolism remain a subject of debate.

Altough GWAS linked the SORT1 gene to coronary artery calcification, and genetic deletion of SORT1 in mice reduced atherosclerotic lesion formation, the role of sortilin 1 in processes of vascular calcification is utterly unknown. Data presented herein demonstrates for the first time that sortilin 1 contributes to the pathogenesis of vascular calcification.

Materials and Methods

Cell culture: Human coronary artery smooth muscle cells (HCASMCs) were purchased from Promocell (Heidelberg, Germany) and were grown in Smooth Muscle Cell Growth Medium 2 (SMC-GM2, Promocell) supplemented with epidermal growth factor (0.5 ng/ml), insulin (5 µg/ml), basic fibroblast growth factor-B (2 ng/ml) and fetal bovine serum (5%). The cells were maintained at 37° C. (5% CO2, 90% humidity) and were used between passages 3 and 8. Cells isolated from three to four independent donors were used.

Human tissue: Atherosclerotic carotid arteries (n=20) were obtained from patients undergoing endarterectomy surgery at Brigham and Women's Hospital according to IRB protocol. Samples were embedded in OCT compound and stored at −80 degree until use.

Animal procedure: 30-week-old Apoe−/− mice (Jackson Laboratory, Bar Harbor, Me., USA) consumed an atherogenic diet (D12079B; 41% milk fat, 0.2% total cholesterol, Research Diet, New Brunswick, N.J., USA) from 10 weeks of age. At 20 weeks of age, mice in each group were randomized either to continue with the atherogenic high-cholesterol diet or a CRD group. We used a two-step procedure to create CRD as previously described in Aikawa et al., *Circulation.* 2009; 119:1785-1794. Briefly, one week after a left hemi-nephrectomy a right total nephrectomy was performed. At 10 weeks after surgery, mice were sacrificed for correlative histological analyses. The Institutional Animal Care & Use Committee at Beth Israel Deaconess Medical Center approved all procedures (protocol #017-2010). Age-matched wild-type C57/BL6 mice (Jackson Laboratory) served as control.

Osteogenic transition of human vascular SMCs: SMCs were cultured for up to 21 days in the presence of either control medium (DMEM, 10% FBS, 1% antibiotics) or osteogenic medium, which consisted of control medium supplemented with 10 nmol/l dexamethasone, 10 mmol/l β-glycerol phosphate, and 100 mmol/l L-ascorbate phosphate. Medium was changed three times per week. Recombinant sortilin 1 (200 ng/ml; BioVendor, Candler, N.C., US) was replaced at every medium change.

RNA interference of sortilin 1: RNA silencing of sortilin 1 was performed as described previously in Goettsch et al., *Endocrinology.* 2011; 152:4915-4926. Briefly, 50 nmol/l siSORT1 (ONTARGETplus SMART-pool (L-010620), Thermo Scientific, Lafayette, Colo., USA) or non-targeting siRNA (ON-TARGET Non-Targeting Pool, Thermo Scientific) was transferred into SMCs using Dharmafect 1 (Dharmacon RNAi Technologies). Transfection was performed twice per week over the entire cell culture period.

Adenoviral overexpression of sortilinl: Human SORT1 (NM_002959.4) ORFEXPRESS™ Gateway® PLUS Shuttle Clone was purchased from GeneCopoeia (Rockville, Md., USA). The ViralPower Adenoviral Expression System together with pAd/CMV/V5-DEST as destination vector was used (Life Technologies, Grand Island, MY, USA). Recombination reaction between attL and attR sites was performed using LR Clonase II enzyme mix resulting in pAd/CMV/SORT1. pAd/CMV/V5-GW/lacZ was used as control vector. Adenovirus was amplified by transfection of PacI-digested vector in HEK293A cells according to the manufactures protocol. Multiplicity of infection (MOI) was determined by Adeno-X Rapid Titer Kit (Clontech, Mountain View, Calif., USA). SMCs were transduced with sortilin 1 and control (LacZ) adenoviruses at MOI of 100. For long term cell culture transduction was repeated every 7 days.

Cell viability: Cell viability was assessed using the Cell Titer Blue assay (Promega, Heidelberg, Germany) according to the manufacturer's protocol.

miRNA inhibition and induction: Inhibition and promotion of miRNA was performed as previously described in Goettsch et al., *The American journal of pathology.* 2011; 179:1594-1600. To inhibit the function of miR-125b, a miR inhibitor (antimiR-125b; Life Technologies) and a negative control (anti-negative control; Life Technologies) were used. A miR precursor (pre-miR-125b; Life Technologies) and a negative control (pre-negative control; Life Technologies) were used to promote the function of miR-125b. Transfection of 50 nmol/L RNAs was performed by lipofection using siPORT NeoFX Transfection Agent (Life Technologies).

3'-UTR luciferase binding assay: Human SORT1 (HmiT016537-MT01) and control (CmiT000001-MT01) 3'-UTR luciferase constructs were purchased from GeneCopoeia. Transient transfection of luciferase vector in SMCs was conducted using Fugene HD (Roche). In parallel, cells were transfected with 50 nmol/L miRNA precursor, inhibitor, or the corresponding controls as described in the method section. The luciferase signal was measured using Luc-Pair miR Luciferase assay (GeneCopoeia) 48 h after transfection. Firefly luciferase was normalized with Renilla luciferase in the same well.

Immunohistochemistry/Immunofluorescence: Cells were washed with PBS and fixed in 4% paraformaldehyde for 15 min. Cells were permeabilized for 10 min in 0.5% Triton X-100 and subsequently washed and blocked with 1% BSA in PBS for 30 min. The glass slides were exposed to anti-Sortilin 1 (1:100; BD, San Diego, Calif., USA) and anti-Osteopontin (OPN) (1:100; Abeam, Cambridge, Mass., USA) antibody for 2 hours and then incubated with an Alexa Fluor 488-labelled secondary antibody and Alexa Fluor 594-labelled secondary antibody (Life Technologies). After three washing steps, nuclear staining with DAPI was performed and slides were covered using a mounting medium (Dako, Glostrup, Denmark).

Tissue was cut into 7 µm-thin slices, and cryo-sections were fixed in acetone. After blocking in 4% of appropriate serum, sections were incubated with primary antibody [human SORT1 (1:100; BD) or mouse SORT1 (1:100; R&D systems, Minneapolis, Minn., USA)], followed by biotin-labelled secondary antibody (Vector Laboratories, Burlingame, Calif., USA) and streptavidin-coupled Alexa Fluor 488 antibody (Life Technologies). For immunofluorescence double labelling: after avidin/biotin blocking (Vector Laboratories), the second primary antibody [RUNX2 (Novus, Charles, Mo., USA) or OPN (Abeam)] were applied overnight at 4 degrees followed by biotin-labelled secondary antibody and streptavidin-coupled Alexa Fluor 594 antibody (Life Technologies). Sections were washed in PBS and embedded in mounting medium containing DAPI.

Bright field immunohistochemistry on tissue sections: after first biotin-labelled secondary antibody, tissue sections were incubated with streptavidin-labelled HRP solution (Dako) followed by AEC solution.

Slides were examined using the Eclipse 80i microscope (Nikon, Melville, VY) or the confocal microscope A1 (Nikon). All images were processed with the Elements 3.20 software (Nikon).

RNA preparation and real-time PCR: Total RNA from the cell culture was isolated using the TriZol (Life Technologies) and reverse transcription was performed using the QuantiTect Reverse Transcription Kit (Qiagen, Hilden, Germany). The mRNA expression was determined by TaqMan-based real-time PCR reactions (Life Technologies). The following TaqMan probes were used: Hs00361747_ml (human SORT1), Hs01011692_ml (human PHEX), Hs01047978_ml (human RUNX2), and 4326315E (human β-actin). The expression levels were normalized to β-actin. The results were calculated using the $\Delta\Delta Ct$ method, and presented in fold increases relative to control. Human Osteogenesis RT$^2$ Profiler™ PCR Array (Qiagen) was used to profiles the expression of 84 genes related to osteogenic differentiation.

Western blot analysis: Cells were lyzed with RIPA buffer containing protease inhibitor (Roche). Protein concentration was measured using BCA method (Thermo Scientific). Total protein was separated by 8-12% SDS-PAGE and transferred using the iBlot Western blotting system (Life Technologies). Primary antibodies against human SORT1 (1:1,000; Abcam or 1:200; BD), human PHEX (1:200; OriGene, Rockville, Md., USA) and human β-actin (1:5,000; Novus) were used. Protein expression was detected using Pierce ECL Western Blotting substrate Reagent (Thermo Scientific) and ImageQuant LAS 4000 (GE Healthcare, Waukesha, Wis., USA).

Mineralization assay and activity of tissue non-specific alkaline phosphatase: Mineralized matrix formation was assessed by Alizarin Red S staining. SMCs were fixed in 4% PFA and stained with 40 mM Alizarin Red S (pH 4.2) for 30 min at RT. Excess dye was removed by washing the plates with distilled water.

Accumulated calcium in the mineralized matrix was eluted using 0.6N hypochloric acid and determined using the Calcium Colorimetric Assay Kit (BioVision, Milpitas, Calif., USA). Tissue non-specific alkaline phosphatase (TNAP) activity was measured in cell cultures using the Alkaline Phosphatase Activity Colorimetric Assay Kit (BioVision).

Collagen Assay: Collagen content was determined in the extracellular matrix using Sircol Soluble Collagen Assay (Biocolor, Northern Ireland, UK). Briefly, after a washing step, cells were incubated with 0.5 M acetic acid/0.1 mg/ml pepsin overnight. After neutralization, collagen was concentrated overnight. The next day, Sircol reagent was added to bind collagen. After two washing steps the Sircol dye was released from the collagen-dye complex by alkali reagent and absorption at 555 nm was measured.

Measurement of serum sortilin 1 and FGF23: Serum sortilin 1 and FGF23 were measured by enzyme-linked immunosorbent assay (ELISA) according to the manufacturer's instructions. Serum sortilin 1 was analyzed using an immunoassay from Cusobio (Wuhan, China) and FGF23 was determined using an immunoassay from Millipore (Billerica, Mass., USA).

Co-immunoprecipitation: Cells were lyzed in immuno-precipitation (IP) lysis buffer (Thermo Scientific). Sortilin 1 antibody (5 µg, Abcam) or IgG rabbit control antibody (5 µg, Santa Cruz Biotechnology, Santa Cruz, Calif., USA) were incubated with Dynabeads Protein G (Life Technologies) by a two hour rotating incubation at 4 degrees followed by 3 times washing with PBS/Tween 20 (0.002%) using a magnet. One Ing of protein was pre-cleared by incubation with the bead-bound IgG antibody for one hour at 4 degrees under rotating conditions. Non-IgG-bound protein was divided and transferred to either bead-bound sortilin 1 antibody or bead-bound IgG antibody, and was incubated for four hours at 4 degrees under rotating conditions. Bead-antibody-protein complex was washed 3 tunes in 1,000 µl washing buffer (PBS). Ninety percent of the IPed protein sample was subjected to SDS-PAGE and visualized by coomassie stain (BioRad, Hercules, Calif., USA). The prominent band corresponding to the expected molecular weight for SORT1 (corroborated by a parallel Western blot analysis) was excised for in-gel trypsinization. The remaining gel lane for each co-IP condition was divided into 8 bands, and in-gel trypsinized. Peptides were dissolved in 20 µl sample loading buffer (0.1% formic acid, 5% acetonitrile) for subsequent mass spectrometric analysis.

Mass spectrometry: Peptide samples were analyzed with the high resolution/accuracy LTQ-Orbitrap (Elite model) mass spectrometer fronted with a Nanospray FLEX ion source, and coupled to an Easy-nLC1000 HPLC pump (Thermo Scientific). The peptides were subjected to a dual column set-up: an Acclaim PepMap RSLC C18 trap column, 75 µm×20 mm; and an Acclaim PepMap RSLC C18 analytical column 50 µm×150 mm (Thermo Scientific). The analytical gradient was run at 250 nl/min from 10 to 30% Solvent B (acetonitrile/0.1% formic acid) for 30 minutes, followed by five minutes of 95% Solvent B. Solvent A was 0.1% formic acid. All reagents were HPLC-grade. The instrument was set at 120 K resolution, and the top 20 precursor ions (within a scan range of 380-2000 m/z) were subjected to collision induced dissociation (collision energy 35%) for peptide sequencing (MS/MS). The dynamic exclusion feature was disabled.

Analysis of mass spectrometry data: The MS/MS data were queried against the Human UniProt database (downloaded on May 27, 2012) using the SEQUEST search algorithm (Yates et al., *Analytical chemistry*. 1995; 67: 1426-1436) via the Proteome Discoverer (PD) Package (Thermo Scientific) using methionine oxidation as a variable modification, and carbamidomethylation of cysteine residues as a fixed modification. The peptide false discovery rate (FDR) was calculated using Percolator provided by PD: the FDR was determined based on the number of MS/MS spectral hits when searched against the reverse, decoy Human database (Elias J E and Gygi S P, *Nature methods.* 2007; 4:207-214 and Kall et al., *Journal of proteome research.* 2008; 7:29-34). Peptides were filtered based on a 1% FDR, and proteins with three or more unique peptides were analyzed.

Sortilin 1-specific proteins were differentiated from non-specific proteins by subtracting the protein hits derived from IgG controls from those of the corresponding sortilin 1 IPs. The final co-IP lists include proteins that are completely absent in the IgG samples. For proteins that were present in both SORT1 and IgG IPs but may have been enriched due to SORT1 co-IP, only those with peptide-spectrum matches (PSMs) (Stevenson et al., *Journal of proteomics.* 2009; 72:555-566) 20-fold or greater (with respect to the IgG control) were included in the analysis. The PSM cut-off was established by the observed PSM counts of the myosin bands in FIG. 6A.

Statistical analysis: Data are given as means±SD, and n indicates the number of independent experiments. Statistical analyses were performed using a one-way ANOVA with Bonferroni's post hoc test, and single group comparisons using a Student's t test. Correlation analyses were performed according to Pearson. A value of $p<0.05$ was considered statistically significant.

Results and Discussion

Figure 1B:
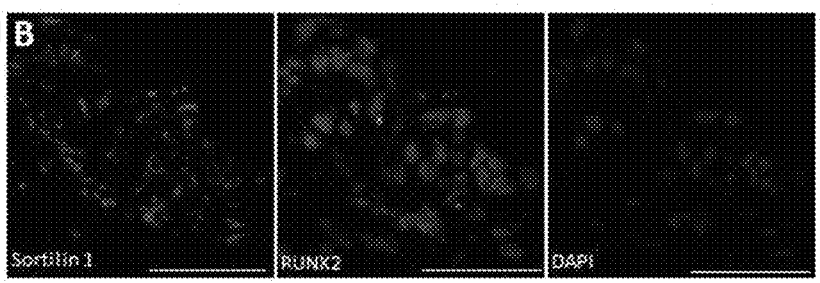

Sortilin 1 is expressed in human calcified lesions and induced during osteogenic transition of human vascular SMCs. Staining of calcified human carotid endarterectomy samples indicated a high expression of sortilin 1 in calcified regions (FIG. 1A). Cells in these areas showed a weak alpha smooth muscle actin (αSMA) staining and were negative for the macrophage marker CD68 (FIG. 1A). Due to the loss of SMC marker genes during osteogenesis, sections were stained for Runx2/Cbfa1, a marker of osteogenic transition. Indeed, in human calcified lesion, sortilin 1 was highly expressed in cells with activated, nucleus-located Runx2 (FIG. 1B).

Figure 1C:
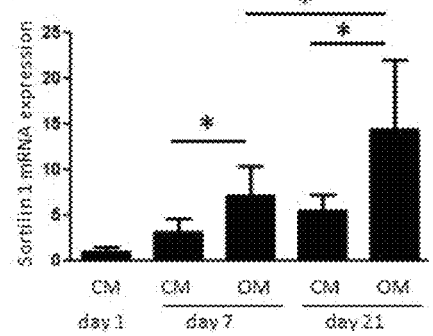
Figure 1D:
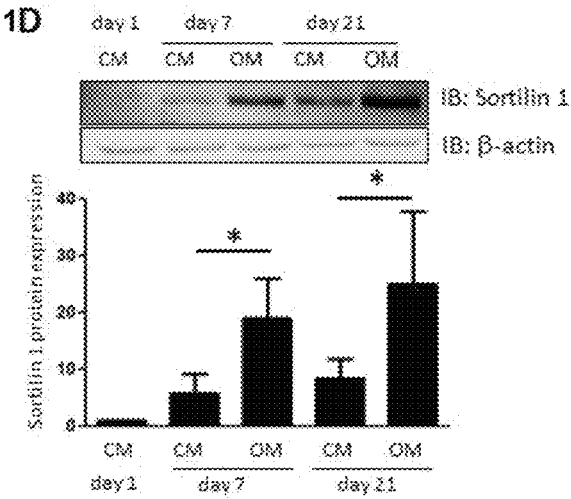
Figure 1E:
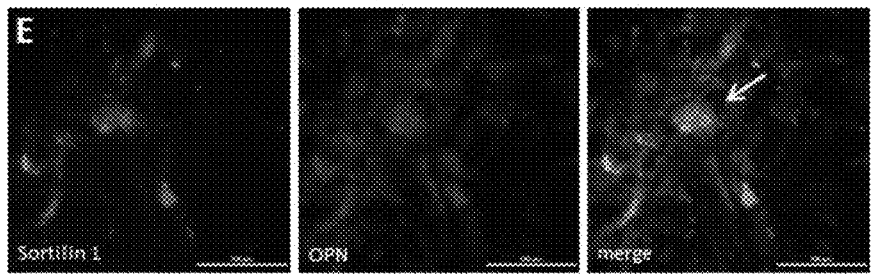

We subsequently investigated whether sortilin 1 expression is involved in the process of vessel calcification. Human coronary aortic SMCs (HCASMCs) cultured in osteogenic medium (OM) induced sortilin 1 expression in a time-dependent manner. Calcified SMCs (Day 21) showed 15-fold and 22-fold increases in sortilin 1 mRNA and protein expression, respectively, as compared to day 1, and a 2.5-fold induction compared to cells cultured for 21 day in control medium (FIGS. 1C and 1D). Immunofluorescence staining co-localized high sortilin 1 immunoreactivity with that of high osteopontin (OPN) immunoreactivity, an osteogenic marker for calcified SMCs (FIG. 1E).

Figure 7:
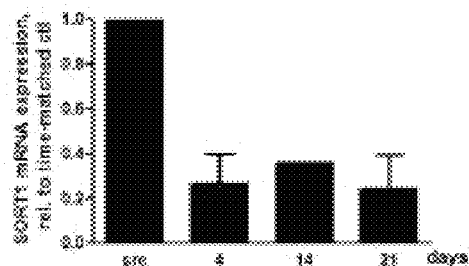
FIGS. 7A and 7B show establishment of sortilin 1 silencing. SMCs were cultured for 21 days in control medium (CM) and transfected twice per week during the entire cell culture period of 21 days with siRNA (siSORT1 or scramble control, Scr).
Figure 7:
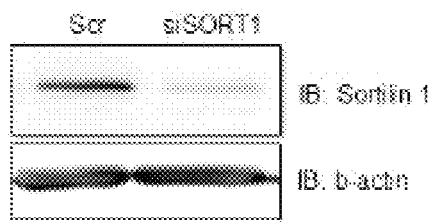
Figure 8:
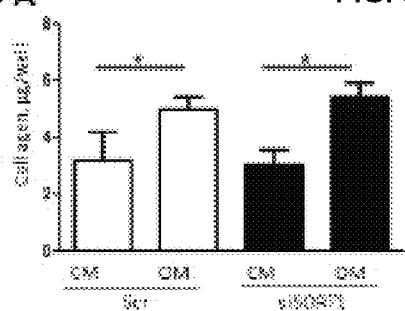
FIGS. 8A-8E SMCs were cultured for 21 days in control medium (CM) or osteogenic medium (OM) and transfected twice per week during the entire cell culture period of 21 days with siRNA (siSORT1 or scramble control, Scr) or cells were stimulated with recombinant sortilin 1 (rSORT1, 200 ng/ml).
Figure 8:
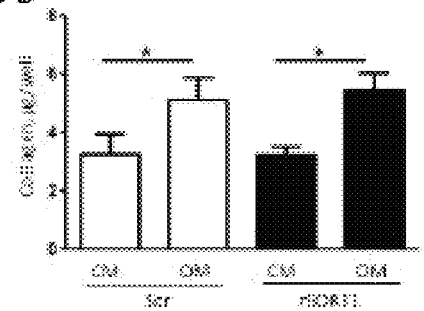
Figure 8:
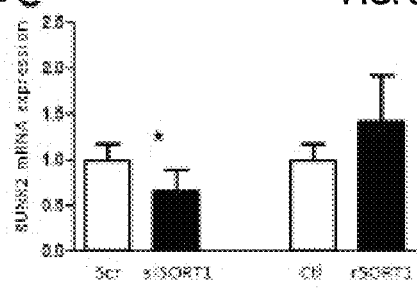
Figure 8:
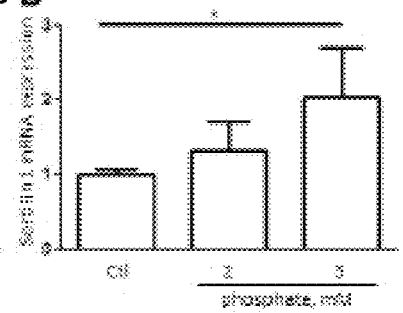
Figure 8:
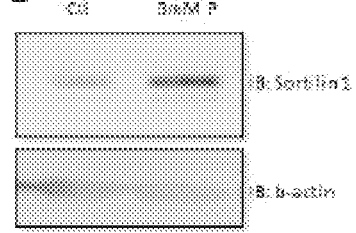

Sortilin 1 directly affects matrix mineralization of human vascular SMCs. To demonstrate the direct role of sortilin 1 in the calcification of SMC, we performed gain-of-function and loss of-of-function experiments. Long-term silencing of sortilin 1 by siRNA consistently suppressed sortilin 1 mRNA expression by 60-70% (FIG. 7A) and protein expression after 21 days (FIG. 7B).

Silencing of sortilin 1 caused a significant reduction of TNAP activity (−30%, p=0.009) in calcified SMCs (FIG. 2A), whereas increased exogenous sortilin 1 levels using recombinant sortilin 1 promoted TNAP activity by 37% (p=0.016, FIG. 2B). Moreover sortilin 1 silencing decreased nodule formation (FIG. 2C) demonstrated by a 33% reduction of the mineralized matrix (p=0.004, FIG. 2D). In contrast, elevated exogenous sortilin 1 level enhanced the matrix mineralization by 77% (p=0.002, FIG. 2E). These data were further supported by increasing endogenous sortilin 1 level using adenoviral overexpression. Infection of SMCs with adenoviral Sortilin 1 resulted in a 2-fold increase in TNAP activity (p=0.015, FIG. 2F) and enhanced matrix mineralization by 30% (p=0.028, FIG. 2G) compared to adenoviral LacZ control.

Of note, modulation of sortilin 1 had no effect on collagen accumulation and secretion. The matrix collagen content of calcified SMCs (FIGS. 10A and 10B) and released collagen (data not shown) did not alter upon sortilin 1 silencing or increased exogenous sortilin 1.

Collectively, these results demonstrate that sortilin 1 promotes matrix mineralization and TNAP activity in calcified human vascular SMCs.

Figure 3A:
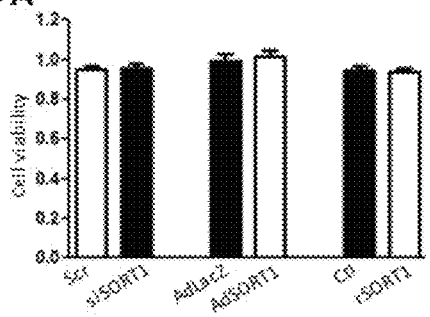
FIGS. 3A-3E show that Sortilin 1 regulates PHEX expression. SMCs were cultured for 21 days in control medium (CM), or osteogenic medium (OM). Sortilin 1 was either silenced by siRNA (siSORT1 or scramble control, Scr), overexpressed by adenovirus (AdSORT1 or AdLacZ) or cells were stimulated with recombinant sortilin 1 (rSORT1, 200 ng/ml) twice per week during the entire cell culture period.
Figure 3B:
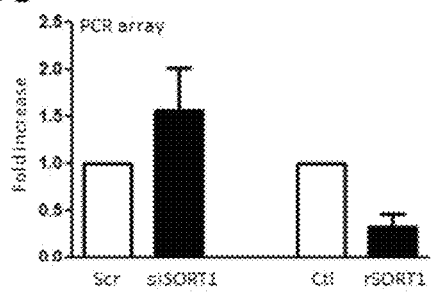
Figure 3C:
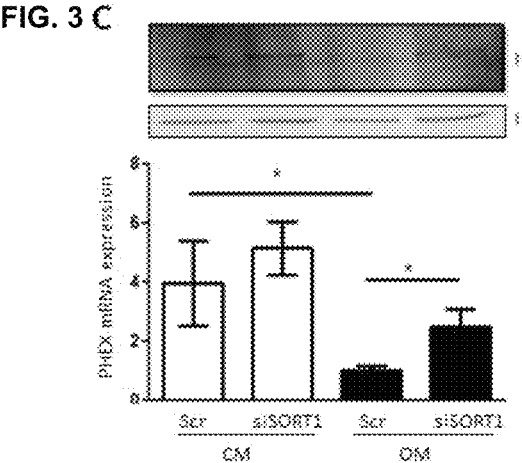
Figure 3D:
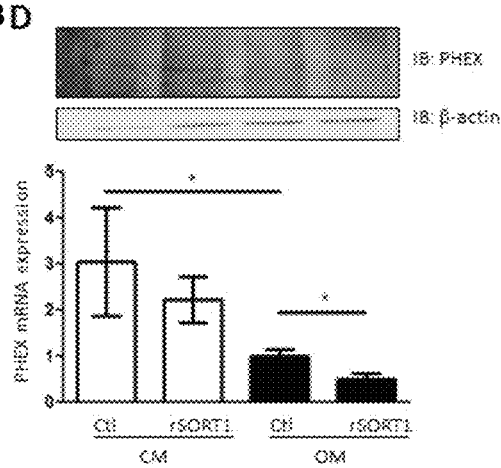
Figure 3E:
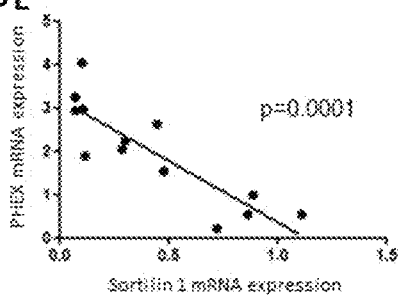

Sortilin 1 modulates PHEX in calcifying human vascular SMCs. We then investigated the mechanisms behind sortilin 1 action. First we analyzed cell viability, which was unaffected by sortilin 1 silencing, overexpression and stimulation (FIG. 3A). Unexpectedly, the main osteogenic transcription factor Runx2 was significantly repressed by sortilin 1 silencing, but was not affected by stimulation with sortilin 1 (FIG. 10C). Consequently, we analyzed the expression of 84 transcripts related to osteogenesis using a PCR array in calcified SMCs with either silenced sortilin 1 or stimulation with recombinant sortilin 1. We found that PHEX, a phosphate regulating endopeptidase, was 1.5-fold induced by sortilin 1 silencing. In contrast, PHEX expression decreased by 77% with increased exogenous sortilin 1 (FIG. 3B). We further validate these data using TaqMan real time PCR and Western blot analysis. PHEX expression was not affected by either the silencing or the recombinant expression of sortilin 1 in SMCs cultured in control medium (FIG. 3C). However, calcified SMCs showed strong inhibition of PHEX, which was significantly recovered after sortilin 1 silencing. Stimulation with sortilin 1 under calcifying condition decreased PHEX mRNA (FIG. 3D). The possible interplay between PHEX and sortilin 1 was further supported by a statistically significant negative correlation (r=−0.865; $R^2$=0.748; p=0.0001; FIG. 3E).

Figure 4A:
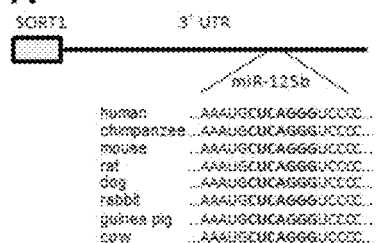
FIGS. 4A-4E show that miR125b regulates sortilin 1 by direct binding.
Figure 4B:
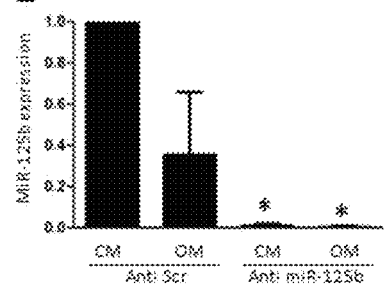
Figure 4C:
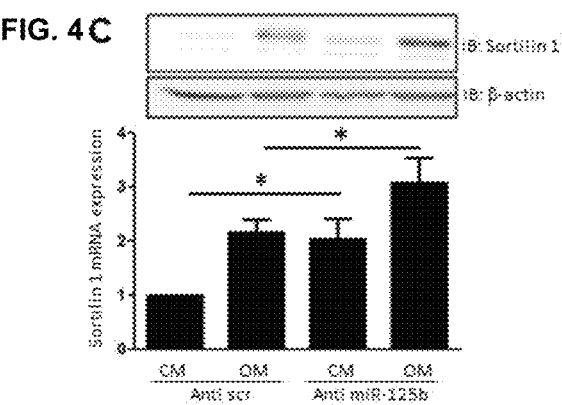

Sortilin 1 is repressed by miR-125b. We further examined what regulates sortilin 1 expression in the context of SMC calcification. Our previous studies demonstrated repression of miR-125b in calcified human vascular SMCs (Goettsch et al., *The American journal of pathology.* 2011; 179:1594-1600). In silico analyses using 3 different databases (targetscan.com, microRNA.org, pictar.mdc-berlin.de) revealed that miR-125b, a highly conserved miRNA, may suppress sortilin 1 expression by binding the 3'UTR (FIG. 4A). Treatment with osteogenic medium suppressed miR-125b expression (~60%) in SMCs (FIG. 4B), which is consistent with increased sortilin 1 expression levels as shown in FIGS. 1C and 1D. To determine the role of miR-125b in sortilin 1 expression, we then performed loss-of-function and gain-of-function experiments. Inhibition of miR-125b using anti-miR in the control medium caused a 2-fold increase in sortilin 1 expression (FIG. 4B), which was comparable to cells cultured in the osteogenic medium transfected with scramble anti-miR (FIG. 4C).

Figure 4D:
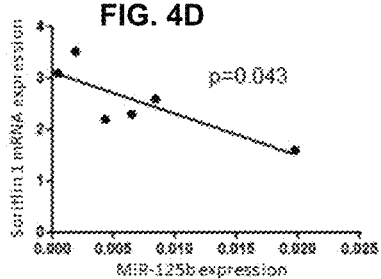
Figure 4E:
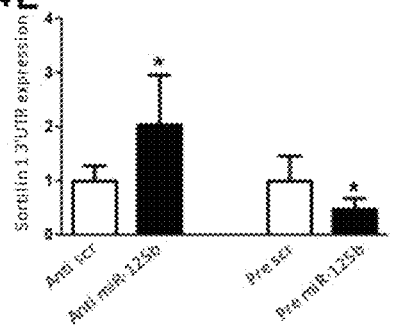

In addition, sortilin 1 and miR-125b expression levels negatively correlated in a statistically significant manner (r=−0.825; $R^2$=0.681; p=0.043; FIG. 4D), suggesting a direct interaction. A luciferase assay was then devised to determine the direct binding of miR-125b to the SORT1 3'UTR. Inhibition of miR-125b promoted SORT1 3'UTR reporter activity, whereas mimicking miR-125b repressed the activity (FIG. 4E). These lines of evidence indicate that binding of miR-125b to the 3'UTR of SORT1 indeed represses sortilin 1 expression, and suggest that the decreased expression of miR-125b in calcified SMCs contributes to the induction of sortilin 1 in vascular calcification.

Sortilin 1 is increased in chronic renal disease. We further assessed vascular expression of sortilin 1 in Apoe−/− mice fed a high fat diet and Apoe−/− mice with CRD, induced by 5/6 nephrectomy. Of note, CRD accelerates both intimal and medial calcification in Apoe−/− mouse model (Aikawa et al., Circulation. 2009; 119:1785-1794). In the aortic media of Apoe−/− mice, sortilin 1 immunopositive area was 46-fold greater as compared to wild type mice, and was further increased by 5/6 nephrectomy (6.6-fold, p=0.024) (FIGS. 5A-5C). In calcified intima, induction of CRD increased sortilin 1 immunopositive area by 3.6-fold (p=0.029; FIGS. 5B and 5D). These data were confirmed on mRNA level (rel. sortilin 1 mRNA expression: Apoe−/−; 0.19±0.08, CRD; 0.37±0.06; p=0.04) Sortilin 1 serum levels were elevated in Apoe−/− mice with and without CRD by 2.7 and 3.3-fold compared to wild type mice (p=0.008; FIG. 5E). Elevated serum phosphate levels, a typical feature of CRD, observed in our model (WT: 6.6±0.1 mg/dL; Apoe−/−: 20.5±1.2 mg/dL, CRD: 54.3±10.2 mg/dL, p<0.01), correlated with increased serum sortilin 1 (r=0.831, $R^2$=0.691, p=0.008, FIG. 5G). Furthermore, FGF23, a known regulator of phosphate homeostasis was 4-fold higher in serum of CRD mice as compared to wild type mice (FIG. 5F).

We further investigated whether high phosphate levels could trigger SORT1 activation. Stimulation of SMCs with phosphate increased sortilin 1 mRNA expression in a dose-dependent manner (FIG. 10). High phosphate level also promoted expression of sortilin 1 protein (FIG. 10).

Identification of key sortilin-1 interacting proteins: Sortilin 1-regulated calcification is in part dependent on PHEX, thus is it conceivable to propose that additional proteins act to either promote or inhibit sortilin 1 activity via direct physical associations. We therefore sought to investigate potential binding partners of sortilin 1 by performing co-immunoprecipitation (co-IP) of sortilin 1 from human vascular SMCs cultured in either control media or osteogenic/calcifying media, and by using high resolution mass spectrometry (MS) as the analytical method.

Figure 6A:
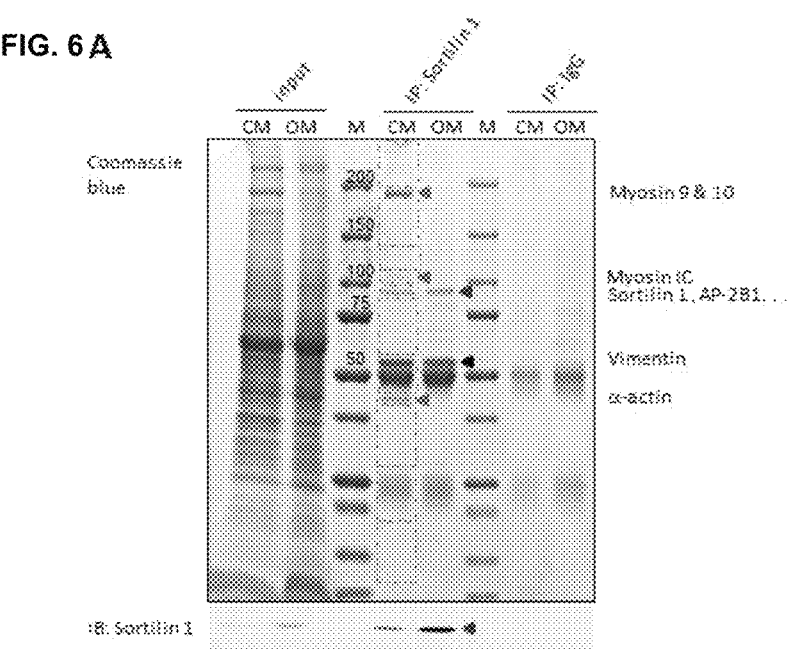
FIGS. 6A and 6B show results of Sortilin 1 co-immunoprecipitation study.
Figure 6B:
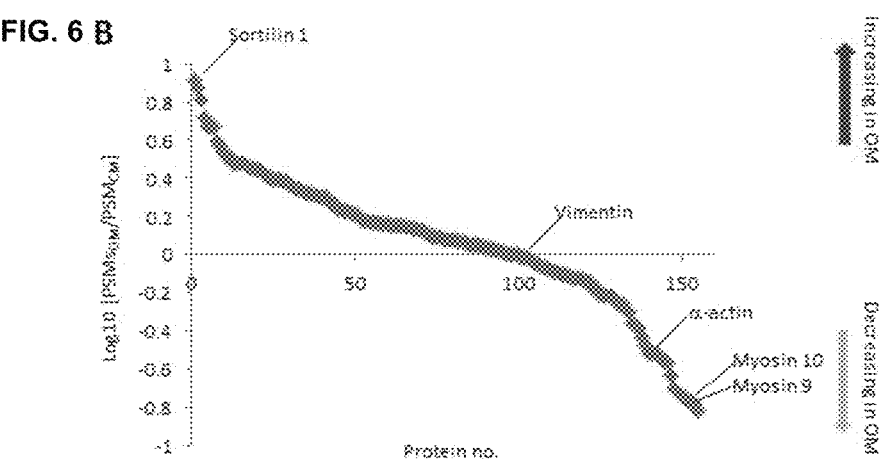

The Coomassie stained SDS-PAGE gel in FIG. 6A represents the sortilin 1 interactome from one out of three donor. We identified approximately 150 proteins that co-IP with sortilin 1 in both control and calcifying conditions (FIG. 6B), the prominent bands corresponded to sortilin 1, vimentin, myosin 9, myosin 10, and α-actin (FIG. 6A). A striking difference in the banding pattern between the control and calcifying conditions was the near disappearance of the myosins and α-actin (FIG. 6A, with green arrow heads). We used the peptide-spectral counting method (Stevenson et al., Journal of proteomics. 2009; 72:555-566) to compare the relative abundances of all 150+ proteins in control versus calcifying conditions. FIG. 6B demonstrates the correlation between the relative band intensities observed in the SDS-PAGE gel and immunoblot data, and the spectral count ratios of calcifying versus control conditions: sortilin 1 levels increase in calcified SMCs, whereas the myosins and α-actin decrease, and vimentin remains constant. Our ongoing analyses include analysis of sortilin 1 co-IPs from the same donor in high stringency conditions in order to differentiate between the stronger binding sortilin 1-core complex (high stringency) from those including peripheral binding proteins (low stringency). Ongoing analysis also includes co-IPs from additional donors. Thus far, our preliminary data implicate a number of protein trafficking interactors of sortilin 1, indicating that SMC calcification depends on subcellular reorganization of the sortilin 1 protein.

Sortilin 1 modulates PHEX in calcifying human vascular SMCs: To further proof the interplay between PHEX and sortilin 1, we performed loss-of-function studies. Silencing of PHEX did not block sortilin-1-dependent inhibition of SMC calcification (FIG. 9). In conclusion, the effect of sortilin 1 on PHEX expression does not directly involved in SMC calcification.

Sortilin 1 does not affect osteoblastogenesis in vitro: Vascular calcification and bone remodeling share common pathways. Therefore, a drug developed to treat or prevent vascular calcification should not affect bone remodeling. We analyzed the expression of sortilin 1 in osteoblasts differentiated from human mesenchymal stromal cells (hMSC), precursors of bone osteoblasts. Sortilin 1 protein expression does not increase during osteoblastogenesis (FIG. 10A). Furthermore, silencing of sortilin 1 or increasing of exogenous sortilin 1 does not alter alkaline phosphatase activity (FIG. 10B) and matrix mineralization (FIG. 10C) in human osteoblasts.

Extracellular vesicles contain sortilin 1: Based on our evidence that exogenous sortilin 1 increases matrix mineralization and serum sortilin 1 levels are elevated in atherosclerotic mice in our study, we also hypothesized that circulating sortilin 1 acts as a ligand for unknown cell-surface receptor or as a decoy receptor, which may trigger intracellular events leading to calcification. Indeed, shedding of luminal domain by zinc-metalloproteases and ADAM10 resulted in a soluble form of sortilin 1 (Navarro V, et al. Biochemical and biophysical research communications. 2002; 298:760-764).

In order to understand a from of circulating sortilin 1 (soluble vs vesicles), we analyzed cell culture supernatant as well as SMC-derived extracellular/matrix vesicles, which also contribute to the calcification process. We precipitated the protein from 2 ml cell culture supernatant and performed Western blot analysis. Using cell culture supernatent we detected sortilin 1 protein using adenovirus sortilin 1 overexpression (FIG. 11A). Cell culture supernatant from control or calcified cells and from LacZ control cells did not show sortilin 1 protein expression. Next, we isolated extracellular vesicles released from control or calcificed SMC into the cell culture supernatant and were able to detected sortilin 1 protein in extracellular vesicles from calcified SMC.

Identification of key sortilin-1 interacting proteins: We evaluated our proteomic data. FIG. 6B shows selected binding partners of sortilin 1, which are more or less or equally associated with sortilin 1 in calcified SMC.

Figure 14:
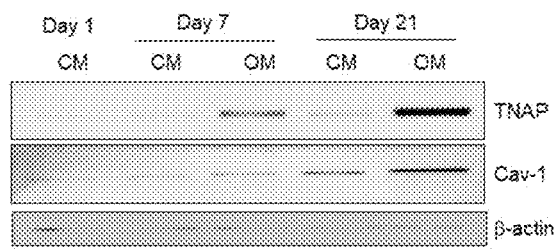
FIG. 14 shows that caveolin-1 is induced during osteogenic transition of human vascular SMCs. SMCs were cultured for 21 days in control medium (CM) or osteogenic medium (OM). Western blot at day 1, day 7, and day 21. b-actin served as loading control.
Figure 15:
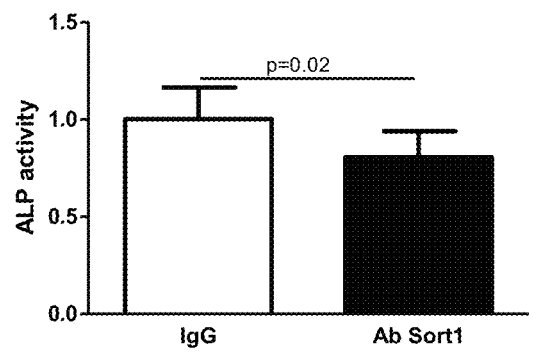
FIG. 15 shows that blocking antibody against sortilin 1 reduced alkaline phosphatase (ALP) activity. Calcifying smooth muscle cells (SMCs) were cultured in the presents of a sortilin 1 antibody (10 ug/ml, R&D systems) or the corresponding IgG control (10 ug/ml, R&D System) for 14 days. Blocking of sortilin 1 using an antibody against the extracellular domain significantly reduced ALP activity compared to IgG control (p=0.02, n=3).
Figure 16:
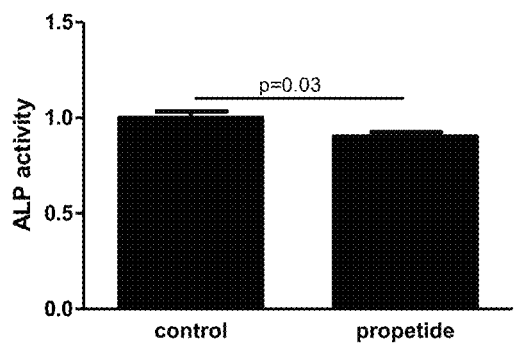
FIG. 16 shows sortilin 1 propetide reduced ALP activity. Calcifying SMCs were cultured in the presents of the sortilin 1 propeptide (200 ng/ml) for 14 days. Sortilin 1 propeptide significantly reduced ALP activity compared untreated control (p=0.03, n=3-4).

We confirmed the loss of association between sortilin 1 and myosin-9 using Western blot (FIG. 12). The association of sortilin 1 to caveolin-1 (Cav-1) and tissue non-specific alkaline phosphatase (TNAP) is promoted in calcified SMC (FIG. 13). Next, we examined whether Cav-1 is increased during the SMC calcification. Indeed caveolin-1 as well as TNAP were increased in calcified SMC (FIG. 14).

TABLE 1

Sortilin 1 binding partners from 3 independent experiments.

| Protein | 1 | 2 | 3 |
|---|---|---|---|
| Tropomyosin alpha-3 | NM | NM | NM |
| Actin, beta | 0.19* | NM | NM |
| Retinoic acid-induced 14 | NM | 0.29* | NM |

TABLE 1-continued

Sortilin 1 binding partners from 3 independent experiments.

| Protein | 1 | 2 | 3 |
| --- | --- | --- | --- |
| Actin-related protein 2/3 | 0.63 | NM | NM |
| Actin-related protein 3 | NM | — | NM |
| Alpha-actinin | NM | — | NM |
| PDZ and LIM domain protein 4 | NM | — | NM |
| Myosin-9 | 0.1* | 0.5* | 0.2* |
| Transitional endoplasmic reticulum ATPase | 0.5 | 1.1 | 1.2 |
| Caveolin-1 | 5.0* | 3.6* | OM |
| Sortilin 1 | 12.8* | 4.6* | 8.1* |
| V-type proton ATPase subunit C 1 | OM | OM | — |
| Guanine nucleotide-binding protein subunit beta-1 | OM | OM | — |
| Alkaline phophatase | OM | OM | — |
| Calpain-1 catalytic subunit | — | OM | OM |
| Cathepsin D | 0.65 | OM | OM |
| Erlin-1 | OM | OM | OM |

Ratio (calcified/control) of spectral counts.
NM; uniquely associated with sortilin 1 in control SMC,
OM; uniquely associated with sortilin 1 in calcified SMC,
—; not detected.

Sortilin 1 is loaded into matrix vesicles (MV). Recent studies identified that SMC-induced matrix mineralization may also proceed through the release of calcifying MVs. Indeed, we detected sortilin 1 in calcified MVs of human plaques using a transmission electron microscopy-based immunogold approach (FIG. 17A). Western blotting MV lysates isolated from supernatant of cells cultured in control or osteogenic medium detected sortilin 1 in calcified conditions (FIG. 17B). Mass spectrometry also verified the presence of sortilin 1 in MVs derived from both control and osteogenic conditions (FIGS. 17C and 17D). Sortilin 1 loading into MVs increased in sortilin 1 overexpressing SMCs and was further elevated in MVs derived from calcified SMCs as demonstrated by Western blot and mass spectrometry-based parameters such as the number of peptides and peptide-spectrum matches (PSMs) (FIG. 17D). We also determined that MV release is not dependent on sortilin 1 loading. The numbers of MVs released in control versus siRNA-targeted sortilin 1 SMCs were similar when analyzed by Nanosight nanoparticle tracking system (FIG. 17E).

Sortilin 1 re-distributes to lipid raft/caveolae-enriched membrane in calcified SMCs. Sortilin 1 is known to traffic within the cell. Recent studies suggest that lipid rafts play an essential role in regulated exocytosis pathway. To investigate if SMC calcification affects the cellular redistribution of sortilin 1, we performed a hydrodynamic method that uses discontinuous sucrose density gradients to resolve caveolae-enriched membrane/lipid rafts (CEM) from other cellular constituents not associated with CEM (nCEM). Under control conditions, we identified sortilin 1 in both CEM and nCEM fractions (FIG. 18A). We assayed these same fractions for caveolin-1 expression, which served as a positive control. Following SMC calcification, there was a redistribution of sortilin 1 into CEM fractions, suggesting an enrichment of sortilin 1 into specialized membrane domains upon SMC calcification (FIG. 18A). Calcified SMC showed increased caveolin-1 expression, which localizes in CEM (FIG. 18A) as well as caveolin-1 phosphorylation (Tyr-14) (FIG. 18B). Silencing of caveolin-1 reduced sortilin 1 protein levels in whole cell lysates from calcified SMCs (FIGS. 18B and 18C), as well as in the CEM (FIG. 18C). Furthermore, silencing of caveolin-1 reduced TNAP activity (−31%, p<0.001) and SMC calcification (−47%, p<0.001; FIGS. 18D and 18E). SMCs isolated from caveolin-1-deficient mice revealed abolished sortilin 1-mediated induction of TNAP and calcification (FIGS. 18F and 18G). We then investigated whether modulation of sortilin 1 affects the calcification potential of MVs. Silencing of cellular sortilin 1 reduced TNAP activity within the MVs (−45%; p<0.001) (FIG. 18H). Further, we detected caveolin-1 and TNAP in the MV as well, which were enriched in calcified SMCs (FIG. 17B).

Phosphorylation on $S_{825}$ and $S_{819}$ affect cellular ALP activity and matrix mineralization. We observed an increased phosphorylation of the C-terminal intracellular domain tail, SGYHDDpS825DEDLLE (SEQ ID NO: 10), of sortilin 1. The mutation of $S_{825}A$, $S_{825}D$, $S_{819}A$, $S_{819}D$ and the deletion of the C-terminal 6 amino acids were confirmed by sequencing. The functionality of the constructs were confirmed by Western blot. The goal was to identify the functional consequence of the C-terminal serine phosphorylation site.

Figure 19:
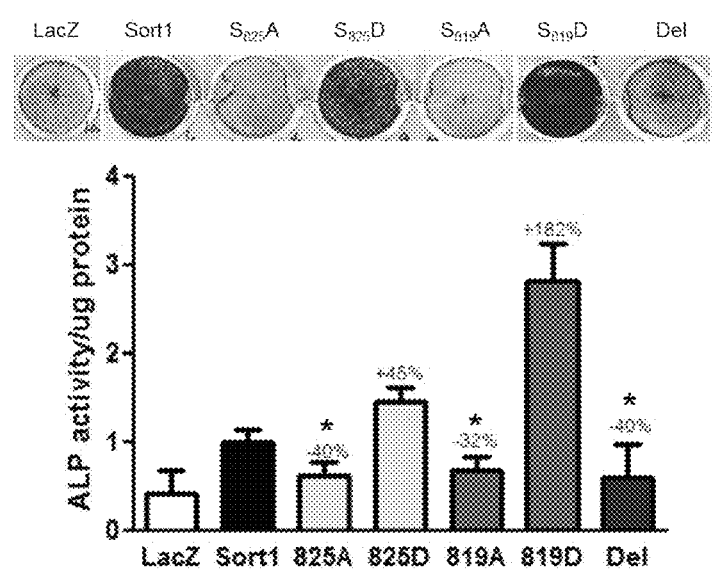
FIG. 19 shows that phosphorylation on $S_{825}$ and $S_{819}$ affect cellular ALP activity and matrix mineralization.

Overexpression of sortilin 1 promotes ALP activity by 2-fold. Prevention of the phosphorylation at $S_{825}$ and $S_{819}$ and the deletion of the C-terminal 6 amino acids significantly reduced ALP activity (p<0.05, n=3); whereas constitutive active phosphorylation of $S_{825}$ and $S_{819}$ promoted ALP activity 0.5 fold and 2.8 fold, respectively. In line with these findings, the sortilin 1-induced matrix mineralization was prevented by overexpression of $S_{825}$ and $S_{819}$ as well as by the deletion of the C-terminal 6 amino acids. Overexpression of the constitutive active $S_{819}$ phosphorylation further promoted matrix mineralization. Results are shown in FIG. 19.

The present study identified sortilin 1 as a novel contributor to cardiovascular calcification. Key findings documented here (1) revealed that high sortilin 1 expression co-localized with osteogenic markers in vitro and in vivo in human and mouse tissues and cells; (2) demonstrated an induction in serum sortilin 1 levels and an increase in sortilin 1 in aortic media in mouse CRD model; (3) determined miR-125b as a modulator of sortilin 1; and (4) provided mechanistic in vitro evidence for a direct role of sortilin 1 in osteogenic changes using gain-of-function and loss-of-function studies. In addition, we demonstrated in vitro that increased sortilin 1 levels promote vascular calcification via a PHEX-dependent mechanism, whereas decreased sortilin 1 levels prevent calcification. Moreover, the present study provides evidence that the sortilin 1 pathway is a novel mechanism of phosphate- and microRNA-dependent osteogenic transition of vascular SMCs towards an osteoblastic phenotype, in a manner independent of the Runx2 pathway.

Previously, the 1p13 locus harbouring the SORT1 gene, encoding sortilin 1 was associated with coronary artery disease (Samani et al., *The New England journal of medicine*. 2007; 357:443-453), particularly coronary artery calcification (O'Donnell et al., *Circulation*. 2011; 124:2855-2864). Thus, the present study may provide biological and molecular explanations for the observed link. Sortilin 1 promotes the calcification of SMCs. Our data are in line with the evidence associated with reduced atherosclerotic lesions in SORT1/LDL receptor double knockout mice (Kjolby et al., *Cell metabolism*. 2010; 12:213-223). Furthermore, non-vascular sortilin 1 expression was repressed in high-fat diet models of obesity in a lipoprotein-dependent manner (Ai et al., *The Journal of clinical investigation*. 2012; 122:1677-1687 and Kaddai et al., *Diabetologia*. 2009; 52:932-940). Using an animal model of CRD, we observed a strong increase in vascular sortilin 1 expression as well as elevated sortilin 1 serum levels. CRD is characterized by increased serum phosphate levels and no alterations in the lipid profile. Thus, the role of sortilin 1 in vascular calcification in CRD may be partially independent from hyperlipidaemia, and enhanced with phosphatemia. In our study, 5/6 nephrectomy significantly increased sortilin 1 expression in medial SMC in Apoe−/− mice offering a possible explanation for the observation that atherosclerotic plaques of patients with CRD and cardiovascular disease have intimal calcification, whereas medical calcification often occurred only in CRD patients (Nakamura et al., *Clinical journal of the American Society of Nephrology: CJASN.* 2009; 4:1892-1900). Furthermore, arterial medial calcification is highly correlated with serum phosphate levels (El-Abbadi et al., *Kidney international.* 2009; 75:1297-1307 and Ishimura et al., *American journal of kidney diseases: the official journal of the National Kidney Foundation.* 2005; 45:859-865). Indeed, we observed the induction of sortilin 1 by phosphate, which was further supported by a significant correlation of serum sortilin 1 and phosphate levels in the CRD mouse model. In addition, our study showed that sortilin 1 inhibits the phosphate-regulating endopeptidase PHEX in SMCs. The inactivating mutations of PHEX altered the responsiveness of bone cells to extracellular phosphate concentrations which may create a lower set point for "normal" phosphate levels (Ichikawa et al., *Journal of bone and mineral research: the official journal of the American Society for Bone and Mineral Research.* 2012; 27:453-460) and it stimulated FGF23 gene transcription (Liu et al., *American journal of physiology. Endocrinology and metabolism.* 2006; 291:E38-49 and Martin et al., *FASEB journal: official publication of the Federation of American Societies for Experimental Biology.* 2011; 25:2551-2562). In line with this evidence, we observed elevated FGF23 levels in parallel to increased sortilin 1 levels in CRD mice. Collectively, our results suggest that sortilin 1 participates in hyperphosphatemia-related vascular calcification involving the FGF23 pathway. In support to this notion, it was shown that increased serum FGF23 serum levels are associated with abdominal aortic calcification in men (Schoppet et al., *The Journal of clinical endocrinology and metabolism.* 2012; 97:E575-583) and vascular calcification in patients with CRD (Desjardins et al., *Osteoporosis international: a journal established as result of cooperation between the European Foundation for Osteoporosis and the National Osteoporosis Foundation of the USA.* 2012; 23:2017-2025).

It is well established that phosphate direct affects SMC calcification by stimulation of osteogenic/chondrogenic differentiation, matrix vesicles release, apoptosis, loss of inhibitors, and extracellular matrix degradation (Shanahan et al., *Circulation research.* 2011; 109:697-711). Sortilin 1 has been recognized as a crucial component of the signalling complex that controls survival of neurons (Jansen et al., *Nature neuroscience.* 2007; 10:1449-1457 and Vaegter et al., *Nature neuroscience.* 2011; 14:54-61). However, in the present study modulation of sortilin 1 did not affect cell viability. Evidence demonstrates that Sortilin 1 assists in sorting of target proteins in the secretory and/or the endosomal pathway. Sortilin 1 was shown to bind to lipoprotein lipase, and mediated endocytosis (Nielsen et al., *The Journal of biological chemistry.* 1999; 274:8832-8836); thus promoting osteogenesis and inhibiting adipogenesis of mesenchymal stem cells (Maeda et al., *Journal of cellular physiology.* 2002; 193:73-79). In addition, sortilin 1 has been identified to bind TGF-β family precursor proteins and promote their trafficking to the lysosome for degradation (Kwon et al., *The Journal of biological chemistry.* 2011; 286:21876-21885). TGF-β plays a crucial role in bone matrix production by a high-phosphate environment. Thus, it is reasonable to propose that sortilin 1 binds, sorts and degrade triggering molecules, including calcification inhibitors, and thereby promote vascular calcification.

Without wishing to be bound by a theory, based on our evidence that exogenous sortilin 1 increases matrix mineralization and serum sortilin 1 levels are elevated in atherosclerotic mice in our study, circulating sortilin 1 acts as a ligand for unknown cell-surface receptor or as a decoy receptor, which can trigger intracellular events leading to calcification. Indeed, shedding of luminal domain by zinc-metalloproteases and ADAM10 resulted in a soluble form of sortilin 1 (Navarro et al., *Biochemical and biophysical research communications.* 2002; 298:760-764). Hence, neutralizing antibodies can be used to interfere the sortilin 1-mediated pro-calcific pathway. However, while we found increased levels of sortilin 1 in mouse and human blood, no publication has previously demonstrated soluble sortilin 1 levels in human blood.

MiRNAs have been identified to play key roles in cardiovascular diseases (Creemers et al., *Circulation research.* 2012; 110:483-495). Previously, we demonstrated a role of miR-125b in osteogenic transition of SMCs. In the current study, we found that miR-125b has a binding site at the 3' end of SORT1. Indeed, miR-125b directly binds to sortilin 1, as demonstrated in the present study. Decreased expression of miR-125b in calcified SMCs (Goettsch et al., *The American journal of pathology.* 2011; 179:1594-1600) increased sortilin 1. Our study thus identified miR-125b as a suppressor for sortilin 1 expression.

Our current investigations into the sortilin 1 co-IP proteome aims to not only characterize further binding partners of sortilin 1, but also to differentiate between activity-dependent partners and those which are direct targets for subcellular trafficking, in the context of SMC calcification. Our data demonstrates a role for subcellular trafficking in sortilin 1-dependent calcification events. Given that we have access to state-of-the-art mass spectrometry strategies, we are enabled with not only identification based methods, but also a suite of quantitative methods to conduct in-depth biochemical studies on sortilin 1. Such MS workflows can determine, for example, absolute levels of circulating sortilin 1[42,43]; the relative stoichiometries of sortilin 1 binding partners/substrates (Singh et al., *Journal of proteome research.* 2009; 8:2201-2210), and even quantitative mapping of potential calcification-dependent post-translational events on sortilin 1 (Singh et al., Flexiqinase, a mass spectrometry-based assay, to unveil multikinase mechanisms. *Nature methods.* 2012; 9:504-508).

In conclusion, our findings demonstrate a novel mechanism that accelerates cardiovascular calcification in CRD via interaction of miR-125b and SORT1, as illustrated in FIG. 6. Our experiments have unravelled the role of sortilin 1 as a novel regulator of hyperphosphatemia-triggered osteogenic vascular SMC transition and calcification, proving its role as a therapeutic target.

In calcified regions of human atherosclerotic plaques, cells co-expressed sortilin 1 and activated Runx2, a regulator of osteoblast differentiation. In human SMCs osteogenic phosphate-rich media induced an osteoblast-like phenotype, coinciding with a 22-fold increased expression of sortilin 1 mRNA/protein. Silencing of sortilin 1 by siRNA significantly reduced alkaline phosphatase activity (TNAP) (30%) and matrix mineralization (33%) in calcified SMCs. In contrast, increased endogenous or exogenous sortilin 1 promoted TNAP activity by 37% and matrix mineralization by up to 77%. PCR array revealed a significant inverse correlation between phosphate-regulating endopeptidase (PHEX) and sortilin 1. Sortilin 1 siRNA induced PHEX by 1.5-fold, whereas increased sortilin 1 diminished PHEX expression by 77%. In silico analysis suggested that sortilin 1 is a target for microRNA-125b. We verified miR-125b indeed binds to 3'UTR of SORT1, repressing its expression. Analysis of the sortilin 1 co-immunoprecipitated proteome identified candidate binding proteins that could be differentially regulated as a function of SMCs calcification. Induction of CRD by 5/6 nephrectomy in Apoe−/− mice increased serum phosphate and sortilin 1 serum levels by 2.8-fold and 3.3-fold, respectively, and showed a significant correlation between these two factors. Moreover, CRD dramatically increased sortilin 1 expression in medial SMCs (+667%).

Vascular calcification is a prominent feature of chronic inflammatory disorders such as chronic renal disease (CRD) and atherosclerosis, and has no medical therapies. Human genome wide association studies linked the SORT1 gene, encoding sortilin 1, with increased risk of cardiovascular diseases and coronary artery calcification; however, underlying mechanisms are unknown. The work reported herein demonstrates that sortilin 1 contributes to the osteogenic transition of vascular smooth muscle cells (SMC). The current study shows for the first time a direct role of sortilin 1 in vascular calcification, demonstrating that sortilin 1 is a therapeutic target for patients with CRD.

Genome wide association studies (GWAS) have strongly associated the 1p13 locus harbouring the SORT1 gene that encodes sortilin 1 with plasma low-density lipoprotein (LDL) cholesterol levels, the onset of myocardial infarction and coronary artery calcification (Musunuru K et al, *Nature*, 2010; Kathiresan S et al, *Nature Genetics*, 2009; O'Donnell C J et al, *Circulation*, 2011). Furthermore, the global absence of Sort1 reduces secretion of lipoproteins from the liver and ameliorates hypercholesterolemia and atherosclerosis in LDL receptor-deficient mice (Kjolby M et al, *Cell Metabolism*, 2010). It is a novel finding by the inventors that sortilin 1 plays a direct role in vascular calcification. In calcified regions of human atherosclerotic plaques, cells co-express sortilin 1 and activate RUNX2, a regulator of bone osteoblast differentiation. In human SMC osteogenic phosphate-rich media induce an osteoblast-like phenotype, coinciding with an increase expression of sortilin 1 mRNA/protein. Silencing of sortilin 1 significantly reduce calcification of SMC measured by the alkaline phosphatase activity and amount of matrix-calcium. In contrast, increase endogenous or exogenous sortilin 1 promotes SMC calcification. Using proteomics approach we identified candidate binding proteins that differentially regulated as a function of SMC calcification. The association of sortilin 1 to cytosolic proteins (e.g. myosin 9) gets lost in calcified SMC, whereas the association to alkaline phosphatase, caveolin-1, erlin-1 and cathepsin-D was strongly increased in calcified SMC. Induction of CRD by 5/6 nephrectomy in Apoe-deficient mice increases serum phosphate and sortilin 1 serum levels and show a significant correlation between these two factors. Moreover, CRD dramatically increases sortilin 1 expression in medial SMC. Collectively, the work reported herein shows that sortilin 1 is a novel regulator of hyperphosphatemia-triggered osteogenic vascular SMC transition and calcification. This is the first report to inventors' knowledge to demonstrate a direct role of sortilin 1 in vascular calcification.

Our study demonstrates a novel finding that sortilin 1 is present in calcified atherosclerotic plaques expressed by osteogenic cells within the lesion. Inhibition of sortilin 1 prevents mineralization of SMC in vitro. In vivo, in a mouse model of CRD sortilin 1 was highly increased in calcified vessel media and intima. Serum sortilin 1 levels were increased in CRD mice and correlate positively with phosphate levels.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

The invention claimed is:

1. A method for inhibiting calcification of a smooth muscle cell, the method comprising inhibiting an activity or amount of sortilin 1 in the smooth muscle cell.

2. The method of claim 1, wherein said inhibiting is in vitro.

3. The method of claim 1, wherein said inhibiting is in vivo.

4. The method of claim 3, wherein said inhibiting is in a mammal.

5. The method of claim 3, wherein said inhibiting is in a human.

6. The method of claim 3, wherein said inhibiting is in a subject in need of inhibition of calcification.

7. The method of claim 6, wherein said calcification is cardiovascular calcification.

8. The method of claim 6, wherein said calcification is valvular or arterial calcification.

9. The method of claim 6, wherein the subject has severe renal failure, has a transcatheter aortic valve implantation, has chronic coronary atherosclerosis, has aortic stenosis, or has mineral imbalance or a calcium/phosphate disorder.

* * * * *